United States Patent
Saha et al.

(10) Patent No.: US 10,758,613 B2
(45) Date of Patent: *Sep. 1, 2020

(54) COMBINATION THERAPIES USING ANTI-METABOLITES AND AGENTS THAT TARGET TUMOR-ASSOCIATED STROMA OR TUMOR CELLS

(71) Applicants: BIOMED VALLEY DISCOVERIES, INC., Kansas City, MO (US); THE UNITED STATES OF AMERICA, AS REPRESENTED BY THE SECRETARY, DEPARTMENT OF HEALTH AND HUMAN SERVICES, Bethesda, MD (US)

(72) Inventors: Saurabh Saha, Wellesley Hills, MA (US); Xiaoyan M. Zhang, Lexington, MA (US); Dimiter Dimitrov, Frederick, MD (US); Zhongyu Zhu, Frederick, MD (US); Brad St. Croix, Frederick, MD (US); Enrique Zudaire, Germantown, MD (US)

(73) Assignees: THE UNITED STATES OF AMERICA, AS REPRESENTED BY THE SECRETARY, DEPARTMENT OF HEALTH AND HUMAN SERVICES NATIONAL INTSTITUTES OF HEALTH, Bethesda, MD (US); BIOMED VALLEY DISCOVERIES, INC., Kansas City, MO (US)

( * ) Notice: Subject to any disclaimer, the term of this patent is extended or adjusted under 35 U.S.C. 154(b) by 130 days.

This patent is subject to a terminal disclaimer.

(21) Appl. No.: 15/317,055

(22) PCT Filed: Jun. 9, 2015

(86) PCT No.: PCT/US2015/034949
§ 371 (c)(1),
(2) Date: Dec. 7, 2016

(87) PCT Pub. No.: WO2015/191617
PCT Pub. Date: Dec. 17, 2015

(65) Prior Publication Data
US 2017/0112926 A1    Apr. 27, 2017

Related U.S. Application Data

(60) Provisional application No. 62/009,380, filed on Jun. 9, 2014.

(51) Int. Cl.
*A61K 39/395*   (2006.01)
*A61K 31/513*   (2006.01)
(Continued)

(52) U.S. Cl.
CPC ...... *A61K 39/39558* (2013.01); *A61K 31/337* (2013.01); *A61K 31/4745* (2013.01); *A61K 31/513* (2013.01); *A61K 31/7068* (2013.01); *A61K 33/24* (2013.01); *A61K 45/06* (2013.01); *A61K 47/6817* (2017.08); *A61K 47/6855* (2017.08); *A61K 47/6857* (2017.08); *A61K 47/6863* (2017.08); *A61K 47/6865* (2017.08);
(Continued)

(58) Field of Classification Search
None
See application file for complete search history.

(56) References Cited

U.S. PATENT DOCUMENTS

| 4,816,567 A | 3/1989 | Cabilly et al. |
| 5,034,506 A | 7/1991 | Summerton et al. |

(Continued)

FOREIGN PATENT DOCUMENTS

| AU | 2009200977 A1 | 4/2009 |
| WO | 199005144 | 5/1990 |

(Continued)

OTHER PUBLICATIONS

Codacci-Pisanelli, G., High-dose 5-Fluorouracil with uridine-diphosphoglucose rescue increases thymidylate synthase inhibition but not 5-Fluorouracil incorporation into RNA in murine tumors, Oncology 62(4): 363-70 (2002).

(Continued)

*Primary Examiner* — Brad Duffy
(74) *Attorney, Agent, or Firm* — Bryan Cave Leighton Paisner LLP

(57) ABSTRACT

The present invention provides, inter alia, methods for treating or ameliorating the effects of a disease, such as cancer, in a subject. The methods include: administering to a subject in need thereof (a) a therapeutically effective amount of an agent selected from an anti-metabolite agent or analog thereof and combinations thereof; and (b) a therapeutically effective amount of a monoclonal antibody or antigen binding fragment thereof, wherein the monoclonal antibody contains: (i) a heavy chain variable region (VH), which includes an amino acid sequence selected from SEQ ID NO:1, SEQ ID NO:3, SEQ ID NO:5, and SEQ ID NO:7; and (ii) a light chain variable region (VL), which includes an amino acid sequence selected from SEQ ID NO:2, SEQ ID NO:4, SEQ ID NO:6, and SEQ ID NO:8. Compositions, including pharmaceutical compositions, and kits for treating diseases, such as cancer, are also provided herein.

11 Claims, 22 Drawing Sheets

Specification includes a Sequence Listing.

(51) Int. Cl.
| | |
|---|---|
| A61K 31/4745 | (2006.01) |
| A61K 31/7068 | (2006.01) |
| A61K 33/24 | (2019.01) |
| C07K 16/18 | (2006.01) |
| C07K 16/22 | (2006.01) |
| A61K 31/337 | (2006.01) |
| A61K 47/68 | (2017.01) |
| A61K 45/06 | (2006.01) |
| C07K 16/30 | (2006.01) |
| A61K 39/00 | (2006.01) |

(52) U.S. Cl.
CPC .......... *A61K 47/6869* (2017.08); *C07K 16/18* (2013.01); *C07K 16/22* (2013.01); *C07K 16/30* (2013.01); *A61K 2039/505* (2013.01); *A61K 2039/507* (2013.01); *A61K 2039/545* (2013.01); *C07K 2317/24* (2013.01); *C07K 2317/52* (2013.01); *C07K 2317/55* (2013.01); *C07K 2317/56* (2013.01); *C07K 2317/72* (2013.01); *C07K 2317/73* (2013.01); *C07K 2317/732* (2013.01); *C07K 2317/76* (2013.01); *C07K 2317/92* (2013.01); *C07K 2317/94* (2013.01)

(56) References Cited

U.S. PATENT DOCUMENTS

| | | | |
|---|---|---|---|
| 5,235,033 | A | 8/1993 | Summerton et al. |
| 5,270,163 | A | 12/1993 | Gold et al. |
| 7,825,229 | B2 | 11/2010 | Itzhak et al. |
| 8,394,378 | B2 | 3/2013 | Kehoe et al. |
| 8,519,107 | B2 | 8/2013 | Almagro et al. |
| 9,765,142 | B2 * | 9/2017 | Dimitrov ............... C07K 16/28 |
| 2002/0115080 | A1 | 8/2002 | Skouv et al. |
| 2003/0059937 | A1 | 3/2003 | Ruben et al. |
| 2003/0166163 | A1 | 9/2003 | Gillies et al. |
| 2005/0107325 | A1 | 5/2005 | Manoharan et al. |
| 2005/0182005 | A1 | 8/2005 | Tuschl et al. |
| 2007/0259352 | A1 | 11/2007 | Bentwich et al. |
| 2010/0047784 | A1 | 2/2010 | Gilad et al. |
| 2014/0134179 | A1 | 5/2014 | St. Croix et al. |

FOREIGN PATENT DOCUMENTS

| | | |
|---|---|---|
| WO | 2005116250 | 12/2005 |
| WO | 2006126040 | 11/2006 |
| WO | 2011053763 A2 | 5/2011 |
| WO | WO-2012174160 A1 * 12/2012 | ............ C07K 16/28 |
| WO | 2015054691 A2 | 4/2015 |

OTHER PUBLICATIONS

Geary, S. M., The Combination of a Low-Dose Chemotherapeutic Agent, 5-Fluorouracil, and an Adenoviral Tumor Vaccine Has a Synergistic Benefit on Survival in a Tumor Model System, PLOS One 8(6): e67904.

Pierce Chemical Co., Pierce Catalog and Handbook, 1994-1995. Pierce Chemical Co., Rockford, Ill.
Huse, et al, Science 246:1275-1281 (1989).
Winter and Harris, Immunology Today, 14:243-246 (1993).
Ward et al, Binding activities of a repertoise of single immunoglobulin variable domains secreted from *Escherichia coli*, Nature 341: 544-546 (1989).
Harlow, E, et al. "Antibodies: A Laboratory Manual" Science, 1988.
Hilyard et al., Protein Engineering: A practical approach (IRL press 1992). This is a book in the National Library of Australia: Protein engineering : a practical approach / edited by Anthony R. Rees, Michael J.E. Sternberg, and Ronald Wetzel.
Borreback, Antibody Engineering, 2d Ed. (Oxford University Press, 1995).
Kuby Immunology, W. H. Freeman (3rd Ed), 1997.
Kabat et al, U.S. Dept. of Health and Human Services, Sequences of Proteins of Immunological Interest (1983).
Chothia, C., et al., Canonical structures for the hypervariable regions of immunoglobulins, Journal of Molecular Biology, 196, 901-917 (1987).
Kohler et al., Continuous cultures of fused cells secreting antibody of predefined specificity, Nature 256: 495 (1975).
Jones et al., Replacing the complementarity-determining regions in a human antibody with those from a mouse. Nature 321: 522-525 (1986).
Reichmann, et al., Reshaping human antibodies for therapy, Nature 332:323-329 (1988).
Presta, Antibody Engineering, Curr. Opin. Biotechnol. 3:294-8 (1992).
Verhoeyen et al., Reshaping human antibodies; Grafting an antilysozyme activity, Science, 239:1534-1536, (1988).
Marks, D., et al., By-passing Immunization Human Antibodies from V-gene Libraries Displayed on Phage, J. Mol. biol. (1991) 222, 581-597.
Knappik et al., Fully synthetic human combinatorial antibody libraries (HuCAL) based on modular consensus frameworks and CDRs randomized with trinucleotides., J. Mol. Biol., Feb. 11, 2000, 296: 57-86.
Carmen, S., et al., Concepts in antibody phage display, Briefings in Functional Genomics and Proteomics, 2002 1 (2) :189-203.
Lonberg, N., et al., Human antibodies from transgenic mice, Int. Rev. Immunol. 1995, 13(1); 65-93.
Bruggemann, M., et al., Production of human antibody repertoires in transgenic mice, Curr Op. in Biotech. Aug. 1997, 8(4): 455-8.
Kontermann, R.E. (ed), In: Bispecific antibodies, Springer Heidelberg Dordrecht London New York, pp. 1-28 (2011).
Brody, E. N., et al., Aptamers as therapeutic and diagnostic agents, Journal of Biotechnology, vol. 74, issue 1, Mar. 2000, pp. 5-13.
Blind, M., et al., Cytoplasmic RNA modulators of an inside-out signal-transduction cascade, (1999) Proc. Natl. Acad. Sci. USA, 96: 3606-3610.
Krutzfeldt, J., et al., Silencing of microRNAs in vivo with 'antagomirs', Nature (Oct. 30, 2005).
Soutschek, J., Therapeutic silencing of an endogenous gene by systemic administration of modified siRNAs, Nature 432:173-178 (2004).

* cited by examiner

1A

1B

FIG. 11
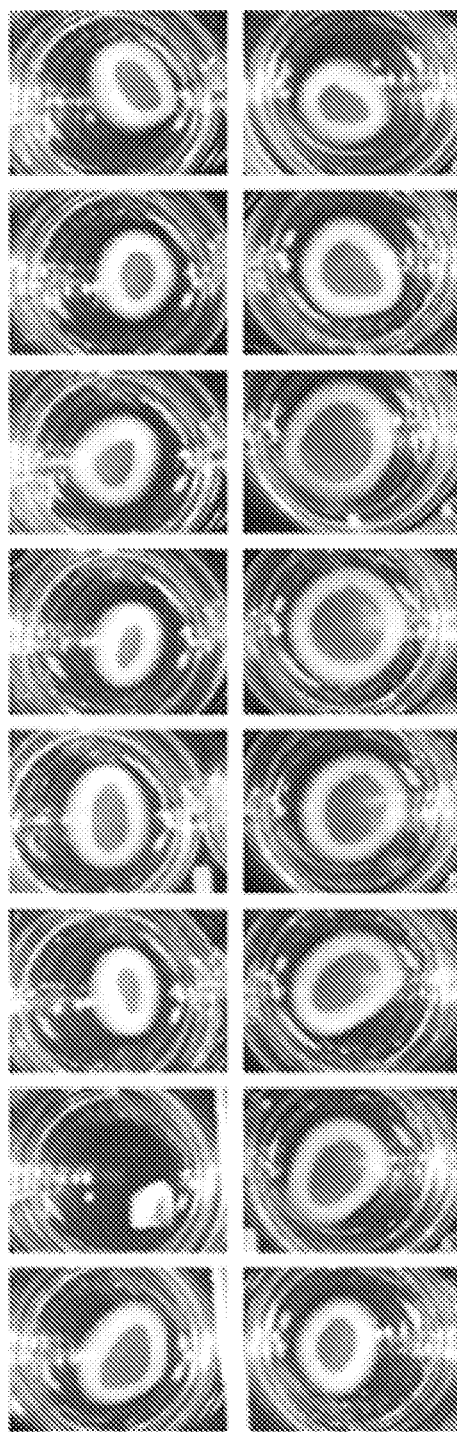
11A
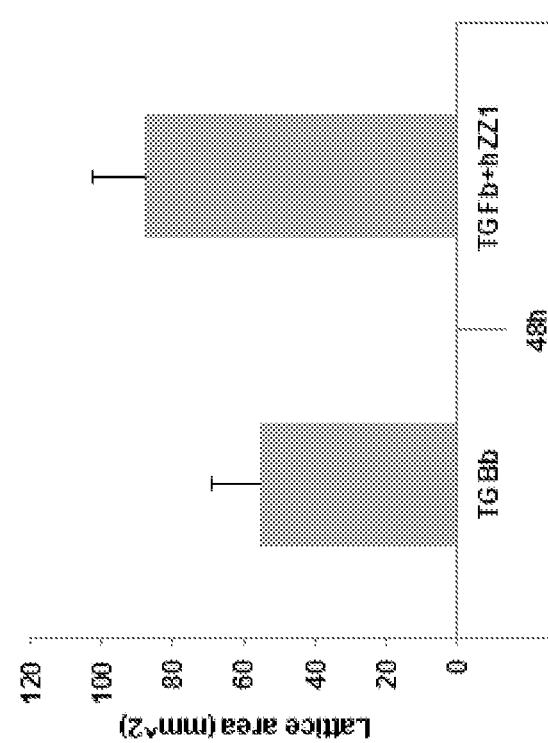
11B

FIG. 12
12A
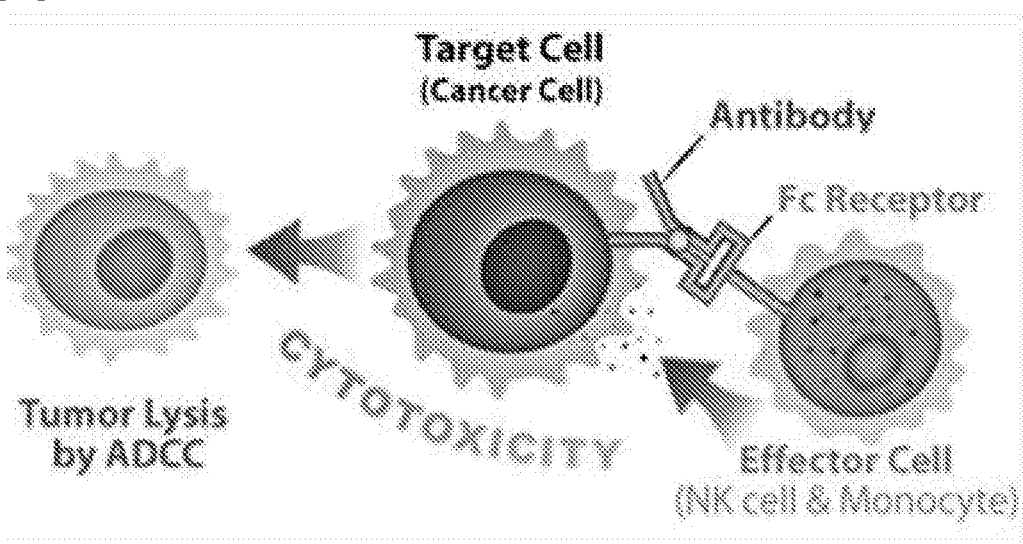
12B
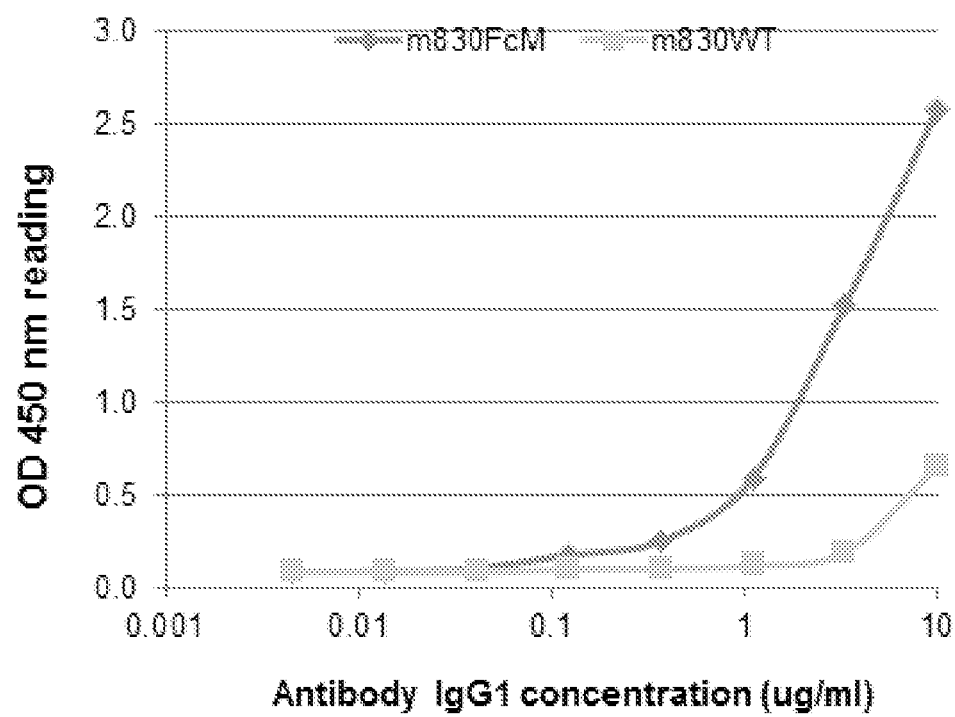

SEQUENCE LISTING

```
<160> NUMBER OF SEQ ID NOS: 22

<210> SEQ ID NO 1
<211> LENGTH: 117
<212> TYPE: PRT
<213> ORGANISM: Artificial
<220> FEATURE:
<223> OTHER INFORMATION: TEM825 mAB VH polypeptide

<400> SEQUENCE: 1

Gln Val Gln Leu Val Gln Ser Gly Ala Glu Val Lys Lys Pro Gly Thr
1               5                   10                  15

Ser Val Lys Val Ser Cys Lys Val Pro Gly Tyr Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Lys Phe
    50                  55                  60

Gln Gly Arg Val Thr Ile Thr Gly Glu Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Thr Asp Tyr Met Phe Asp Tyr Trp Gly Gln Gly Thr Leu
            100                 105                 110

Val Thr Val Ser Ser
        115

<210> SEQ ID NO 2
<211> LENGTH: 107
<212> TYPE: PRT
<213> ORGANISM: Artificial
<220> FEATURE:
<223> OTHER INFORMATION: TEM825 mAb VL polypeptide

<400> SEQUENCE: 2

Ser Ser Glu Leu Thr Gln Asp Pro Val Val Ser Val Ala Leu Gly Glu
1               5                   10                  15

Thr Val Ser Ile Thr Cys Gln Gly Asp Asn Leu Arg Asp Phe Tyr Ala
            20                  25                  30

Ser Trp Tyr Gln Gln Lys Pro Gly Gln Ala Pro Leu Leu Val Met Tyr
        35                  40                  45

Gly Lys Asn Arg Arg Pro Ser Gly Ile Pro Asp Arg Phe Ser Gly Ser
    50                  55                  60

Thr Ser Gly Asn Thr Leu Ser Leu Thr Ile Thr Gly Ala Gln Ala Glu
65                  70                  75                  80

Asp Glu Ala Asp Tyr Tyr Cys Ser Ser Arg Asp Asn Ser Lys His Val
                85                  90                  95

Val Phe Gly Gly Gly Thr Lys Val Thr Val Leu
            100                 105
```

<210> SEQ ID NO 3
<211> LENGTH: 117
<212> TYPE: PRT
<213> ORGANISM: Artificial
<220> FEATURE:
<223> OTHER INFORMATION: TEM822 mAb VH

<400> SEQUENCE: 3

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Asp Tyr Met Phe Asp Tyr Trp Gly Gln Gly Thr Leu
            100                 105                 110

Val Thr Val Ser Ser
        115
```

<210> SEQ ID NO 4
<211> LENGTH: 107
<212> TYPE: PRT
<213> ORGANISM: Artificial
<220> FEATURE:
<223> OTHER INFORMATION: TEM822 mAb VL

<400> SEQUENCE: 4

```
Ser Ser Glu Leu Thr Gln Asp Pro Val Val Ser Val Ala Leu Gly Glu
1               5                   10                  15

Thr Val Ser Ile Thr Cys Gln Gly Asp Asn Leu Arg Asp Phe Tyr Ala
            20                  25                  30

Ser Trp Tyr Gln Gln Lys Pro Gly Gln Ala Pro Leu Leu Val Met Tyr
        35                  40                  45

Gly Lys Asn Arg Arg Pro Ser Gly Ile Pro Asp Arg Phe Ser Gly Ser
    50                  55                  60

Thr Ser Gly Asn Thr Leu Ser Leu Thr Ile Thr Gly Ala Gln Ala Glu
65                  70                  75                  80

Asp Glu Ala Asp Tyr Tyr Cys Ser Ser Arg Asp Asn Ser Lys His Val
                85                  90                  95

Val Phe Gly Gly Gly Thr Lys Val Thr Val Leu
            100                 105
```

<210> SEQ ID NO 5
<211> LENGTH: 121
<212> TYPE: PRT
<213> ORGANISM: Artificial
<220> FEATURE:
<223> OTHER INFORMATION: TEM830 mAb VH

<400> SEQUENCE: 5

```
Glu Val Gln Leu Val Glu Ser Gly Gly Gly Val Val Gln Pro Gly Arg
1               5                   10                  15
```

```
Ser Val Arg Leu Ser Cys Ala Ala Ser Gly Phe Thr Phe Ser Thr Tyr
            20                  25                  30

Thr Met His Trp Val Arg Gln Ala Pro Gly Lys Gly Leu Glu Trp Val
        35                  40                  45

Ala Ile Ile Ser Asn Asp Gly Ser Asn Lys Tyr Tyr Ala Asp Pro Val
50                      55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Gly Ser Ser Trp Tyr Arg Gly Asn Trp Phe Asp Pro Trp Gly
            100                 105                 110

Gln Gly Thr Leu Val Thr Val Ser Ser
            115                 120

<210> SEQ ID NO 6
<211> LENGTH: 108
<212> TYPE: PRT
<213> ORGANISM: Artificial
<220> FEATURE:
<223> OTHER INFORMATION: TEM830 mAb VL

<400> SEQUENCE: 6

Asp Ile Gln Met Thr Gln Ser Pro Ser Ser Leu Ser Ala Ser Val Gly
1               5                   10                  15

Asp Arg Val Thr Ile Ala Cys Arg Ala Ser Gln Thr Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Ser Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Thr Tyr Ser Pro Pro Ile
                85                  90                  95

Thr Phe Gly Gln Gly Thr Arg Leu Glu Ile Lys Arg
            100                 105

<210> SEQ ID NO 7
<211> LENGTH: 121
<212> TYPE: PRT
<213> ORGANISM: Artificial
<220> FEATURE:
<223> OTHER INFORMATION: TEM863 mAb VH

<400> SEQUENCE: 7

Glu Val Gln Leu Val Glu Thr Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Thr Ser Gly Ser Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Gly Leu Arg Ser Asp Asp Thr Ala Val Tyr Tyr Cys
                85                  90                  95
```

Val Arg Asp Pro Gly Ser Pro Lys Trp Leu Ala Phe Asp Pro Trp Gly
            100                 105                 110
Gln Gly Thr Leu Val Thr Val Ser Ser
        115                 120

<210> SEQ ID NO 8
<211> LENGTH: 108
<212> TYPE: PRT
<213> ORGANISM: Artificial
<220> FEATURE:
<223> OTHER INFORMATION: TEM863 mAb VL

<400> SEQUENCE: 8

Asp Ile Gln Leu Thr Gln Ser Pro Ser Ser Leu Ser Ala Ser Val Gly
1               5                   10                  15
Asp Arg Val Thr Ile Thr Cys Arg Ala Ser Arg Ala Ile Ser Arg Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Ser Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Phe Cys Gln Gln Thr Tyr Ser Pro Pro Ile
                85                  90                  95
Thr Phe Gly Gln Gly Thr Arg Leu Glu Ile Lys Arg
            100                 105

<210> SEQ ID NO 9
<211> LENGTH: 5909
<212> TYPE: DNA
<213> ORGANISM: Homo sapiens

<400> SEQUENCE: 9
atcatattta aaatctggga caaagaaccg tcgggacgga actccttcca ttgcaaaagc    60
tcggcgcggc ctcgggagct gcccggcggc cccggaccga ggcagccctc ccctttaaaa   120
gaagcggagg acaggattgg gatccttgaa acccgaaacc cagaaacagc atcggagcgg   180
aaaccagagg ggaaaccttg aactcctcca gacaattgct tccggggagt tgcgagggag   240
cgagggggaa taaggacccc gcgaggaagg gcccgcggat ggcgcgtccc tgagggtcgt   300
ggcgagttcg cggagcgtgg gaaggagcgg accctgctct ccccgggctg cgggccatgg   360
ccacggcgga gcggagagcc ctcggcatcg gcttccagtg gctctctttg gccactctgg   420
tgctcatctg cgccgggcaa gggggacgca gggaggatgg gggtccagcc tgctacggcg   480
gatttgacct gtacttcatt ttggacaaat caggaagtgt gctgcaccac tggaatgaaa   540
tctattactt tgtggaacag ttggctcaca aattcatcag cccacagttg agaatgtcct   600
ttattgtttt ctccacccga ggaacaacct aatgaaact gacagaagac agagaacaaa   660
tccgtcaagg cctagaagaa ctccagaaag ttctgccagg aggagacact tacatgcatg   720
aaggatttga aagggccagt gagcagattt attatgaaaa cagacaaggg tacaggacag   780
ccagcgtcat cattgctttg actgatggag aactccatga agatctcttt ttctattcag   840
agagggaggc taataggtct cgagatcttg tgcaattgt ttactgtgtt ggtgtgaaag   900
atttcaatga gacacagctg gcccggattg cggacagtaa ggatcatgtg tttcccgtga   960
atgacggctt tcaggctctg caaggcatca tccactcaat tttgaagaag tcctgcatcg  1020

-continued

```
aaattctagc agctgaacca tccaccatat gtgcaggaga gtcatttcaa gttgtcgtga      1080
gaggaaacgg cttccgacat gcccgcaacg tggacagggt cctctgcagc ttcaagatca      1140
atgactcggt cacactcaat gagaagccct tttctgtgga agatacttat ttactgtgtc      1200
cagcgcctat cttaaaagaa gttggcatga aagctgcact ccaggtcagc atgaacgatg      1260
gcctctcttt tatctccagt tctgtcatca tcaccaccac acactgttct gacggttcca      1320
tcctggccat cgccctgctg atcctgttcc tgctcctagc cctggctctc ctctggtggt      1380
tctggcccct ctgctgcact gtgattatca aggaggtccc tccaccccct gccgaggaga      1440
gtgaggaaga gatgatgat ggtctgccta agaaaaagtg gccaacggta gacgcctctt       1500
attatggtgg gagaggcgtt ggaggcatta aagaatggaa ggttcgttgg ggagaaaagg      1560
gctccacaga agaaggtgct aagttggaaa aggcaaagaa tgcaagagtc aagatgccgg      1620
agcaggaata tgaattccct gagccgcgaa atctcaacaa caatatgcgt cggccttctt      1680 cccccccggaa gtggtactct ccaatcaagg gaaaactcga tgccttgtgg gtcctactga    1740
ggaaaggata tgatcgtgtg tctgtgatgc gtccacagcc aggagacacg gggcgctgca      1800
tcaacttcac cagggtcaag aacaaccagc cagccaagta cccactcaac aacgcctacc      1860
acacctcctc gccgcctcct gccccccatct acactccccc acctcctgcg ccccactgcc     1920
ctcccccgcc ccccagcgcc cctacccctc ccatcccgtc cccacttccc acccttcccc      1980
ctcctcccca ggctccacct cccaacaggg cacctcctcc ctcccgcccct cctccaaggc     2040 cttctgtcta gagcccaaag ttcctgctct gggctctctc agaaacttca ggagatgtta      2100
gaacaagtct ttccagttag agaagaggag tggtgataaa gcccactgac cttcacacat      2160
tctaaaaatt ggttggcaat gccagtatac caacaatcat gatcagctga agaaaacaga     2220
tattttaaat tgccagaaaa caaatgatga ggcaactaca gtcagattta tagccagcca     2280
tctatcacct ctagaaggtt ccagagacag tgaaactgca agatgctctc aacaggatta     2340
tgtctcatgg agaccagtaa gaaaatcatt tatctgaagg tgaaatgcag agttggataa     2400
gaaatacatt gctgggtttc taaaatgctg ccttcctgcc tctactccac ctccatccct     2460
ggactttgga cccttggcct aggagcctaa ggaccttcac ccctgtgcac cacccaagaa     2520
agaggaaaac tttgcctaca actttggaaa tgctggggtc cctggtgtgg taagaaactc     2580
aacatcagac gggtatgcag aaggatgttc ttctgggatt tgcaggtaca taaaaaatgt    2640
atggcatctt ttccttgcaa attcttccag tttccaagtg agaagggggag caggtgttta   2700 ctgatgaaa aggtatgttg ctatgttgat gtgtaagtga aatcagttgt gtgcaataga    2760
caggggcgta ttcatgggag catcagccag tttctaaaac ccacaggcca tcagcagcta     2820
gaggtggctg gctttggcca gacatggacc ctaaatcaac agacaatggc attgtcgaag     2880
agcaacctgt taatgaatca tgttaaaaat caaggtttgg cttcagttta aatcacttga     2940
ggtatgaagt ttatcctgtt ttccagagat aaacataagt tgatcttccc aaaataccat     3000
cattaggacc tatcacacaa tatcactagt ttttttttgtt tgtttgtttt ttgttttttt    3060
tcttggtaaa gccatgcacc acagacttct gggcagagct gagagacaat ggtcctgaca     3120
taataaggat ctttgattaa cccccataag gcatgtgtgt gtatacaaat atacttctct     3180
ttggcttttc gacatagaac ctcagctgtt aaccaagggg aaatacatca gatctgcaac     3240
acagaaatgc tctgcctgaa atttccacca tgcctaggac tcaccccatt tatccaggtc     3300
tttctggatc tgtttaatca ataagcccta taatcacttg ctaaacactg ggcttcatca     3360
```

```
cccagggata aaaacagaga tcattgtctt ggacctcctg catcagccta ttcaaaatta    3420
tctctctctc tagcttttcca caaatcctaa aattcctgtc ccaagccacc caaattctca   3480
gatcttttct ggaacaaggc agaatataaa ataaatatac atttagtggc ttgggctatg    3540
gtctccaaag atccttcaaa aatacatcaa gccagcttca ttcactcact ttacttagaa    3600
cagagatata agggcctggg atgcatttat tttatcaata ccaattttg tggccatggc     3660 agacattgct aatcaatcac agcactattt cctattaagc ccactgattt cttcacaatc    3720
cttctcaaat tacaattcca aagagccgcc actcaacagt cagatgaacc caacagtcag    3780
atgagagaaa tgaaccctac ttgctatctc tatcttagaa agcaaaaaca aacaggagtt    3840
tccagggaga atgggaaagc caggggcat aaaaggtaca gtcaggggaa aatagatcta     3900
ggcagagtgc cttagtcagg gaccacgggc gctgaatctg cagtgccaac accaaactga    3960
cacatctcca ggtgtacctc caaccctagc cttctcccac agctgcctac aacagagtct    4020
cccagccttc tcagagagct aaaaccagaa atttccagac tcatgaaagc aaccccccag    4080
cctctcccca accctgccgc attgtctaat ttttagaaca ctaggcttct tctttcatgt    4140
agttcctcat aagcaggggc cagaatatct cagccacctg cagtgacatt gctggacccc    4200
tgaaaaccat tccataggag aatgggttcc ccaggctcac agtgtagaga cattgagccc    4260
atcacaactg ttttgactgc tggcagtcta aaacagtcca cccacccat ggcactgccg      4320 cgtgattccc gcggccattc agaagttcaa gccgagatgc tgacgttgct gagcaacgag    4380
atggtgagca tcagtgcaaa tgcaccattc agcacatcag tcatatgccc agtgcagtta    4440
caagatgttg tttcggcaaa gcattttgat ggaatagggga actgcaaatg tatgatgatt   4500
ttgaaaaggc tcagcaggat ttgttcttaa accgactcag tgtgtcatcc ccggttattt     4560
agaattacag ttaagaagga gaaacttcta taagactgta tgaacaaggt gatatcttca    4620
tagtgggcta ttacaggcag gaaaatgttt taactggttt acaaaatcca tcaatacttg    4680
tgtcattccc tgtaaaaggc aggagacatg tgattatgat caggaaactg cacaaaatta    4740 ttgtttcag cccccgtgtt attgtccttt tgaactgttt ttttttttat taaagccaaa      4800
tttgtgttgt atatattcgt attccatgtg ttagatggaa gcatttccta tccagtgtga   4860
ataaaaagaa cagttgtagt aaattattat aaagccgatg atatttcatg gcaggttatt     4920
ctaccaagct gtgcttgttg gttttttccca tgactgtatt gcttttataa atgtacaaat   4980
agttactgaa atgacgagac ccttgtttgc acagcattaa taagaaacctt gataagaacc    5040 atattctgtt gacagccagc tcacagtttc ttgcctgaag cttggtgcac cctccagtga    5100
gacacaagat ctctctttta ccaaagttga gaacagagct ggtggattaa ttaatagtct    5160
tcgatatctg gccatgggta acctcattgt aactatcatc agaatgggca gagatgatct    5220
tgaagtgtca catacactaa agtccaaaca ctatgtcaga tgggggtaaa atccattaaa    5280
gaacaggaaa aaataattat aagatgataa gcaaatgttt cagcccaatg tcaacccagt    5340
taaaaaaaaa attaatgctg tgtaaaatgg ttgaattagt ttgcaaacta tataaagaca    5400
tatgcagtaa aaagtctgtt aatgcacatc ctgtgggaat ggagtgttct aaccaattgc    5460
cttttcttgt tatctgagct ctcctatatt atcatactca gataaccaaa ttaaaagaat    5520
tagaatatga tttttaatac acttaacatt aaactcttct aactttcttc tttctgtgat    5580
aattcagaag atagttatgg atcttcaatg cctctgagtc attgttataa aaaatcagtt    5640
atcactatac catgctatag gagactgggc aaaacctgta caatgacaac cctggaagtt    5700
gcttttttta aaaaaataat aaatttctta aatcaactct tttttctggt tgtctgtttg    5760
```

```
ttataaagtg caacgtattc aagtcctcaa tatcctgatc ataataccat gctataggag      5820
actgggcaaa acctgtacaa tgacaaccct ggaagttgct tttttaaaaa aataataaa       5880 tttcttaaat caaaaaaaaa aaaaaaaaa                                        5909
```

<210> SEQ ID NO 10
<211> LENGTH: 564
<212> TYPE: PRT
<213> ORGANISM: Homo sapiens

<400> SEQUENCE: 10

```
Met Ala Thr Ala Glu Arg Arg Ala Leu Gly Ile Gly Phe Gln Trp Leu
1               5                   10                  15

Ser Leu Ala Thr Leu Val Leu Ile Cys Ala Gly Gln Gly Gly Arg Arg
            20                  25                  30

Glu Asp Gly Gly Pro Ala Cys Tyr Gly Gly Phe Asp Leu Tyr Phe Ile
        35                  40                  45

Leu Asp Lys Ser Gly Ser Val Leu His His Trp Asn Glu Ile Tyr Tyr
    50                  55                  60

Phe Val Glu Gln Leu Ala His Lys Phe Ile Ser Pro Gln Leu Arg Met
65                  70                  75                  80

Ser Phe Ile Val Phe Ser Thr Arg Gly Thr Thr Leu Met Lys Leu Thr
                85                  90                  95

Glu Asp Arg Glu Gln Ile Arg Gln Gly Leu Glu Glu Leu Gln Lys Val
            100                 105                 110

Leu Pro Gly Gly Asp Thr Tyr Met His Glu Gly Phe Glu Arg Ala Ser
        115                 120                 125

Glu Gln Ile Tyr Tyr Glu Asn Arg Gln Gly Tyr Arg Thr Ala Ser Val
    130                 135                 140

Ile Ile Ala Leu Thr Asp Gly Glu Leu His Glu Asp Leu Phe Phe Tyr
145                 150                 155                 160

Ser Glu Arg Glu Ala Asn Arg Ser Arg Asp Leu Gly Ala Ile Val Tyr
                165                 170                 175

Cys Val Gly Val Lys Asp Phe Asn Glu Thr Gln Leu Ala Arg Ile Ala
            180                 185                 190

Asp Ser Lys Asp His Val Phe Pro Val Asn Asp Gly Phe Gln Ala Leu
        195                 200                 205

Gln Gly Ile Ile His Ser Ile Leu Lys Lys Ser Cys Ile Glu Ile Leu
    210                 215                 220

Ala Ala Glu Pro Ser Thr Ile Cys Ala Gly Glu Ser Phe Gln Val Val
225                 230                 235                 240

Val Arg Gly Asn Gly Phe Arg His Ala Arg Asn Val Asp Arg Val Leu
                245                 250                 255

Cys Ser Phe Lys Ile Asn Asp Ser Val Thr Leu Asn Glu Lys Pro Phe
            260                 265                 270

Ser Val Glu Asp Thr Tyr Leu Leu Cys Pro Ala Pro Ile Leu Lys Glu
        275                 280                 285

Val Gly Met Lys Ala Ala Leu Gln Val Ser Met Asn Asp Gly Leu Ser
    290                 295                 300

Phe Ile Ser Ser Ser Val Ile Ile Thr Thr Thr His Cys Ser Asp Gly
305                 310                 315                 320

Ser Ile Leu Ala Ile Ala Leu Leu Ile Leu Phe Leu Leu Leu Ala Leu
                325                 330                 335

Ala Leu Leu Trp Trp Phe Trp Pro Leu Cys Cys Thr Val Ile Ile Lys
```

```
                    340                 345                 350
Glu Val Pro Pro Pro Ala Glu Glu Ser Glu Glu Asp Asp
            355                 360                 365

Gly Leu Pro Lys Lys Lys Trp Pro Thr Val Asp Ala Ser Tyr Tyr Gly
        370                 375                 380

Gly Arg Gly Val Gly Ile Lys Arg Met Glu Val Arg Trp Gly Glu
385                 390                 395                 400

Lys Gly Ser Thr Glu Glu Gly Ala Lys Leu Glu Lys Ala Lys Asn Ala
                405                 410                 415

Arg Val Lys Met Pro Glu Gln Glu Tyr Glu Phe Pro Glu Pro Arg Asn
            420                 425                 430

Leu Asn Asn Asn Met Arg Arg Pro Ser Ser Pro Arg Lys Trp Tyr Ser
        435                 440                 445

Pro Ile Lys Gly Lys Leu Asp Ala Leu Trp Val Leu Leu Arg Lys Gly
    450                 455                 460

Tyr Asp Arg Val Ser Val Met Arg Pro Gln Pro Gly Asp Thr Gly Arg
465                 470                 475                 480

Cys Ile Asn Phe Thr Arg Val Lys Asn Asn Gln Pro Ala Lys Tyr Pro
                485                 490                 495

Leu Asn Asn Ala Tyr His Thr Ser Ser Pro Pro Ala Pro Ile Tyr
            500                 505                 510

Thr Pro Pro Pro Pro Ala Pro His Cys Pro Pro Pro Pro Ser Ala
        515                 520                 525

Pro Thr Pro Pro Ile Pro Ser Pro Ser Thr Leu Pro Pro Pro
    530                 535                 540

Gln Ala Pro Pro Pro Asn Arg Ala Pro Pro Pro Ser Arg Pro Pro Pro
545                 550                 555                 560

Arg Pro Ser Val

<210> SEQ ID NO 11
<211> LENGTH: 351
<212> TYPE: DNA
<213> ORGANISM: Artificial
<220> FEATURE:
<223> OTHER INFORMATION: TEM825 mAb VH cDNA

<400> SEQUENCE: 11
caggtccagc tggtgcagtc tggggctgag gtgaagaagc ctgggacctc agtgaaggtc      60
tcctgcaagg ttcctggata caccttcagc agctatgcta tcagctgggt gcgacaggcc    120
cctggacaag gcttgagtg gatgggaggg atcatcccta tctttggtac aacaaactac    180
gcacagaagt tccagggcag agtcacgatt accggggagg aatccacgag cacagtctac    240
atggagctga gcagcctgag atctgaggac acggccgtgt attactgtgc gagagatacg    300
gactacatgt ttgactactg gggccaggga accctggtca ccgtgagctc a             351

<210> SEQ ID NO 12
<211> LENGTH: 321
<212> TYPE: DNA
<213> ORGANISM: Artificial
<220> FEATURE:
<223> OTHER INFORMATION: TEM825 mAb VL cDNA

<400> SEQUENCE: 12
tcttctgagc tgactcagga ccctgttgtg tctgtggcct gggagagac agtcagtatc      60 acatgccaag agacaacct cagagacttt tatgcaagct ggtaccaaca gaagccagga    120
```

```
caggcccctc tactagtcat gtatggtaaa acaggcggc cctcagggat cccagaccga    180
ttctctggct ccacctcagg aaacacactt tccttgacca tcactggggc tcaggcggaa    240
gatgaggctg actattactg tagctcccgg gacaacagta agcatgtggt gttcggcggg    300
gggaccaagg tcaccgtcct a                                              321

<210> SEQ ID NO 13
<211> LENGTH: 351
<212> TYPE: DNA
<213> ORGANISM: Artificial
<220> FEATURE:
<223> OTHER INFORMATION: TEM822 mAb VH cDNA

<400> SEQUENCE: 13
caggtccagc tggtgcagtc tggggctgag gtgaagaagc ctggggcctc agtgaaggtc    60
tcctgcaagg tttctggata caccttcagc agctatgcta tcagctgggt gcgacaggcc    120
cctggacaag gcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagatacg    300
gactacatgt ttgactactg gggccaggga accctggtca ccgtgagctc a            351

<210> SEQ ID NO 14
<211> LENGTH: 321
<212> TYPE: DNA
<213> ORGANISM: Artificial
<220> FEATURE:
<223> OTHER INFORMATION: TEM822 mAb VL cDNA

<400> SEQUENCE: 14
tcttctgagc tgactcagga ccctgttgtg tctgtggcct tgggagagac agtcagtatc    60
acatgccaag agacaacct cagagacttt tatgcaagct ggtaccaaca gaagccagga    120
caggcccctc tactagtcat gtatggtaaa acaggcggc cctcagggat cccagaccga    180
ttctctggct ccacctcagg aaacacactt tccttgacca tcactggggc tcaggcggaa    240
gatgaggctg actattactg tagctcccgg gacaacagta agcatgtggt gttcggcggg    300
gggaccaagg tcaccgtcct a                                              321

<210> SEQ ID NO 15
<211> LENGTH: 363
<212> TYPE: DNA
<213> ORGANISM: Artificial
<220> FEATURE:
<223> OTHER INFORMATION: TEM830 mAb VH cDNA

<400> SEQUENCE: 15
gaggtgcagc tggtggagtc tgggggaggc gtggtccagc ctggggaggtc cgtgagactc    60 tcctgtgcag cctctggatt caccttcagt acctatacta tgcactgggt ccgccaggct    120
ccaggcaagg ggctggagtg ggtggcaatt atctcaaatg atggaagcaa taagtactac    180
gcagaccccg tgaggggccg attcaccatc tccagagaca attccaagaa cacgctgtat    240
ctgcaaatga acagcctgag agctgaggac acggctgtgt attactgtgt acgtggcagc    300
agctggtatc gcggaaattg gttcgacccc tggggccagg gaaccctggt caccgtgagc    360
tca                                                                  363

<210> SEQ ID NO 16
<211> LENGTH: 324
```

```
<212> TYPE: DNA
<213> ORGANISM: Artificial
<220> FEATURE:
<223> OTHER INFORMATION: TEM830 mAb VL cDNA

<400> SEQUENCE: 16
gacatccaga tgacccagtc tccatcctcc ctgtctgcat ctgtaggaga cagagtcacc      60
atcgcttgcc gggcaagtca gaccattagt aggtatttaa attggtatca gcagaaacca     120
gggaaagccc ctaagctcct gatctatgct gcatccagtt tgcaaagtgg ggtctcatca     180
aggttcagtg gcagtggatc tgggacagag ttcactctca ccatcagcag tctgcagcct     240
gaagattttg caacttattt ctgtcaacag acttacagtc cccgatcac cttcggccaa      300 gggacacgac tggagattaa acga                                            324

<210> SEQ ID NO 17
<211> LENGTH: 363
<212> TYPE: DNA
<213> ORGANISM: Artificial
<220> FEATURE:
<223> OTHER INFORMATION: TEM863 mAb VH cDNA

<400> SEQUENCE: 17
gaggtgcagc tggtggagac cggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccta ccagtggtag cacaaactat       180
gcacagaagt tcagggcag gtcaccatg accagggaca cgtccatcag cacagcctac       240
atggagctga gcgggctgag atctgacgac actgccgtgt attactgtgt gagagatccg     300
ggttctccta agtggctggc cttcgacccc tggggccagg gcaccctggt caccgtgagc     360
tca                                                                  363

<210> SEQ ID NO 18
<211> LENGTH: 324
<212> TYPE: DNA
<213> ORGANISM: Artificial
<220> FEATURE:
<223> OTHER INFORMATION: TEM863 mAb VL cDNA

<400> SEQUENCE: 18
gacatccagt tgacccagtc tccatcctcc ttgtctgctt ctgtaggaga cagagtcacc      60
atcacttgcc gggcaagtcg ggccattagt aggtatttaa attggtatca gcagaaacca     120
gggaaagccc ctaagctcct gatctatgct gcatccagtt tgcaaagtgg ggtctcatca     180
aggttcagtg gcagtggatc tgggacagag ttcactctca ccatcagcag tctgcagcct     240
gaagattttg caacttattt ctgtcaacag acttacagtc cccgatcac cttcggccaa      300 gggacacgac tggagattaa acgt                                            324

<210> SEQ ID NO 19
<211> LENGTH: 1667
<212> TYPE: DNA
<213> ORGANISM: Homo sapiens

<400> SEQUENCE: 19
atcatattta aaatctggga caaagaaccg tcgggacgga actccttcca ttgcaaaagc      60
tcggcgcggc ctcgggagct gcccggcggc cccggaccga ggcagccctc ccctttaaaa     120
gaagcggagg acaggattgg gatccttgaa acccgaaacc cagaaacagc atcggagcgg     180
```

```
aaaccagagg ggaaaccttg aactcctcca gacaattgct tccggggagt tgcgagggag    240
cgaggggaa taaaggaccc gcgaggaagg gcccgcggat ggcgcgtccc tgagggtcgt    300
ggcgagttcg cggagcgtgg gaaggagcgg accctgctct ccccgggctg cgggccatgg    360
ccacggcgga gcgagagcc ctcggcatcg gcttccagtg gctctctttg gccactctgg    420
tgctcatctg cgccgggcaa gggggacgca gggaggatgg gggtccagcc tgctacggcg    480
gatttgacct gtacttcatt ttggacaaat caggaagtgt gctgcaccac tggaatgaaa    540
tctattactt tgtggaacag ttggctcaca aattcatcag cccacagttg agaatgtcct    600
ttattgtttt ctccacccga ggaacaacct taatgaaact gacagaagac agagaacaaa    660
tccgtcaagg cctagaagaa ctccagaaag ttctgccagg aggagacact tacatgcatg    720
aaggatttga aagggccagt gagcagattt attatgaaaa cagacaaggg tacaggacag    780
ccagcgtcat cattgctttg actgatggag aactccatga agatctcttt ttctattcag    840
agagggaggc taataggtct cgagatcttg gtgcaattgt ttactgtgtt ggtgtgaaag    900
atttcaatga gacacagctg gcccggattg cggacagtaa ggatcatgtg tttcccgtga    960
atgacggctt tcaggctctg caaggcatca tccactcaat tttgaagaag tcctgcatcg   1020
aaattctagc agctgaacca tccaccatat gtgcaggaga gtcatttcaa gttgtcgtga   1080
gaggaaacgg cttccgacat gcccgcaacg tggacagggt cctctgcagc ttcaagatca   1140
atgactcggt cacactcaat gagaagccct ttctgtggga agatacttat ttactgtgtc   1200
cagcgcctat cttaaaagaa gttggcatga agctgcact ccaggtcagc atgaacgatg   1260
gcctctcttt tatctccagt tctgtcatca tcaccaccac acactgttct gacggttcca   1320
tcctggccat cgccctgctg atcctgttcc tgctcctagc cctggctctc ctctggtggt   1380
tctgccccct ctgctgcact gtgattatca aggaggtccc tccacccccct gccgaggaga   1440
gtgaggaaaa taaaataaaa taacaagaag aagaagaaa gaaatcccac agaaacagat   1500
aacctaacac agcccgtgca acgtatttta tacaatgctc tgaaaatcat agtctcaatc   1560
tagacagtct tttcctctag ttccctgtat tcaaatccca gtgtctaaca ttcaataaat   1620
agctatatga aatcaaaaaa aaaaaaaaaa aaaaaaaaaa aaaaaaa                 1667
```

<210> SEQ ID NO 20
<211> LENGTH: 368
<212> TYPE: PRT
<213> ORGANISM: Homo sapiens

<400> SEQUENCE: 20

```
Met Ala Thr Ala Glu Arg Arg Ala Leu Gly Ile Gly Phe Gln Trp Leu
1               5                   10                  15

Ser Leu Ala Thr Leu Val Leu Ile Cys Ala Gly Gln Gly Gly Arg Arg
            20                  25                  30

Glu Asp Gly Gly Pro Ala Cys Tyr Gly Gly Phe Asp Leu Tyr Phe Ile
        35                  40                  45

Leu Asp Lys Ser Gly Ser Val Leu His His Trp Asn Glu Ile Tyr Tyr
    50                  55                  60

Phe Val Glu Gln Leu Ala His Lys Phe Ile Ser Pro Gln Leu Arg Met
65                  70                  75                  80

Ser Phe Ile Val Phe Ser Thr Arg Gly Thr Thr Leu Met Lys Leu Thr
                85                  90                  95

Glu Asp Arg Glu Gln Ile Arg Gln Gly Leu Glu Glu Leu Gln Lys Val
            100                 105                 110
```

```
Leu Pro Gly Gly Asp Thr Tyr Met His Glu Gly Phe Glu Arg Ala Ser
            115                 120                 125
Glu Gln Ile Tyr Tyr Glu Asn Arg Gln Gly Tyr Arg Thr Ala Ser Val
        130                 135                 140
Ile Ile Ala Leu Thr Asp Gly Glu Leu His Glu Asp Leu Phe Phe Tyr
145                 150                 155                 160
Ser Glu Arg Glu Ala Asn Arg Ser Arg Asp Leu Gly Ala Ile Val Tyr
                165                 170                 175
Cys Val Gly Val Lys Asp Phe Asn Glu Thr Gln Leu Ala Arg Ile Ala
            180                 185                 190
Asp Ser Lys Asp His Val Phe Pro Val Asn Asp Gly Phe Gln Ala Leu
        195                 200                 205
Gln Gly Ile Ile His Ser Ile Leu Lys Lys Ser Cys Ile Glu Ile Leu
    210                 215                 220
Ala Ala Glu Pro Ser Thr Ile Cys Ala Gly Glu Ser Phe Gln Val Val
225                 230                 235                 240
Val Arg Gly Asn Gly Phe Arg His Ala Arg Asn Val Asp Arg Val Leu
                245                 250                 255
Cys Ser Phe Lys Ile Asn Asp Ser Val Thr Leu Asn Glu Lys Pro Phe
            260                 265                 270
Ser Val Glu Asp Thr Tyr Leu Leu Cys Pro Ala Pro Ile Leu Lys Glu
        275                 280                 285
Val Gly Met Lys Ala Ala Leu Gln Val Ser Met Asn Asp Gly Leu Ser
    290                 295                 300
Phe Ile Ser Ser Ser Val Ile Ile Thr Thr Thr His Cys Ser Asp Gly
305                 310                 315                 320
Ser Ile Leu Ala Ile Ala Leu Leu Ile Leu Phe Leu Leu Leu Ala Leu
                325                 330                 335
Ala Leu Leu Trp Trp Phe Trp Pro Leu Cys Cys Thr Val Ile Ile Lys
            340                 345                 350
Glu Val Pro Pro Pro Pro Ala Glu Glu Ser Glu Glu Asn Lys Ile Lys
        355                 360                 365

<210> SEQ ID NO 21
<211> LENGTH: 2360
<212> TYPE: DNA
<213> ORGANISM: Homo sapiens

<400> SEQUENCE: 21
atcatattta aaatctggga caaagaaccg tcgggacgga actccttcca ttgcaaaagc      60
tcggcgcggc ctcgggagct gcccggcggc cccggaccga ggcagccctc ccctttaaaa     120
gaagcggagg acaggattgg gatccttgaa acccgaaacc cagaaacagc atcggagcgg     180
aaaccagagg ggaaaccttg aactcctcca gacaattgct tccggggagt tgcgagggag     240
cgaggggaa taaggacccc gcgaggaagg gcccgcggat ggcgcgtccc tgagggtcgt      300
ggcgagttcg cggagcgtgg gaaggagcgg accctgctct ccccgggctg cgggccatgg     360
ccacggcgga gcggagagcc ctcggcatcg gcttccagtg gctctctttg ccactctgg      420
tgctcatctg cgccgggcaa gggggacgca ggaggatgg gggtccagcc tgctacggcg      480
gatttgacct gtacttcatt ttggacaaat caggaagtgt gctgcaccac tggaatgaaa     540
tctattactt tgtggaacag ttggctcaca aattcatcag cccacagttg agaatgtcct     600
ttattgtttt ctccacccga ggaacaacct taatgaaact gacagaagac agagaacaaa     660
tccgtcaagg cctagaagaa ctccagaaag ttctgccagg aggagacact tacatgcatg     720
```

```
aaggatttga aagggccagt gagcagattt attatgaaaa cagacaaggg tacaggacag     780
ccagcgtcat cattgctttg actgatggag aactccatga agatctcttt ttctattcag     840
agagggaggc taataggtct cgagatcttg gtgcaattgt ttactgtgtt ggtgtgaaag     900
atttcaatga gacacagctg gcccggattg cgacagtaa ggatcatgtg tttcccgtga     960
atgacggctt tcaggctctg caaggcatca tccactcaat tttgaagaag tcctgcatcg    1020
aaattctagc agctgaacca tccaccatat gtgcaggaga gtcatttcaa gttgtcgtga    1080
gaggaaacgg cttccgacat gcccgcaacg tggacagggt cctctgcagc ttcaagatca    1140
atgactcggt cacactcaat gagaagccct tttctgtgga agatacttat ttactgtgtc    1200
cagcgcctat cttaaaagaa gttggcatga agctgcact ccaggtcagc atgaacgatg    1260
gcctctcttt tatctccagt tctgtcatca tcaccaccac acactgtagc ctccacaaaa    1320
ttgcatcagg ccccacaaca gctgcttgca tggaatagca gagaataccg cctgctccct    1380
ccggacagca cactcctgaa aacggggaga gaggagccaa acatgctcgg tttacacttt    1440
ccttatttac tgaatgagtg gagggcagag acaggcctgg agttacgcac actgagtgcc    1500
ccaacatgga agaaacatc aggagggaca ggaaacgttc cctccttaac caacagtttt    1560
caagaccta ctggaggcac tttattggct acataatcac tccatgcggt gggcatcagg    1620
cagaatcctg gtcagaccc aactttgagg tggaggattt cacagtttct ttattttgaa    1680
cttcccccag gctcccacta attcctctcc attctatcct cctcccttc ccacaaaaga    1740
aaacagaaag gagcagcagt gtttgatacc gtatcatcca gaggcctggt tctctcccat    1800
tatagggcaa acaagccctg gcaagatatt tcactcccgc cccatgccat gcattaaaaa    1860
tccaaaattg cctatattcc acctgccaag caagagatgc tttcattatt gaagttccaa    1920
atgtatacct ttgagaacag tgccttctcg tcttaaaaga gaggtcctca ttttgtgagt    1980
tgggagcaga gggaattaaa gaaagccatg atgcagggat ttggccattc aagccgggca    2040
gccttcagag aatgtcatcc ctaatgacac atgcccgaat gaaggagcgg ggctgagctt    2100
gtcctgcctt cgtattgaat gttgcctgtc tgcctcctta atagcgggcc tctgtgtgag    2160
catttgacaa gacttaaaac tattcattga agaaaatgga tgatcccca acaggaagat    2220
gcaaccccat gggctgcctg cttgaccaca gaagtgcttc cagctccagt tgctcatctg    2280
agaactcccc ccaccacttg ctgttaaaat tgttaaaatt aaaggccatg ttgattgatt    2340
ttttaaaaaa aaaaaaaaaa                                                2360
```

<210> SEQ ID NO 22
<211> LENGTH: 333
<212> TYPE: PRT
<213> ORGANISM: Homo sapiens

<400> SEQUENCE: 22

```
Met Ala Thr Ala Glu Arg Arg Ala Leu Gly Ile Gly Phe Gln Trp Leu
 1               5                  10                  15

Ser Leu Ala Thr Leu Val Leu Ile Cys Ala Gly Gln Gly Gly Arg Arg
            20                  25                  30

Glu Asp Gly Gly Pro Ala Cys Tyr Gly Gly Phe Asp Leu Tyr Phe Ile
        35                  40                  45

Leu Asp Lys Ser Gly Ser Val Leu His His Trp Asn Glu Ile Tyr Tyr
    50                  55                  60

Phe Val Glu Gln Leu Ala His Lys Phe Ile Ser Pro Gln Leu Arg Met
65                  70                  75                  80
```

```
Ser Phe Ile Val Phe Ser Thr Arg Gly Thr Thr Leu Met Lys Leu Thr
                85                  90                  95

Glu Asp Arg Glu Gln Ile Arg Gln Gly Leu Glu Glu Leu Gln Lys Val
            100                 105                 110

Leu Pro Gly Gly Asp Thr Tyr Met His Glu Gly Phe Glu Arg Ala Ser
        115                 120                 125

Glu Gln Ile Tyr Tyr Glu Asn Arg Gln Gly Tyr Arg Thr Ala Ser Val
    130                 135                 140

Ile Ile Ala Leu Thr Asp Gly Glu Leu His Glu Asp Leu Phe Phe Tyr
145                 150                 155                 160

Ser Glu Arg Glu Ala Asn Arg Ser Arg Asp Leu Gly Ala Ile Val Tyr
                165                 170                 175

Cys Val Gly Val Lys Asp Phe Asn Glu Thr Gln Leu Ala Arg Ile Ala
                180                 185                 190

Asp Ser Lys Asp His Val Phe Pro Val Asn Asp Gly Phe Gln Ala Leu
        195                 200                 205

Gln Gly Ile Ile His Ser Ile Leu Lys Lys Ser Cys Ile Glu Ile Leu
    210                 215                 220

Ala Ala Glu Pro Ser Thr Ile Cys Ala Gly Glu Ser Phe Gln Val Val
225                 230                 235                 240

Val Arg Gly Asn Gly Phe Arg His Ala Arg Asn Val Asp Arg Val Leu
                245                 250                 255

Cys Ser Phe Lys Ile Asn Asp Ser Val Thr Leu Asn Glu Lys Pro Phe
                260                 265                 270

Ser Val Glu Asp Thr Tyr Leu Leu Cys Pro Ala Pro Ile Leu Lys Glu
        275                 280                 285

Val Gly Met Lys Ala Ala Leu Gln Val Ser Met Asn Asp Gly Leu Ser
290                 295                 300

Phe Ile Ser Ser Ser Val Ile Ile Thr Thr Thr His Cys Ser Leu His
305                 310                 315                 320

Lys Ile Ala Ser Gly Pro Thr Thr Ala Ala Cys Met Glu
                325                 330
```

COMBINATION THERAPIES USING ANTI-METABOLITES AND AGENTS THAT TARGET TUMOR-ASSOCIATED STROMA OR TUMOR CELLS

CROSS-REFERENCE TO RELATED APPLICATIONS

The present application is the National Stage of International Application No. PCT/US2015/034949, filed on Jun. 9, 2015, which claims benefit to U.S. Provisional Application No. 62/009,380, filed on Jun. 9, 2014. The entire contents of the above applications are incorporated by reference as if recited in full herein.

FIELD OF INVENTION

The present invention provides, inter alia, methods for treating or ameliorating the effects of a disease, such as cancer, in a subject. The methods include administering to a subject in need thereof (i) anti-metabolite agents or analogs thereof, and (ii) TEM8 antibodies or antigen binding fragments thereof. Compositions, including pharmaceutical compositions, and kits for treating diseases, such as cancer, are also provided herein.

INCORPORATION BY REFERENCE OF SEQUENCE LISTING

This application contains references to amino acids and/or nucleic acid sequences that have been filed concurrently herewith as sequence listing text file "0385323.txt," file size of 37 KB, created on Jun. 5, 2015. The aforementioned sequence listing is hereby incorporated by reference in its entirety pursuant to 37 C.F.R. § 1.52(e)(5).

BACKGROUND OF THE INVENTION

Targeting tumor-associated stroma, especially tumor associated vasculature, is considered a promising approach to cancer therapy. Various classes of chemotherapeutics directed toward tumor vasculature have been developed, including anti-angiogenic agents and vascular disrupting agents, the former affecting neovascularization and the latter targeting existing blood vessels that supply tumors with nutrients and oxygen. Though these therapies are widely used, particularly in cases of metastatic cancer, they are hampered by their toxicity and off-target effects against healthy vasculature. Thus, there exists, inter alia, a need for additional therapeutics that are less toxic and work in combination with current agents to suppress tumor growth by targeting the tumor-associated stroma or the tumor cells themselves. The present invention is directed to meeting these and other needs.

SUMMARY OF THE INVENTION

One embodiment of the present invention is a method for treating or ameliorating the effects of a disease in a subject. The method comprises:
administering to a subject in need thereof
(a) a therapeutically effective amount of an anti-metabolite agent or analog thereof; and
(b) a therapeutically effective amount of a monoclonal antibody or antigen binding fragment thereof, wherein the monoclonal antibody comprises:
(i) a heavy chain variable region (VH), which comprises an amino acid sequence selected from the group consisting of SEQ ID NO:1, SEQ ID NO:3, SEQ ID NO:5, and SEQ ID NO:7; and
(ii) a light chain variable region (VL), which comprises an amino acid sequence selected from the group consisting of SEQ ID NO:2, SEQ ID NO:4, SEQ ID NO:6, and SEQ ID NO:8.

Another embodiment of the present invention is a method for treating or ameliorating the effects of a disease in a subject. The method comprises:
administering to a subject in need thereof
(a) a therapeutically effective amount of an anti-metabolite agent or analog thereof; and
(b) a therapeutically effective amount of a monoclonal antibody or antigen binding fragment thereof, wherein the monoclonal antibody comprises:
(i) a heavy chain variable region, which comprises an amino acid sequence selected from SEQ ID NO:5; and
(ii) a light chain variable region, which comprises an amino acid sequence selected from SEQ ID NO:6.

A further embodiment of the present invention is a method for treating or ameliorating the effects of a disease in a subject. The method comprises:
administering to a subject in need thereof
(a) a therapeutically effective amount of 5-fluorouracil; and
(b) a therapeutically effective amount of a monoclonal antibody or antigen binding fragment thereof, wherein the monoclonal antibody comprises:
(i) a heavy chain variable region, which comprises an amino acid sequence selected from SEQ ID NO:5; and
(ii) a light chain variable region, which comprises an amino acid sequence selected from SEQ ID NO:6.

An additional embodiment of the present invention is a composition for treating or ameliorating the effects of a disease in a subject. The composition comprises:
(a) a therapeutically effective amount of an anti-metabolite agent or analog thereof; and
(b) a therapeutically effective amount of a monoclonal antibody or antigen binding fragment thereof, wherein the monoclonal antibody comprises:
(i) a heavy chain variable region (VH), which comprises an amino acid sequence selected from the group consisting of SEQ ID NO:1, SEQ ID NO:3, SEQ ID NO:5, and SEQ ID NO:7; and
(ii) a light chain variable region (VL), which comprises an amino acid sequence selected from the group consisting of SEQ ID NO:2, SEQ ID NO:4, SEQ ID NO:6, and SEQ ID NO:8.

Another embodiment of the present invention is a composition for treating or ameliorating the effects of a disease in a subject. The composition comprises:
(a) a therapeutically effective amount of an anti-metabolite agent or analog thereof; and
(b) a therapeutically effective amount of a monoclonal antibody or antigen binding fragment thereof, wherein the monoclonal antibody comprises:
(i) a heavy chain variable region, which comprises an amino acid sequence selected from SEQ ID NO:5; and
(ii) a light chain variable region, which comprises an amino acid sequence selected from SEQ ID NO:6.

A further embodiment of the present invention is a composition for treating or ameliorating the effects of a disease in a subject. The composition comprises:
(a) a therapeutically effective amount of 5-fluorouracil; and (b) a therapeutically effective amount of a monoclonal antibody or antigen binding fragment thereof, wherein the monoclonal antibody comprises:
  (i) a heavy chain variable region, which comprises an amino acid sequence selected from SEQ ID NO:5; and
  (ii) a light chain variable region, which comprises an amino acid sequence selected from SEQ ID NO:6.

An additional embodiment of the present invention is a pharmaceutical composition. The pharmaceutical composition comprises any of the compositions disclosed herein and a pharmaceutically acceptable diluent or carrier.

Another embodiment of the present invention is a kit. The kit comprises any of the compositions or pharmaceutical compositions disclosed herein packaged together with instructions for its use.

BRIEF DESCRIPTION OF THE DRAWINGS

FIG. 1A shows a box plot of group median tumor volume distribution on day 21. FIG. 1B shows mean tumor growth over the time course of the study. FIG. 1C shows individual times to the endpoint for each mouse in the study. FIG. 1D shows percent body weight change for each group over the course of the study.

FIG. 6A shows a time course of mean tumor growth throughout the study. FIG. 6B shows a Kaplan-Meier survival plot. FIG. 6C shows individual times to endpoint for mice in each group. FIG. 6D shows percent body weight change for each group throughout the study.

FIG. 7A shows a time course of mean tumor growth throughout the study. FIG. 7B shows the time course with median tumor growth of each group. FIG. 7C shows a Kaplan-Meier survival plot. FIG. 7D shows individual times to endpoint for mice in each group. FIG. 7E shows percent body weight change for each group throughout the study.

FIGS. 11A-B show the effect of M825 on 3T3 fibroblasts in the presence of TGFb-1. FIG. 11A shows pictures of the cultured cells over 48 hours and FIG. 11B is a bar graph quantifying the lattice area of the cells.

FIGS. 12A-B show the effect of M830 Fc mutation on antibody-dependent cell-mediated cytotoxicity (ADCC). FIG. 12A is a schematic showing the antibody binding in the ADCC assay and FIG. 12B is a line graph demonstrating that the Fc mutant form of M830 has significantly enhanced binding to FcγRIIIa (CD16a).

DETAILED DESCRIPTION OF THE INVENTION

Figure 1:
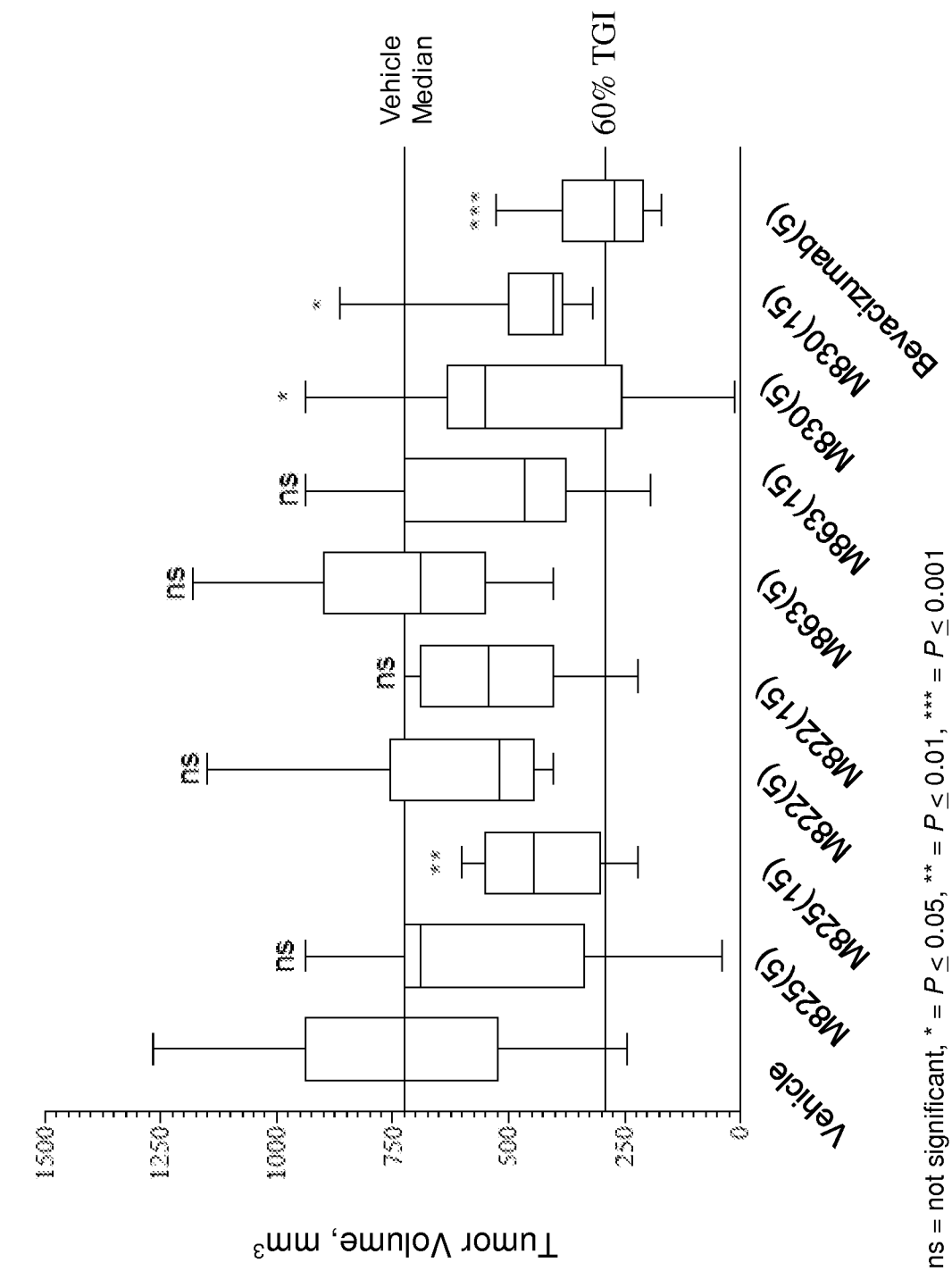
FIGS. 1A-D show results from an efficacy study of TEM8 antibodies in a HCT116 colorectal carcinoma xenograft model. Treatment was initiated when tumor volumes were approximately 60-80 mm$^3$. TEM 8 antibody (hIgG1) was dosed at 5 and 15 mg/kg, three times per week for three weeks. Bevacizumab was dosed at 5 mg/kg, two times per week for three weeks.
Figure 1:
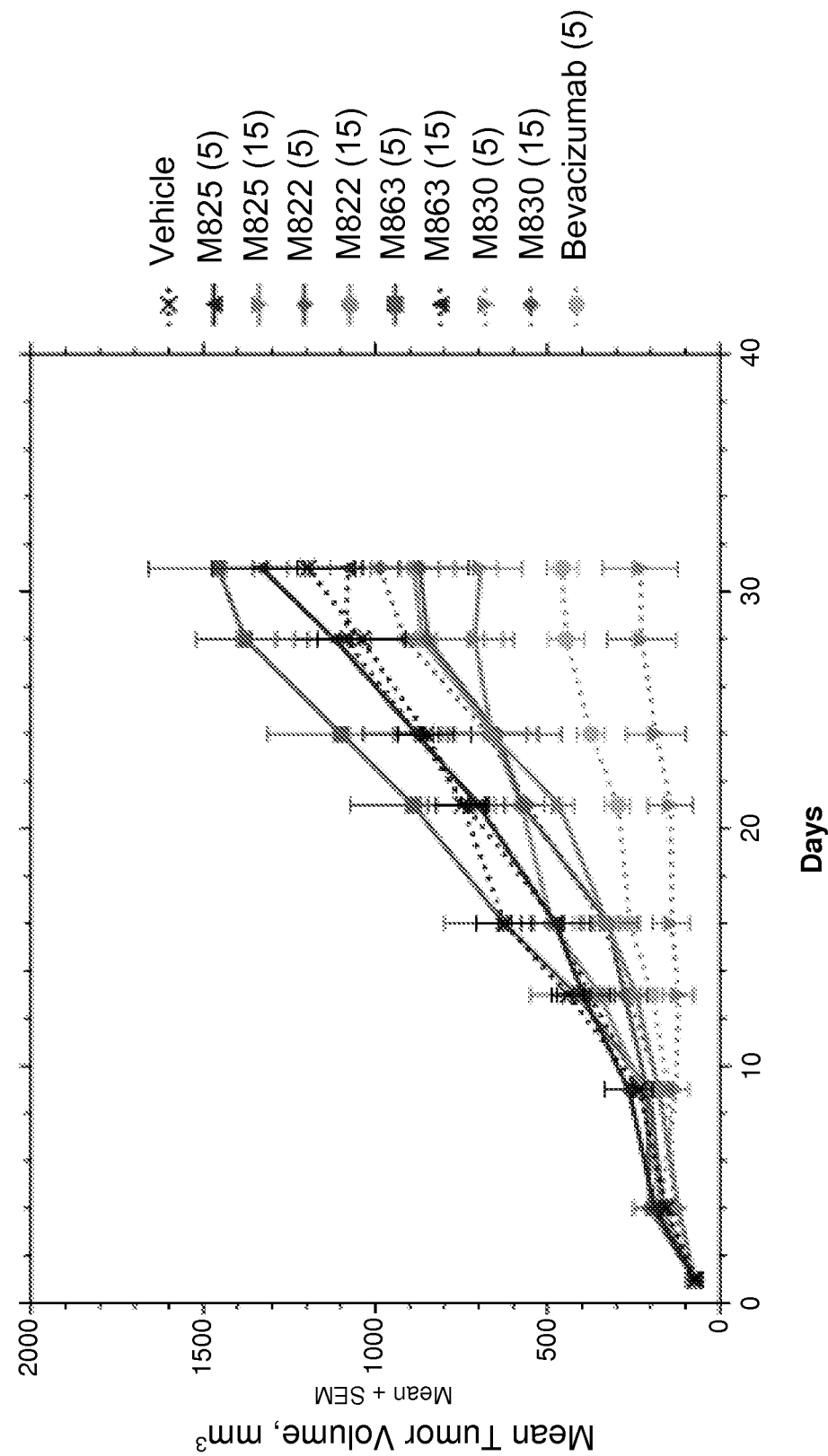
Figure 1:
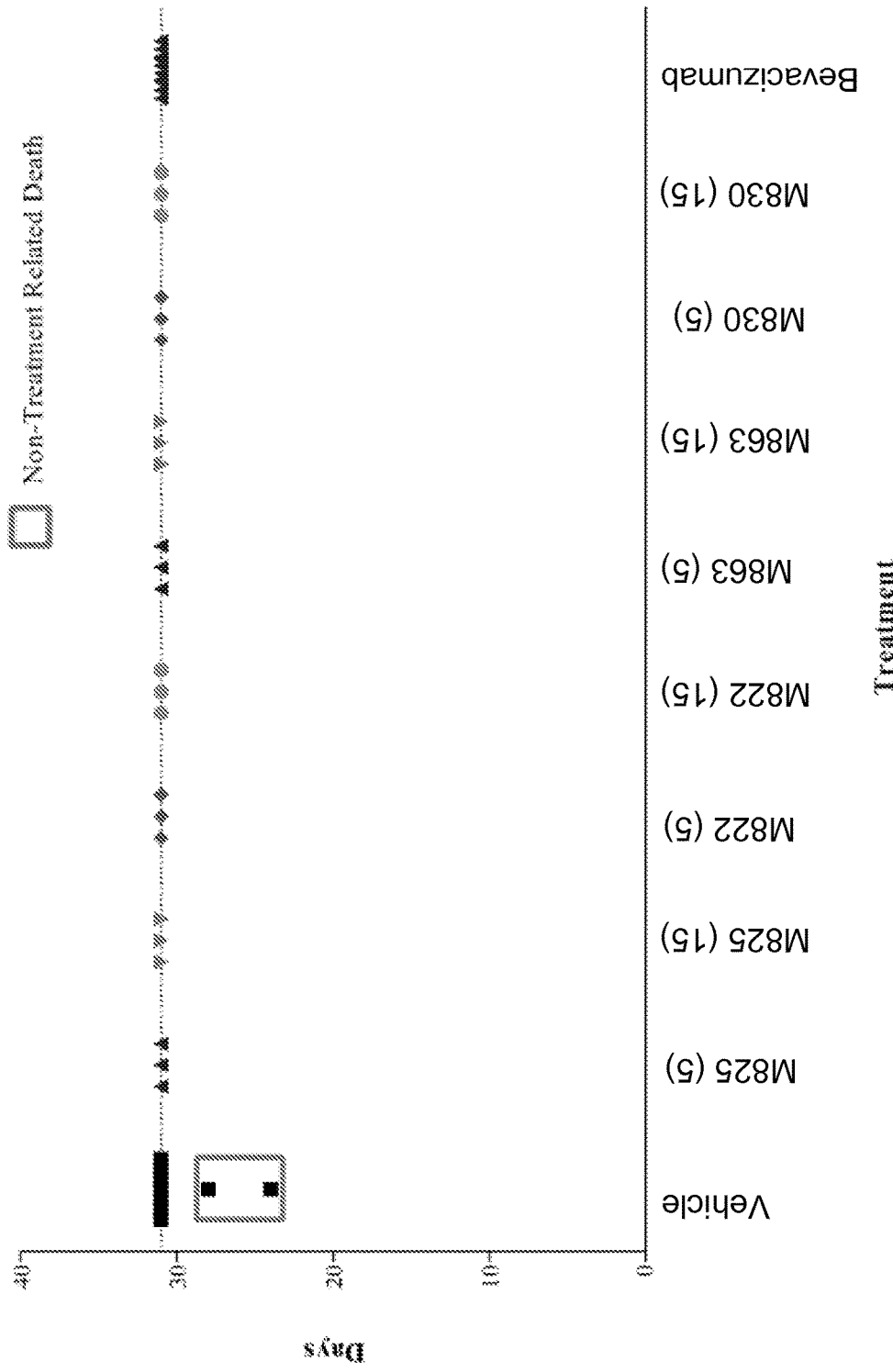
Figure 1:
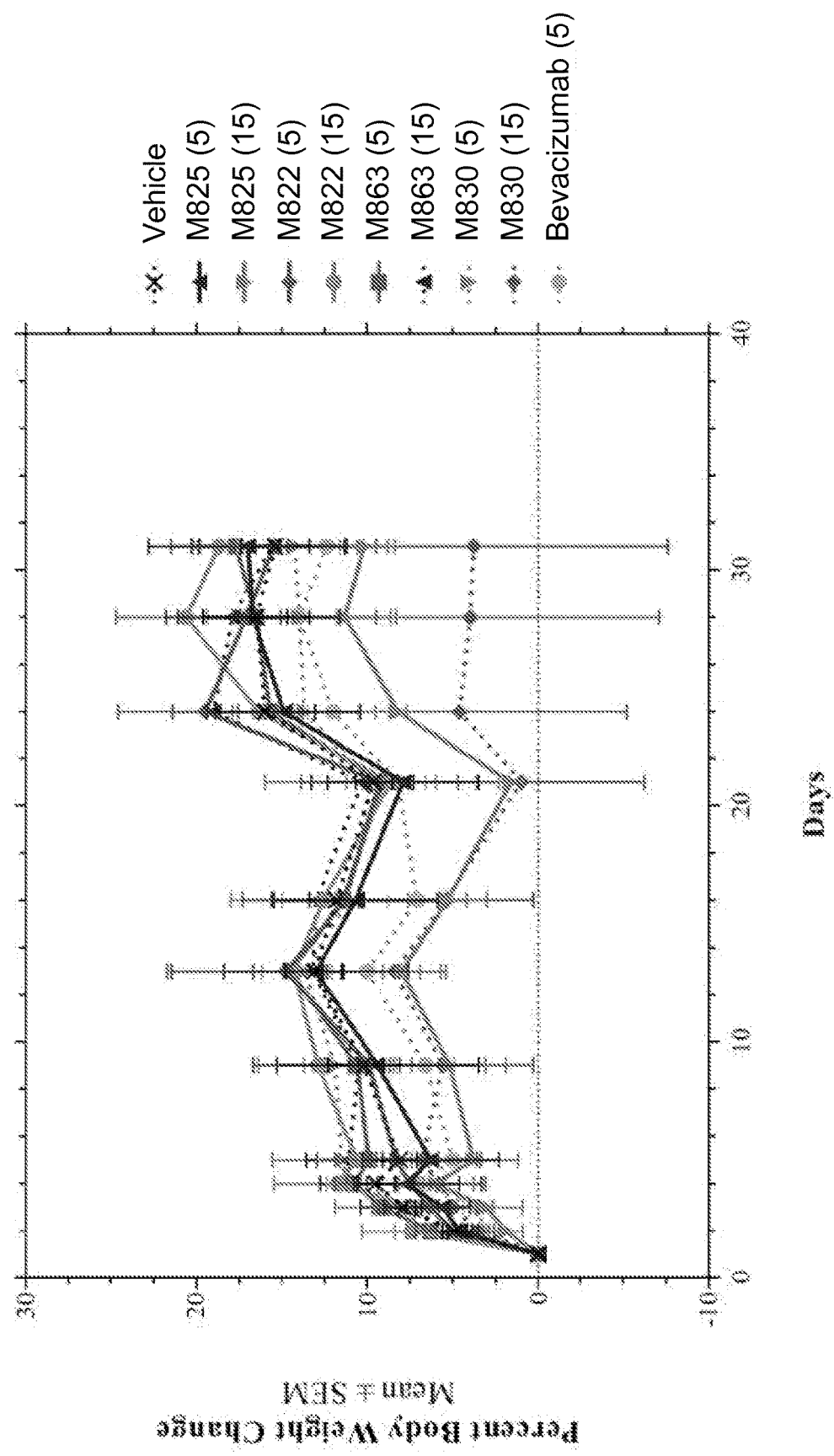

One embodiment of the present invention is a method for treating or ameliorating the effects of a disease in a subject. The method comprises:
  administering to a subject in need thereof
  (a) a therapeutically effective amount of an anti-metabolite agent or analog thereof; and
  (b) a therapeutically effective amount of a monoclonal antibody or antigen binding fragment thereof, wherein the monoclonal antibody comprises:
    (i) a heavy chain variable region (VH), which comprises an amino acid sequence selected from the group consisting of SEQ ID NO:1, SEQ ID NO:3, SEQ ID NO:5, and SEQ ID NO:7; and
    (ii) a light chain variable region (VL), which comprises an amino acid sequence selected from the group consisting of SEQ ID NO:2, SEQ ID NO:4, SEQ ID NO:6, and SEQ ID NO:8.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

As used herein, the terms "ameliorate", "ameliorating" and grammatical variations thereof mean to decrease the severity of the symptoms of a disease in a subject.

As used herein, a "subject" is a mammal, preferably, a human. In addition to humans, categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc.

In the present invention, cyclooxygenase-2 (COX-2) inhibitors (COXIBs), non-steroidal anti-inflammatory drugs (NSAIDs), and/or prostaglandin E2 (PGE2) synthase inhibitors may be administered to the subject in addition to or as a replacement for the anti-metabolite agent. COXIBs according to the present invention include, but are not limited to, AAT-076 (AskAt), celecoxib (Pfizer), valdecoxib (Pfizer), rofecoxib (Merck), nimesulide, 4-hydroxynimesulide, flosulide, L475L337, bromfenac (InSite Vision), KIT-302 (Kitov), polmacoxib (Pacificpharma), etodolac (Pfizer), parecoxib sodium (Pfizer), etoricoxib (Merck), lumiracoxib (Novartis), VA-964 (Rottapharm Madaus), iguratimod (Toyama), and meloxicam (Boehringer Ingelheim). NSAIDs according to the present invention include, but are not limited to, diclofenac (Novartis), diflunisal (Merck), etodolac (Almirall Limited), fenoprofen (Ranbaxy Pharmaceuticals), flurbiprofen (Pfizer), ibuprofen (Pfizer), indomethacin (Lundbeck, Inc.), ketoprofen (Wyeth), ketorolac (Hospira), mefenamic acid (Shionogi, Inc.), meloxicam (Abbott Laboratories), nabumetone (GlaxoSmithKline), naproxen (Bayer), oxaprozin (Pfizer), piroxicam (Pfizer), sulindac (Mutual Pharmaceutical Company, Inc.), AAT-076 (AskAt), carbasalate calcium (Bristol-Myers Squibb), rimazolium metilsulfate (Chinoin), isonixin (Hermes), lysine clonixinate (Laplex), alminoprofen (Recordati), lornoxicam (Takeda), fosfosal (Uriach), nepafenac (Novartis), diclofenac (Novartis), and tolmetin (Ortho-McNeil-Janssen Pharmaceuticals, Inc.). PGE2 synthase inhibitors according to the present invention include, but are not limited to, NS-398, sulindac sulphide, leukotriene C4, GRC-27864 (Glenmark), OX-MPI (Orexo), PF-04693627 (Pfizer), and those described in, for example, He, et al, 2013.

As used herein, an "anti-metabolite agent" is a substance that reduces or inhibits a cell's use of a chemical that is part of normal metabolism. As used herein, an "analog" is a compound that is structurally similar to, e.g., the anti-metabolite agent, and that also reduces or inhibits the growth of cancer cells. Non-limiting examples of anti-metabolite agents or analogs thereof according to the present invention include antifolates, purine inhibitors, pyrimidine inhibitors, and combinations thereof.

As used herein, an "antifolate" is a substance that alters, reduces, or inhibits the use of folic acid (vitamin $B_9$) by cells. Non-limiting examples of antifolates include methotrexate (DuraMed Pharmaceuticals, Inc.), pemetrexed (Eli Lilly), pralatrexate (Spectrum Pharmaceuticals), aminopterin (Sigma Aldrich), pharmaceutically acceptable salts thereof, and combinations thereof.

As used herein, a "purine" is a compound that contains a fused six-membered and a five-membered nitrogen-containing ring. Non-limiting examples of purines that are important for cellular metabolism include adenine, guanine, hypoxanthine, and xanthine. A "purine inhibitor" is a substance that alters, reduces or suppresses the production of a purine or the use of a purine by a cell. Non-limiting examples of purine inhibitors include methotrexate (DuraMed Pharmaceuticals, Inc.), pemetrexed (Eli Lilly), hydroxyurea (Bristol-Myers Squibb), 2-mercaptopurine (Sigma-Aldrich), 6-mercaptopurine (Sigma-Aldrich), fludarabine (Ben Venue Laboratories), clofarabine (Genzyme Corp.), nelarabine (GlaxoSmithKline), pralatrexate (Spectrum Pharmaceuticals), 6-thioguanine (Gate Pharmaceuticals), forodesine (BioCryst Pharmaceuticals), pentostatin (Bedford Laboratories), sapacitabine (Cyclacel Pharmaceuticals, Inc.), aminopterin (Sigma Aldrich), azathioprine (GlaxoSmithKline), pharmaceutically acceptable salts thereof, and combinations thereof.

As used herein, a "pyrimidine" is a compound that contains a six-membered nitrogen-containing ring. Non-limiting examples of pyrimidines that are important for cellular metabolism include uracil, thymine, cytosine, and orotic acid. A "pyrimidine inhibitor" is a substance that alters, reduces, or suppresses the production of a pyrimidine or the use of a pyrimidine by the a cell. Non-limiting examples of pyrimidine inhibitors include 5-fluorouracil (Tocris Bioscience), tegafur (LGM Pharma), capecitabine (Xeloda) (Roche), cladribine (LGM Pharma), gemcitabine (Eli Lilly), cytarabine (Bedford Laboratories), decitabine (Eisai Inc.), floxuridine (Bedford Laboratories), 5-azacytidine (Pharmion Pharmaceuticals), doxifluridine (Cayman Chemicals), thiarabine (Access Pharmaceuticals), troxacitabine (SGX Pharmaceuticals), raltitrexed (AstraZeneca), carmofur (Santa Cruz Biotechnology, Inc.), 6-azauracil (MP Biomedicals, LLC), pharmaceutically acceptable salts thereof, and combinations thereof.

In a preferred aspect of the present invention, the anti-metabolite agent or an analog thereof is selected from the group consisting of 5-fluorouracil (Tocris Bioscience), tegafur (LGM Pharma), capecitabine (Xeloda) (Roche), cladribine (LGM Pharma), methotrexate (DuraMed Pharmaceuticals, Inc.), pemetrexed (Eli Lilly), hydroxyurea (Bristol-Myers Squibb), 2-mercaptopurine (Sigma-Aldrich), 6-mercaptopurine (Sigma-Aldrich), fludarabine (Ben Venue Laboratories), gemcitabine (Eli Lilly), clofarabine (Genzyme Corp.), cytarabine (Bedford Laboratories), decitabine (Eisai Inc.), floxuridine (Bedford Laboratories), nelarabine (GlaxoSmithKline), pralatrexate (Spectrum Pharmaceuticals), 6-thioguanine (Gate Pharmaceuticals), 5-azacytidine (Pharmion Pharmaceuticals), doxifluridine (Cayman Chemicals), forodesine (BioCryst Pharmaceuticals), pentostatin (Bedford Laboratories), sapacitabine (Cyclacel Pharmaceuticals, Inc.), thiarabine (Access Pharmaceuticals), troxacitabine (SGX Pharmaceuticals), raltitrexed (AstraZeneca), aminopterin (Sigma Aldrich), carmofur (Santa Cruz Biotechnology, Inc.), azathioprine (GlaxoSmithKline), 6-azauracil (MP Biomedicals, LLC), pharmaceutically acceptable salts thereof, and combinations thereof.

As used herein, an "antibody" and "antigen-binding fragments thereof" encompass naturally occurring immunoglobulins (e.g., IgM, IgG, IgD, IgA, IgE, etc.) as well as non-naturally occurring immunoglobulins, including, for example, single chain antibodies, chimeric antibodies (e.g., humanized murine antibodies), heteroconjugate antibodies (e.g., bispecific antibodies), Fab', F(ab')$_2$, Fab, Fv, and rIgG. See, e.g., Pierce Catalog and Handbook, 1994-1995 (Pierce Chemical Co., Rockford, Ill.); Kuby et al., 1998. As used herein, an "antigen-binding fragment" is a portion of the full length antibody that retains the ability to specifically recognize the antigen, as well as various combinations of such portions.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

Full length antibodies can be proteolytically digested down to several discrete, functional antibody fragments, which retain the ability to recognize the antigen. For example, the enzyme papain can be used to cleave a full length immunoglobulin into two Fab fragments and an Fc fragment. Thus, the Fab fragment is typically composed of two variable domains and two constant domains from the heavy and light chains. The Fv region is usually recognized as a component of the Fab region and typically comprises two variable domains, one from each of the heavy ($V_H$, "heavy chain variable region", as used herein) and light ($V_L$, "light chain variable region", as used herein) chains. The enzyme pepsin cleaves below the hinge region, so a $F(ab')_2$ fragment and a pFc' fragment is formed. $F(ab')_2$ fragments are intact antibodies that have been digested, removing the constant (Fc) region. Two Fab' fragments can then result from further digestion of $F(ab')_2$ fragments. Examples of antigen-binding fragments include, but are not limited to, Fv, Fab, Fab', Fab'-SH, $F(ab')_2$, diabodies, tribodies, scFvs, and single-domain antibodies (dAbs).

Typically, a full length antibody has at least one heavy and at least one light chain. Each heavy chain contains a variable domain ($V_H$) and typically three or more constant domains ($C_H1$, $C_H2$, $C_H3$, etc.), while each light chain contains a variable domain ($V_L$) and a constant domain $C_L$. Light and heavy chain variable regions contain four "framework" regions interrupted by three hypervariable regions, also called "complementarity-determining regions" or "CDRs". The extent of the framework regions and CDRs have been defined. See, e.g., Kabat et al., U.S. Dept. of Health and Human Services, Sequences of Proteins of Immunological Interest (1983) and Chothia et al., J. Mol. Biol. 196:901-917 (1987). The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody, whereas a $V_L$ CDR1 is the CDR1 from the variable domain of the light chain of the antibody.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made, e.g., by the hybridoma method first described by Kohler et al., Nature 256: 495 (1975), and as modified by the somatic hybridization method as set forth above; or may be made by other recombinant DNA methods (see, e.g., U.S. Pat. No. 4,816,567).

Additional types of antibodies that may be part of the monoclonal antibodies of the present invention include, but are not limited to, chimeric, humanized, and human antibodies. For application in man, it is often desirable to reduce immunogenicity of antibodies originally derived from other species, like mouse. This can be done by construction of chimeric antibodies, or by a process called "humanization". In this context, a "chimeric antibody" is understood to be an antibody comprising a domain (e.g. a variable domain) derived from one species (e.g. mouse) fused to a domain (e.g. the constant domains) derived from a different species (e.g. human).

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the framework (FR) regions are those of a human immunoglobulin sequence. The humanized antibody optionally also will comprise at least a portion of an immunoglobulin constant region (Fc), typically that of a human immunoglobulin (Jones et al., Nature 321:522-525 (1986); Riechmann et al., Nature 332:323-329 (1988); and Presta, Curr. Op. Struct. Biol 2:593-596 (1992)). Humanization can be essentially performed, e.g., following the method of Winter and co-workers (Jones et al., Nature 321:522-525 (1986); Riechmann et al., Nature 332:323-3'27 (1988); Verhoeyen et al., Science 239:1534-1536 (1988)), by substituting rodent CDRs or CDR sequences for the corresponding sequences of a human antibody.

Furthermore, technologies have been developed for creating antibodies based on sequences derived from the human genome, for example by phage display or using transgenic animals (see, e.g., WO 90/05144; D. Marks, H. R. Hoogenboom, T. P. Bonnert, J. McCafferty, A. D. Griffiths and G. Winter (1991) "By-passing immunisation. Human antibodies from V-gene libraries displayed on phage." J. Mol. Biol., 222, 581-597; Knappik et al., J. Mol. Biol. 296: 57-86, 2000; S. Carmen and L. Jermutus, "Concepts in antibody phage display". Briefings in Functional Genomics and Proteomics 2002 1(2):189-203; Lonberg N, Huszar D. "Human antibodies from transgenic mice". Int Rev Immunol. 1995; 13(1):65-93; Bruggemann M, Taussig M J. "Production of human antibody repertoires in transgenic mice". Curr Opin Biotechnol. 1997 August; 8(4):455-8.). Such antibodies are "human antibodies" in the context of the present invention.

As used herein, a "recombinant" antibody is any antibody whose production involves expression of a non-native DNA sequence encoding the desired antibody structure in an organism. In the present invention, recombinant antibodies include tandem scFv (taFv or $scFv_2$), diabody, $dAb_2/VHH_2$, knob-into-holes derivatives, SEED-IgG, heteroFc-scFv, Fab-scFv, scFv-Jun/Fos, Fab'-Jun/Fos, tribody, DNL-$F(ab)_3$, $scFv_3$-CH1/CL, Fab-$scFv_2$, IgG-scFab, IgG-scFv, scFv-IgG, $scFv_2$-Fc, $F(ab')_2$-$scFv_2$, scDB-Fc, scDb-CH3, Db-Fc, $scFv_2$-H/L, DVD-Ig, tandAb, scFv-dhlx-scFv, $dAb_2$-IgG, dAb-IgG, dAb-Fc-dAb, and combinations thereof.

Variable regions of antibodies are typically isolated as single-chain Fv (scFv) or Fab fragments. ScFv fragments are composed of $V_H$ and $V_L$ domains linked by a short 10-25 amino acid linker. Once isolated, scFv fragments can be genetically linked with a flexible peptide linker such as, for example, one or more repeats of Ala-Ala-Ala, Gly-Gly-Gly-Gly-Ser, etc. The resultant peptide, a tandem scFv (taFv or scFv$_2$) can be arranged in various ways, with V$_H$-V$_L$ or V$_L$-V$_H$ ordering for each scFv of the taFv. (Kontermann, R. E. In: Bispecific Antibodies. Kontermann R E (ed.), Springer Heidelberg Dordrecht London New York, pp. 1-28 (2011)).

As used herein, the term "epitope" refers to the portion of the antigen which is recognized by the antibody or antigen binding fragment. A single antigen (such as an antigenic polypeptide) may have more than one epitope. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. Epitopes formed from contiguous amino acids are typically retained on exposure to denaturing solvents, whereas epitopes formed by tertiary folding are typically lost on treatment with denaturing solvents.

Portions of the preferred antibodies and nucleic acids encoding said antibody portions of the present invention are listed below in Table 1.

TABLE 1

Antibody Sequences

| SEQ ID NO. | Sequence Name | Nucleic Acid/ Polypeptide | Organism |
|---|---|---|---|
| 1 | M825 mAb VH | Polypeptide | Artificial sequence |
| 2 | M825 mAb VL | Polypeptide | Artificial sequence |
| 3 | M822 mAb VH | Polypeptide | Artificial sequence |
| 4 | M822 mAb VL | Polypeptide | Artificial sequence |
| 5 | M830 mAb VH | Polypeptide | Artificial sequence |
| 6 | M830 mAb VL | Polypeptide | Artificial sequence |
| 7 | M863 mAb VH | Polypeptide | Artificial sequence |
| 8 | M863 mAb VL | Polypeptide | Artificial sequence |
| 11 | M825 mAb VH cDNA | Nucleic acid | Artificial sequence |
| 12 | M825 mAb VL cDNA | Nucleic acid | Artificial sequence |
| 13 | M822 mAb VH cDNA | Nucleic acid | Artificial sequence |
| 14 | M822 mAb VL cDNA | Nucleic acid | Artificial sequence |
| 15 | M830 mAb VH cDNA | Nucleic acid | Artificial sequence |
| 16 | M830 mAb VL cDNA | Nucleic acid | Artificial sequence |
| 17 | M863 mAb VH cDNA | Nucleic acid | Artificial sequence |
| 18 | M863 mAb VL cDNA | Nucleic acid | Artificial sequence |

In one aspect of this embodiment, the disease is characterized by differential expression of a tumor endothelial marker 8 (TEM8) membrane antigen. As used herein, the terms "differential expression", "differentially expressed", and grammatical variations thereof mean changes in the production levels of certain mRNA(s) and/or protein(s) in tumor cells relative to normal cells. Differential expression includes upregulation and downregulation of gene(s). Preferably, the differential expression of TEM8 on, e.g. tumor endothelial cells, is sufficient for the antibodies and/or antigen binding fragments thereof of the present invention to specifically target such cells, leaving normal, non-cancerous tissue substantially untouched.

Representative human TEM8 nucleic acid and polypeptide sequences are shown in Table 2 below.

TABLE 2

TEM8 Sequences

| SEQ ID NO. | Sequence Name | Nucleic Acid/Polypeptide | Organism | Other Information |
|---|---|---|---|---|
| 9 | TEM8 mRNA | Nucleic acid | Homo sapiens | Transcript variant 1 |
| 10 | TEM8 protein | Polypeptide | Homo sapiens | Isoform 1 precursor |
| 19 | TEM8 mRNA | Nucleic acid | Homo sapiens | Transcript variant 2 |
| 20 | TEM8 protein | Polypeptide | Homo sapiens | Isoform 2 precursor |
| 21 | TEM8 mRNA | Nucleic acid | Homo sapiens | Transcript variant 3 |
| 22 | TEM8 protein | Polypeptide | Homo sapiens | Isoform 3 precursor |

In another aspect of the invention, the disease is characterized by differential expression of tumor endothelial marker 8 (TEM8) membrane antigen on a tumor cell and/or a tumor stromal cell. As used herein, "tumor cells" comprise cells that have abnormal growth or division. As used herein, "tumors" and "cancers" are used interchangeably. Tumors may be benign or malignant. "Tumor stromal cells" include those cells that are in a tumor cell's microenvironment and support the growth of tumor cells. Tumor vasculature is distinct from normal vasculature in that several genes are differentially expressed in tumor-associated blood vessels (St. Croix et al., 2000). One of these genes, tumor endothelial marker 8 (TEM8) membrane antigen, is upregulated in the vasculature of malignant solid tumors, with limited expression in healthy tissues.

In another preferred embodiment, the disease is a cancer that differentially expresses TEM8. More preferably, the cancer is selected from the group consisting of kidney cancer, colon cancer, lung cancer, liposarcomas, brain cancer, breast cancer, melanoma, liver cancer, head and neck cancer, and prostate cancer.

In another aspect of this embodiment, the monoclonal antibody or antigen binding fragment thereof comprises:

(1) a VH polypeptide encoded by:

(SEQ ID NO: 11)
caggtccagctggtgcagtctggggctgaggtgaagaagcctgggacctc agtgaaggtctcctgcaaggttcctggatacaccttcagcagctatgcta tcagctgggtgcgacaggcccctggacaagggcttgagtggatgggaggg atcatccctatctttggtacaacaaactacgcacagaagttccagggcag agtcacgattaccggggaggaatccacgagcacagtctacatggagctga gcagcctgagatctgaggacacggccgtgtattactgtgcgagagatacg gactacatgtttgactactggggccagggaaccctggtcaccgtgagctc a and (2) a VL polypeptide encoded by:

(SEQ ID NO: 12)
tcttctgagctgactcaggaccctgttgtgtctgtggccttgggagagac agtcagtatcacatgccaaggagacaacctcagagacttttatgcaagct ggtaccaacagaagccaggacaggcccctctactagtcatgtatggtaaa

```
aacaggcggccctcagggatcccagaccgattctctggctccacctcagg aaacacactttccttgaccatcactggggctcaggcggaagatgaggctg actattactgtagctcccgggacaacagtaagcatgtggtgttcggcggg gggaccaaggtcaccgtccta.
```

In a further aspect of this embodiment, the monoclonal antibody or antigen binding fragment thereof comprises:
(1) a VH polypeptide encoded by:

(SEQ ID NO: 13)
```
caggtccagctggtgcagtctggggctgaggtgaagaagcctgggc ctcagtgaaggtctcctgcaaggtttctggatacaccttcagcagct atgctatcagctgggtgcgacaggcccctggacaagggcttgagtgg atgggagggatcatccctatctttggtacagcaaactacgcacagaa gttccagggcagagtcacgattaccgcggacgaatccacgagcacag cctacatggagctgagcagcctgagatctgaggacacggccgtgtat tactgtgcgagagatacggactacatgtttgactactggggccaggg aaccctggtcaccgtgagctca
```
and
(2) a VL polypeptide encoded by:

(SEQ ID NO: 14)
```
tcttctgagctgactcaggaccctgttgtgtctgtggccttgggaga gacagtcagtatcacatgccaaggagacaacctcagagactttatg caagctggtaccaacagaagccaggacaggcccctctactagtcatg tatggtaaaaacaggcggccctcagggatcccagaccgattctctgg ctccacctcaggaaacacactttccttgaccatcactggggctcagg cggaagatgaggctgactattactgtagctcccgggacaacagtaag catgtggtgttcggcggggggaccaaggtcaccgtccta.
```

In an additional aspect of this embodiment, the monoclonal antibody or antigen binding fragment thereof comprises:
(1) a VH polypeptide encoded by:

(SEQ ID NO: 15)
```
gaggtgcagctggtggagtctgggggaggcgtggtccagcctgggag gtccgtgagactctcctgtgcagcctctggattcaccttcagtacct atactatgcactgggtccgccaggctccaggcaaggggctggagtgg gtggcaattatctcaaatgatggaagcaataagtactacgcagacc cgtgaggggccgattcaccatctccagagacaattccaagaacacgc tgtatctgcaaatgaacagcctgagagctgaggacacggctgtgtat tactgtgtacgtggcagcagctggtatcgcggaaattggttcgaccc ctggggccagggaaccctggtcaccgtgagctca
```
and
(2) a VL polypeptide encoded by:

(SEQ ID NO: 16)
```
gacatccagatgacccagtctccatcctccctgtctgcatctgtagg agacagagtcaccatcgcttgccgggcaagtcagaccattagtaggt
```

```
atttaaattggtatcagcagaaaccagggaaagcccctaagctcctg atctatgctgcatccagtttgcaaagtggggtctcatcaaggttcag tggcagtggatctgggacagagttcactctcaccatcagcagtctgc agcctgaagattttgcaacttatttctgtcaacagacttacagtccc ccgatcaccttcggccaagggacacgactggagattaaacga.
```

In another aspect of this embodiment, the monoclonal antibody or antigen binding fragment thereof comprises:
(1) a VH polypeptide encoded by:

(SEQ ID NO: 17)
```
gaggtgcagctggtggagaccggggctgaggtgaagaagcctgggc ctcagtgaaggtctcctgcaaggcttctggatacaccttcaccggct actatatgcactgggtgcgacaggcccctggacaagggcttgagtgg atgggatggatcaaccctaccagtggtagcacaaactatgcacagaa gtttcagggcagggtcaccatgaccagggacacgtccatcagcacag cctacatggagctgagcgggctgagatctgacgacactgccgtgtat tactgtgtgagagatccgggttctcctaagtggctggccttcgaccc ctggggccagggcaccctggtcaccgtgagctca
```
(2) a VL polypeptide encoded by:

(SEQ ID NO: 18)
```
gacatccagttgacccagtctccatcctccttgtctgcttctgtagg agacagagtcaccatcacttgccgggcaagtcgggccattagtaggt atttaaattggtatcagcagaaaccagggaaagcccctaagctcctg atctatgctgcatccagtttgcaaagtggggtctcatcaaggttcag tggcagtggatctgggacagagttcactctcaccatcagcagtctgc agcctgaagattttgcaacttatttctgtcaacagacttacagtccc ccgatcaccttcggccaagggacacgactggagattaaacgt.
```

Another embodiment of the present invention is a method for treating or ameliorating the effects of a disease in a subject. The method comprises:
administering to a subject in need thereof
(a) a therapeutically effective amount of an anti-metabolite agent or analog thereof; and
(b) a therapeutically effective amount of a monoclonal antibody or antigen binding fragment thereof, wherein the monoclonal antibody comprises:
(i) a heavy chain variable region, which comprises an amino acid sequence selected from SEQ ID NO:5; and
(ii) a light chain variable region, which comprises an amino acid sequence selected from SEQ ID NO:6.

Suitable and preferred anti-metabolite agents or analogs thereof, subjects, and diseases (including the characteristics of the diseases and various types of cancers) are as disclosed herein.

A further embodiment of the present invention is a method for treating or ameliorating the effects of a disease in a subject. The method comprises:
administering to a subject in need thereof
(a) a therapeutically effective amount of 5-fluorouracil; and (b) a therapeutically effective amount of a monoclonal antibody or antigen binding fragment thereof, wherein the monoclonal antibody comprises:
  (i) a heavy chain variable region, which comprises an amino acid sequence selected from SEQ ID NO:5; and
  (ii) a light chain variable region, which comprises an amino acid sequence selected from SEQ ID NO:6.

Suitable and preferred subjects, and diseases (including the characteristics of the diseases and various types of cancers) are as disclosed herein.

An additional embodiment of the present invention is a composition for treating or ameliorating the effects of a disease in a subject. The composition comprises:
  (a) a therapeutically effective amount of an anti-metabolite agent or analog thereof; and
  (b) a therapeutically effective amount of a monoclonal antibody or antigen binding fragment thereof, wherein the monoclonal antibody comprises:
    (i) a heavy chain variable region (VH), which comprises an amino acid sequence selected from the group consisting of SEQ ID NO:1, SEQ ID NO:3, SEQ ID NO:5, and SEQ ID NO:7; and
    (ii) a light chain variable region (VL), which comprises an amino acid sequence selected from the group consisting of SEQ ID NO:2, SEQ ID NO:4, SEQ ID NO:6, and SEQ ID NO:8.

Suitable and preferred anti-metabolite agents or analogs thereof, subjects, and diseases (including the characteristics of the diseases and various types of cancers) are as disclosed herein.

In another aspect of this embodiment, the monoclonal antibody or antigen binding fragment thereof comprises:
  (1) a VH polypeptide encoded by:

(SEQ ID NO: 11)
```
caggtccagctggtgcagtctggggctgaggtgaagaagcctgggac
ctcagtgaaggtctcctgcaaggttcctggatacaccttcagcagct
atgctatcagctgggtgcgacaggcccctggacaagggcttgagtgg
atgggagggatcatccctatctttggtacaacaaactacgcacagaa
gttccagggcagagtcacgattaccggggaggaatccacgagcacag
tctacatggagctgagcagcctgagatctgaggacacggccgtgtat
tactgtgcgagagatacggactacatgtttgactactggggccaggg
aaccctggtcaccgtgagctca
```
and
  (2) a VL polypeptide encoded by:

(SEQ ID NO: 12)
```
tcttctgagctgactcaggaccctgttgtgtctgtggccttgggaga
gacagtcagtatcacatgccaaggagacaacctcagagactttatg
caagctggtaccaacagaagccaggacaggcccctctactagtcatg
tatggtaaaaacaggcggccctcagggatcccagaccgattctctgg
ctccacctcaggaaacacactttccttgaccatcactggggctcagg
cggaagatgaggctgactattactgtagctcccgggacaacagtaag
catgtggtgttcggcgggggaccaaggtcaccgtccta.
```

In a further aspect of this embodiment, the monoclonal antibody or antigen binding fragment thereof comprises:
  (1) a VH polypeptide encoded by:

(SEQ ID NO: 13)
```
caggtccagctggtgcagtctggggctgaggtgaagaagcctggggc
ctcagtgaaggtctcctgcaaggtttctggatacaccttcagcagct
atgctatcagctgggtgcgacaggcccctggacaagggcttgagtgg
atgggagggatcatccctatctttggtacagcaaactacgcacagaa
gttccagggcagagtcacgattaccgcggacgaatccacgagcacag
cctacatggagctgagcagcctgagatctgaggacacggccgtgtat
tactgtgcgagagatacggactacatgtttgactactggggccaggg
aaccctggtcaccgtgagctca
```
and
  (2) a VL polypeptide encoded by:

(SEQ ID NO: 14)
```
tcttctgagctgactcaggaccctgttgtgtctgtggccttgggaga
gacagtcagtatcacatgccaaggagacaacctcagagactttatg
caagctggtaccaacagaagccaggacaggcccctctactagtcatg
tatggtaaaaacaggcggccctcagggatcccagaccgattctctgg
ctccacctcaggaaacacactttccttgaccatcactggggctcagg
cggaagatgaggctgactattactgtagctcccgggacaacagtaag
catgtggtgttcggcgggggaccaaggtcaccgtccta.
```

In an additional aspect of this embodiment, the monoclonal antibody or antigen binding fragment thereof comprises:
  (1) a VH polypeptide encoded by:

(SEQ ID NO: 15)
```
gaggtgcagctggtggagtctgggggaggcgtggtccagcctgggag
gtccgtgagactctcctgtgcagcctctggattcaccttcagtacct
atactatgcactgggtccgccaggctccaggcaaggggctggagtgg
gtggcaattatctcaaatgatggaagcaataagtactacgcagaccc
cgtgaggggccgattcaccatctccagagacaattccaagaacacgc
tgtatctgcaaatgaacagcctgagagctgaggacacggctgtgtat
tactgtgtacgtggcagcagctggtatcgcggaaattggttcgaccc
ctggggccagggaaccctggtcaccgtgagctca
```
and
  (2) a VL polypeptide encoded by:

(SEQ ID NO: 16)
```
gacatccagatgacccagtctccatcctccctgtctgcatctgtagg
agacagagtcaccatcgcttgccgggcaagtcagaccattagtaggt
atttaaattggtatcagcagaaaccagggaaagcccctaagctcctg
atctatgctgcatccagtttgcaaagtgggtctcatcaaggttcag
tggcagtggatctgggacagagttcactctcaccatcagcagtctgc
agcctgaagattttgcaacttatttctgtcaacagacttacagtccc
ccgatcaccttcggccaagggacacgactggagattaaacga.
```

In another aspect of this embodiment, the monoclonal antibody or antigen binding fragment thereof comprises:
(1) a VH polypeptide encoded by:

(SEQ ID NO: 17)
gaggtgcagctggtggagaccggggctgaggtgaagaagcctggggc ctcagtgaaggtctcctgcaaggcttctggatacaccttcaccggct actatatgcactgggtgcgacaggcccctggacaagggcttgagtgg atgggatggatcaaccctaccagtggtagcacaaactatgcacagaa gtttcagggcagggtcaccatgaccagggacacgtccatcagcacag cctacatggagctgagcgggctgagatctgacgacactgccgtgtat tactgtgtgagagatccgggttctcctaagtggctggccttcgaccc ctggggccagggcaccctggtcaccgtgagctca (2) a VL polypeptide encoded by:

(SEQ ID NO: 18)
gacatccagttgacccagtctccatcctccttgtctgcttctgtagg agacagagtcaccatcacttgccgggcaagtcgggccattagtaggt atttaaattggtatcagcagaaaccagggaaagcccctaagctcctg atctatgctgcatccagtttgcaaagtggggtctcatcaaggttcag tggcagtggatctgggacagagttcactctcaccatcagcagtctgc agcctgaagattttgcaacttatttctgtcaacagacttacagtccc ccgatcaccttcggccaagggacacgactggagattaaacgt.

Another embodiment of the present invention is a composition for treating or ameliorating the effects of a disease in a subject. The composition comprises:
(a) a therapeutically effective amount of an anti-metabolite agent or analog thereof; and
(b) a therapeutically effective amount of a monoclonal antibody or antigen binding fragment thereof, wherein the monoclonal antibody comprises:
(i) a heavy chain variable region, which comprises an amino acid sequence selected from SEQ ID NO:5; and
(ii) a light chain variable region, which comprises an amino acid sequence selected from SEQ ID NO:6.

Suitable and preferred anti-metabolite agents or analogs thereof, subjects, and diseases (including the characteristics of the diseases and various types of cancers) are as disclosed herein.

A further embodiment of the present invention is a composition for treating or ameliorating the effects of a disease in a subject. The composition comprises:
(a) a therapeutically effective amount of 5-fluorouracil; and
(b) a therapeutically effective amount of a monoclonal antibody or antigen binding fragment thereof, wherein the monoclonal antibody comprises:
(i) a heavy chain variable region, which comprises an amino acid sequence selected from SEQ ID NO:5; and
(ii) a light chain variable region, which comprises an amino acid sequence selected from SEQ ID NO:6.

Suitable and preferred subjects, and diseases (including the characteristics of the diseases and various types of cancers) are as disclosed herein.

An additional embodiment of the present invention is a pharmaceutical composition. The pharmaceutical composition comprises any of the compositions disclosed herein and a pharmaceutically acceptable diluent or carrier. For the pharmaceutical compositions of the present invention, suitable and preferred anti-metabolite agents or analogs thereof, subjects, monoclonal antibodies or antigen binding fragments thereof (including those comprising specific SEQ ID NOs), and diseases (including the characteristics of the diseases and various types of cancers) are as disclosed herein.

The pharmaceutical compositions according to the present invention may be in a unit dosage form comprising both agents, namely (a), the anti-metabolite agent or an analog thereof, preferably 5-fluorouracil, ("(a) agent(s)"), and (b) a monoclonal antibody or antigen binding fragment thereof according to the present invention ("(b) agent"). In another aspect of this embodiment, the agent(s) identified in (a) above is in a first unit dosage form and the agent identified in (b) above is in a second unit dosage form, separate from the first.

The agents identified in (a) and (b) above may be co-administered to the subject, either simultaneously or at different times and in any order, as deemed most appropriate by a physician. If the (a) and (b) agents are administered at different times, for example, by serial administration, the (a) agent(s) may be administered to the subject before the (b) agent. Alternatively, the (b) agent may be administered to the subject before the (a) agent(s).

Another embodiment of the present invention is a kit. The kit comprises any of the compositions or pharmaceutical compositions of the present invention packaged together with instructions for its use.

For use in the kits of the invention, compositions and pharmaceutical compositions comprising suitable and preferred anti-metabolite agents or analogs thereof, subjects, monoclonal antibodies or antigen binding fragments thereof (including those comprising specific SEQ ID NOs), and diseases (including the characteristics of the diseases and various types of cancers) are as set forth above. The kits may also include suitable storage containers, e.g., ampules, vials, tubes, etc., for each composition or pharmaceutical composition and other reagents, e.g., buffers, balanced salt solutions, etc., for use in administering the compositions or the pharmaceutical compositions to subjects. The compositions or the pharmaceutical compositions and other reagents may be present in the kits in any convenient form, such as, e.g., in a solution or in a powder form. The kits may further include a packaging container, optionally having one or more partitions for housing the composition or pharmaceutical composition and other optional reagents.

In the present invention, an "effective amount" or a "therapeutically effective amount" of an agent, monoclonal antibody, or fragment thereof or a compound or composition disclosed herein is an amount of such material that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of any active agent disclosed herein or a composition containing the same will be that amount of the active agent or composition, which is the lowest dose effective to produce the desired effect. The effective dose of an agent, monoclonal antibody, or fragment thereof or a compound or composition of the present invention may be administered as two, three, four, five, six or more sub-doses, administered separately at appropriate intervals throughout the day.

A suitable, non-limiting example of a dosage of an anti-metabolite or analog thereof, and a monoclonal antibody, or an antigen binding fragment disclosed herein is from about 1 mg/kg to about 2400 mg/kg per day, such as from about 1 mg/kg to about 1200 mg/kg per day, including from about 50 mg/kg to about 1200 mg/kg per day. Other representative dosages of such agents include about 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. The effective dose of anti-metabolite agents or analogs thereof, antibodies, and antibody fragments disclosed herein may be administered as two, three, four, five, six or more sub-doses, administered separately at appropriate intervals throughout the day.

The compositions and pharmaceutical compositions of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, the compositions and pharmaceutical compositions of the present invention may be administered in conjunction with other treatments. Each composition and pharmaceutical composition of the present invention may be encapsulated or otherwise protected against gastric or other secretions, if desired.

The compositions and pharmaceutical compositions of the invention comprise one or more active ingredients in admixture with one or more pharmaceutically-acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21st Edition, Lippincott Williams and Wilkins, Philadelphia, Pa.).

Pharmaceutically acceptable diluents or carriers are well known in the art (see, e.g., Remington, The Science and Practice of Pharmacy (21st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The compositions and pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Compositions and pharmaceutical compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable diluents or carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. Any active ingredient of the invention can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Compositions and pharmaceutical compositions of the present invention for rectal or vaginal administration may be presented as a suppository, which may be prepared by mixing one or more active ingredient(s) with one or more suitable nonirritating diluents or carriers which are solid at room temperature, but liquid at body temperature and, therefore, will melt in the rectum or vaginal cavity and release the active compound. Compositions and pharmaceutical compositions of the present invention which are suitable for vaginal administration also include pessaries, tampons, creams, gels, pastes, foams or spray formulations containing such pharmaceutically-acceptable carriers as are known in the art to be appropriate.

Dosage forms for topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

Compositions and pharmaceutical compositions of the present invention suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., a composition or a pharmaceutical composition of the present invention), it is desirable to slow its absorption from subcutaneous or intramuscular injection. This may be accomplished by the use of a liquid suspension of crystalline or amorphous material having poor water solubility.

The rate of absorption of the active any active agent/composition of the invention then depends upon its rate of dissolution which, in turn, may depend upon crystal size and crystalline form. Alternatively, delayed absorption of a parenterally-administered any active agent/composition of the invention may be accomplished by dissolving or suspending the active agent/composition in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

Any formulation of the invention may be presented in unit-dose or multi-dose sealed containers, for example, ampules and vials, and may be stored in a lyophilized condition requiring only the addition of the sterile liquid diluent or carrier, for example water for injection, immediately prior to use. Extemporaneous injection solutions and suspensions may be prepared from sterile powders, granules and tablets of the type described above.

ADDITIONAL DEFINITIONS

As used herein, terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

The term "amino acid" means naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. An "amino acid analog" means compounds that have the same basic chemical structure as a naturally occurring amino acid, e.g., a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. An "amino acid mimetic" means a chemical compound that has a structure that is different from the general chemical structure of an amino acid, but that functions similarly to a naturally occurring amino acid.

"Nucleic acid" or "oligonucleotide" or "polynucleotide" used herein mean at least two nucleotides covalently linked together. Many variants of a nucleic acid may be used for the same purpose as a given nucleic acid. Thus, a nucleic acid also encompasses substantially identical nucleic acids and complements thereof.

Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be synthesized as a single stranded molecule or expressed in a cell (in vitro or in vivo) using a synthetic gene. Nucleic acids may be obtained by chemical synthesis methods or by recombinant methods.

The nucleic acid may also be a RNA such as a mRNA, tRNA, short hairpin RNA (shRNA), short interfering RNA (sRNA), double-stranded RNA (dsRNA), transcriptional gene silencing RNA (ptgsRNA), Piwi-interacting RNA, pri-miRNA, pre-miRNA, micro-RNA (miRNA), or anti-miRNA, as described, e.g., in U.S. patent application Ser. Nos. 11/429,720, 11/384,049, 11/418,870, and 11/429,720 and Published International Application Nos. WO 2005/116250 and WO 2006/126040.

The nucleic acid may also be an aptamer, an intramer, or a spiegelmer. The term "aptamer" refers to a nucleic acid or oligonucleotide molecule that binds to a specific molecular target. Aptamers are derived from an in vitro evolutionary process (e.g., SELEX (Systematic Evolution of Ligands by EXponential Enrichment), disclosed in U.S. Pat. No. 5,270,163), which selects for target-specific aptamer sequences from large combinatorial libraries. Aptamer compositions may be double-stranded or single-stranded, and may include deoxyribonucleotides, ribonucleotides, nucleotide derivatives, or other nucleotide-like molecules. The nucleotide components of an aptamer may have modified sugar groups (e.g., the 2'-OH group of a ribonucleotide may be replaced by 2'-F or 2'-NH$_2$), which may improve a desired property, e.g., resistance to nucleases or longer lifetime in blood. Aptamers may be conjugated to other molecules, e.g., a high molecular weight carrier to slow clearance of the aptamer from the circulatory system. Aptamers may be specifically cross-linked to their cognate ligands, e.g., by photo-activation of a cross-linker (Brody, E. N. and L. Gold (2000) J. Biotechnol. 74:5-13).

The term "intramer" refers to an aptamer which is expressed in vivo. For example, a vaccinia virus-based RNA expression system has been used to express specific RNA aptamers at high levels in the cytoplasm of leukocytes (Blind, M. et al. (1999) Proc. Natl. Acad. Sci. USA 96:3606-3610).

The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those disclosed in U.S. Pat. Nos. 5,235,033 and 5,034,506. Nucleic acids containing one or more non-naturally occurring or modified nucleotides are also included within the definition of nucleic acid. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; 0- and N-alkylated nucleotides, e.g. N6-methyl adenosine are suitable. The 2'-OH-group may be replaced by a group selected from H, OR, R, halo, SH, SR, NH$_2$, NHR, NR$_2$ or CN, wherein R is C$_1$-C$_6$ alkyl, alkenyl or alkynyl and halo is F, Cl, Br or I. Modified nucleotides also include nucleotides conjugated with cholesterol through, e.g., a hydroxyprolinol linkage as disclosed in Krutzfeldt et al., Nature (Oct. 30, 2005), Soutschek et al., Nature 432:173-178 (2004), and U.S. Patent Application Publication No. 20050107325. Modified nucleotides and nucleic acids may also include locked nucleic acids (LNA), as disclosed in U.S. Patent Application Publication No. 20020115080. Additional modified nucleotides and nucleic acids are disclosed in U.S. Patent Application Publication No. 20050182005. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

The terminology used herein is for the purpose of describing particular embodiments only and is not intended to be limiting. As used in the specification and the appended claims, the singular forms "a," "an," and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

The following examples are provided to further illustrate the methods of the present invention. These examples are illustrative only and are not intended to limit the scope of the invention in any way.

EXAMPLES

Example 1

Materials and Methods

Mice

Unless otherwise noted, female immunodeficient athymic nude mice (Crl:NU(Ncr)-Foxn/nu, Charles River) were used at nine weeks old with a body weight (BW) range of about 15 to about 30 grams on Day 1 of the study.

In Vivo Implantation and Tumor Growth

Tumor cells were cultured in RPMI-1640 medium supplemented with 10% fetal bovine serum, 2 mM glutamine, 100 units/mL penicillin G sodium, 100 µg/mL streptomycin sulfate, and 25 µg/mL gentamicin. The tumor cells were grown in tissue culture flasks in a humidified incubator at 37° C., in an atmosphere of 5% $CO_2$ and 95% air.

On the day of tumor implant, each test mouse was injected with cultured tumor cells, and tumor growth was monitored as the average size approached the target range. Tumors were measured in two dimensions using calipers, and volume was calculated using the formula:

$$\text{Tumor Volume (mm}^3\text{)}=(w^2 \times l)/2$$

where w=width and l=length, in mm, of the tumor. Tumor weight was estimated with the assumption that 1 mg is equivalent to 1 $mm^3$ of tumor volume. For all therapeutic studies, mice were sorted into groups containing the same average size tumors prior to initiation of therapy.

Controls

One group in each cohort received 1% vehicle IP three times per week to end, and served as the control group for calculation of % tumor growth delay (TGD).

Endpoint and TGD Analysis

Tumors were measured using calipers twice per week, and each animal was euthanized when its tumor reached the pre-determined tumor volume endpoint described for each experiment (usually 2000 $mm^3$) or on the final day, whichever came first. Animals that exited the study for tumor volume endpoint were documented as euthanized for tumor progression (TP), with the date of euthanasia. The time to endpoint (TTE) for analysis was calculated for each mouse by the following equation:

$$\text{TTE}=[\log_{10}(\text{endpoint volume})-b]/m$$

where TTE is expressed in days, endpoint volume is expressed in $mm^3$, b is the intercept, and m is the slope of the line obtained by linear regression of a log-transformed tumor growth data set. The data set consisted of the first observation that exceeded the endpoint volume used in analysis and the three consecutive observations that immediately preceded the attainment of this endpoint volume. The calculated TTE was usually less than the TP date, the day on which the animal was euthanized for determination of tumor size. Animals with tumors that did not reach the endpoint volume were assigned a TTE value equal to the last day of the study. Any animal classified as having died from NTR (non-treatment-related) causes due to accident (NTRa) or due to unknown etiology (NTRu) were excluded from TTE calculations and all further analyses. Animals classified as TR (treatment-related) deaths or NTRm (non-treatment-related death due to metastasis) were assigned a TTE value equal to the day of death.

Treatment outcome was evaluated from TGD, defined as the increase in the median TTE in a treatment group compared to the control group:

$$\text{TGD}=T-C,$$

expressed in days, or as a percentage of the median TTE of the control group:

$$\%\text{ TGD}=[(T-C)/C] \times 100$$

where:

T=median TTE for a treatment group, and
C=median TTE for the designated control group.

Criteria for Regression Responses

Treatment efficacy was determined from the incidence and magnitude of regression responses observed during the study. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 $mm^3$ for one or more of these three measurements. In a CR response, the tumor volume was less than 13.5 $mm^3$ for three consecutive measurements during the course of the study. An animal with a CR response at the termination of the study was additionally classified as a tumor-free survivor (TFS). Animals were monitored for regression responses.

Toxicity

Animals were weighed daily on Days 1-5, then twice per week until completion of the study. The mice were observed frequently for overt signs of any adverse, treatment related side effects, and clinical signs were recorded when observed. Individual body weight (BW) loss was monitored, and any animal whose weight exceeded the 20% limits for acceptable BW loss was euthanized. Group mean BW loss also was monitored as per protocol. Dosing was suspended in any group that exceeded the 20% limits for acceptable mean BW loss. If mean BW recovered, then dosing was resumed in that group, but at a lower dosage or less frequent dosing schedule. Acceptable toxicity for the maximum tolerated dose (MTD) was defined as a group mean BW loss of less than 20% during the study and not more than 10% TR deaths. A death was classified as TR if attributable to treatment side effects as evidenced by clinical signs and/or necropsy, or was also classified as TR if due to unknown causes during the dosing period or within 14 days of the last dose. A death was classified as NTR if there was no evidence that death is related to treatment side effects.

Statistical and Graphical Analyses

Prism (GraphPad) for Windows 3.03 was used for statistical analyses. The logrank test, which evaluates overall survival experience, was used to analyze significance of the differences between the TTE values of two groups. Logrank analysis includes data for all animals in a group except those assessed as NTR deaths. Two-tailed statistical analyses were conducted at significance level P=0.05. The statistical tests were not adjusted for multiple comparisons. Test results are identified as not significant "ns" at P>0.05, significant (symbolized by "*") at 0.01<P<0.05, very significant ("") at 0.001<P≤0.01, and extremely significant ("*") at P≤0.001. Groups with regimens above the MTD were not evaluated statistically.

Example 2

Efficacy of TEM8 Antibodies in the HCT116 Colorectal Carcinoma Xenograft Model $2.5\times10^6$ to $5\times10^6$ HCT116 tumor cells were injected subcutaneously into the flank of mice. Tumor weights were calculated following surgical removal. Treatment was initiated when tumor volume reached 60-80 mm$^3$. Treatment groups are shown in Table 3. Dosing volume was 10 mL/kg (0.2 mL/20 g mouse).

TABLE 3

Protocol Design for the HCT116-e401 Study

Treatment Regimen

| Group | n | Agent | Vehicle | mg/kg | Route | Schedule |
|---|---|---|---|---|---|---|
| 1[#] | 15 | Vehicle | Histidine Buffer | — | IP | 3x/wk x 3 |
| 2 | 15 | M825 | Histidine Buffer | 5 | IP | 3x/wk x 3 |
| 3 | 15 | M825 | Histidine Buffer | 15 | IP | 3x/wk x 3 |
| 4 | 15 | M822 | Histidine Buffer | 5 | IP | 3x/wk x 3 |
| 5 | 15 | M822 | Histidine Buffer | 15 | IP | 3x/wk x 3 |
| 6 | 15 | M863 | Histidine Buffer | 5 | IP | 3x/wk x 3 |
| 7 | 15 | M863 | Histidine Buffer | 15 | IP | 3x/wk x 3 |
| 8 | 15 | M830 | Histidine Buffer | 5 | IP | 3x/wk x 3 |
| 9 | 15 | M830 | Histidine Buffer | 15 | IP | 3x/wk x 3 |
| 10 | 10 | Bevacizumab | Saline | 5 | IP | 2x/wk x 3 |

[#]Control group,
IP-intraperitoneal

FIG. 1A shows the group median tumor volume distribution on day 21 of this study. TEM8 Ab (hIgG1) doses were 5 and 15 mg/kg, three times per week, for 3 weeks. Bevacizumab was dosed at 5 mg/kg, twice per week, for 3 weeks. FIG. 1B and FIG. 1D show mean tumor growth and percent body weight change for each group, respectively, over the time course of the study. FIG. 1C shows the individual times to endpoint for each mouse in the study. The results show that anti-TEM8 antibodies according to the present invention were effective against HCT116 cancer cells in the HCT116 xenograft model.

Example 3

Comparison of TEM8 Antibody Efficacy in UACC Melanoma Model

Figure 2:
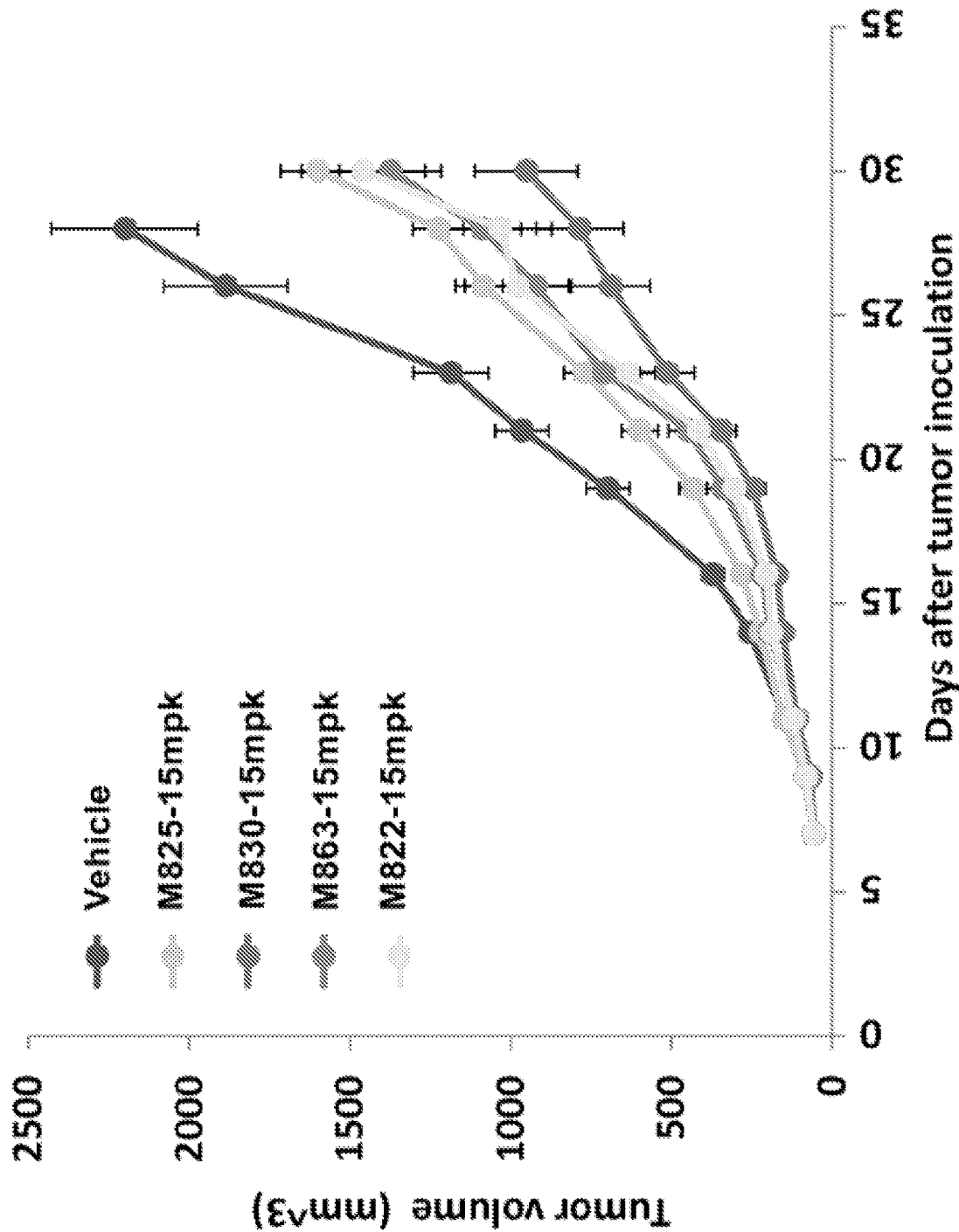
FIG. 2 shows a line graph of tumor volume in the UACC melanoma model. Treatments were initiated when tumor volumes were approximately 50 mm$^3$. TEM 8 antibodies (hIgG1) were dosed at 15 mg/kg, three times per week, for 3-4 weeks.

UACC melanoma cells were cultured and injected subcutaneously into mice. Treatment was initiated with a tumor volume of 50 mm$^3$, and treatment groups consisted of one of four TEM8 antibodies (M825, M830, M863, and M822), each dosed at 15 mg/kg, 3 times per week for 3-4 weeks. FIG. 2 shows a time course of tumor growth. The results show that TEM 8 antibodies, M830 in particular, were effective at slowing tumor growth in the UACC melanoma model.

Example 4

Efficacy of M825 in Xenograft Cancer Models

Figure 3:
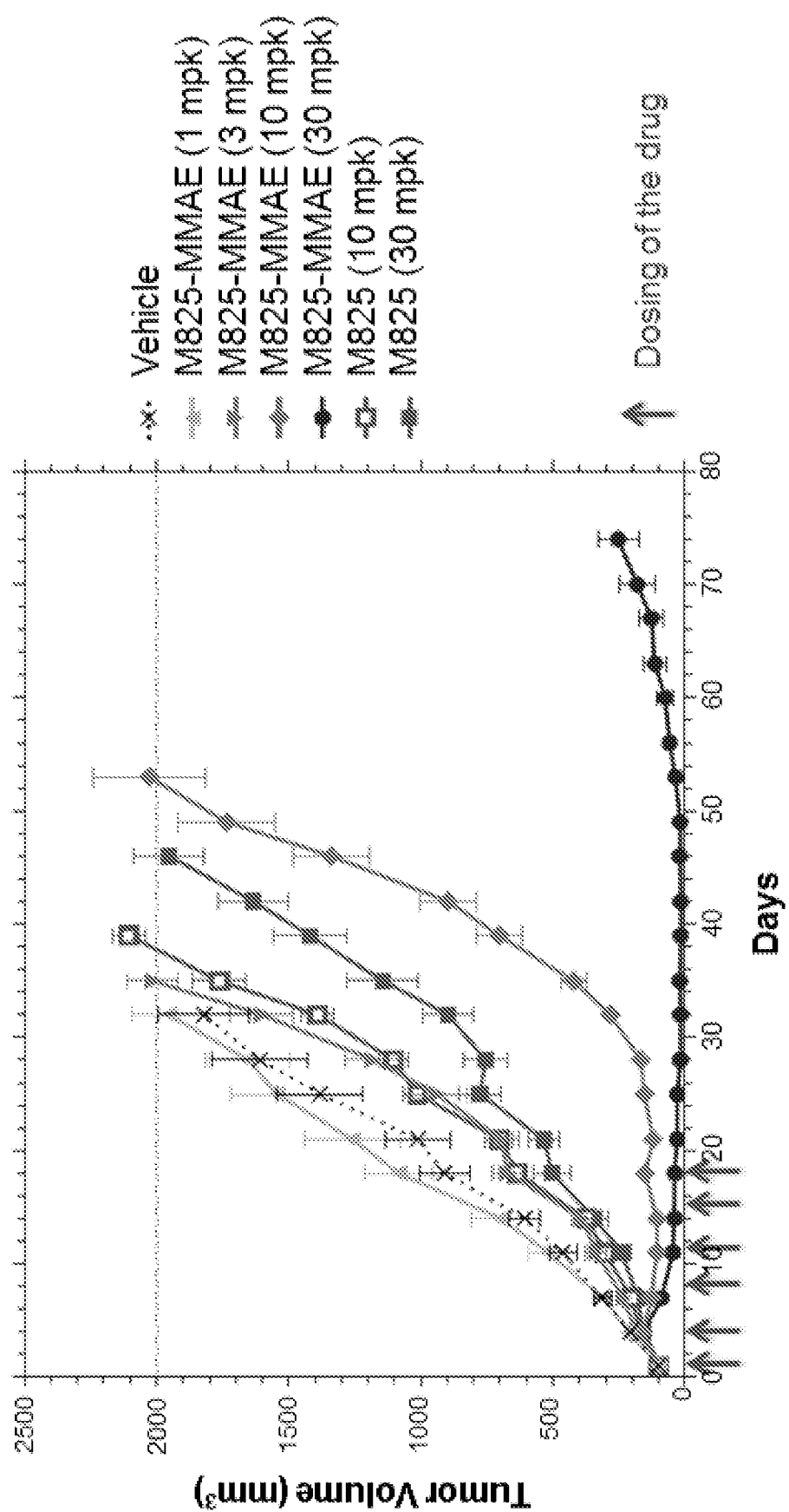
FIG. 3 shows a line graph of tumor volume over time in the HCT116 colon cancer model. The M825 antibody and drug-conjugated M825-MMAE were given 2 times per week for 3 weeks.

HCT116 Colon Cancer Model
Treatment was initiated when tumor volume reached approximately 100 mm$^3$. M825 antibody was given i.v. at a dose of 10 or 30 mg/kg, and the antibody-drug conjugate (ADC) M825-MMAE was given i.v. at 1, 3, 10, or 30 mg/kg, 2 times per week for 3 weeks. FIG. 3 shows tumor growth over the time course of the study. Results showed that the ADC significantly inhibited tumor growth at 10 and 30 mg/kg in the HCT116 model, even though it showed weak cytotoxicity towards HCT116 cancer cells in vitro (data not shown).

Figure 4:
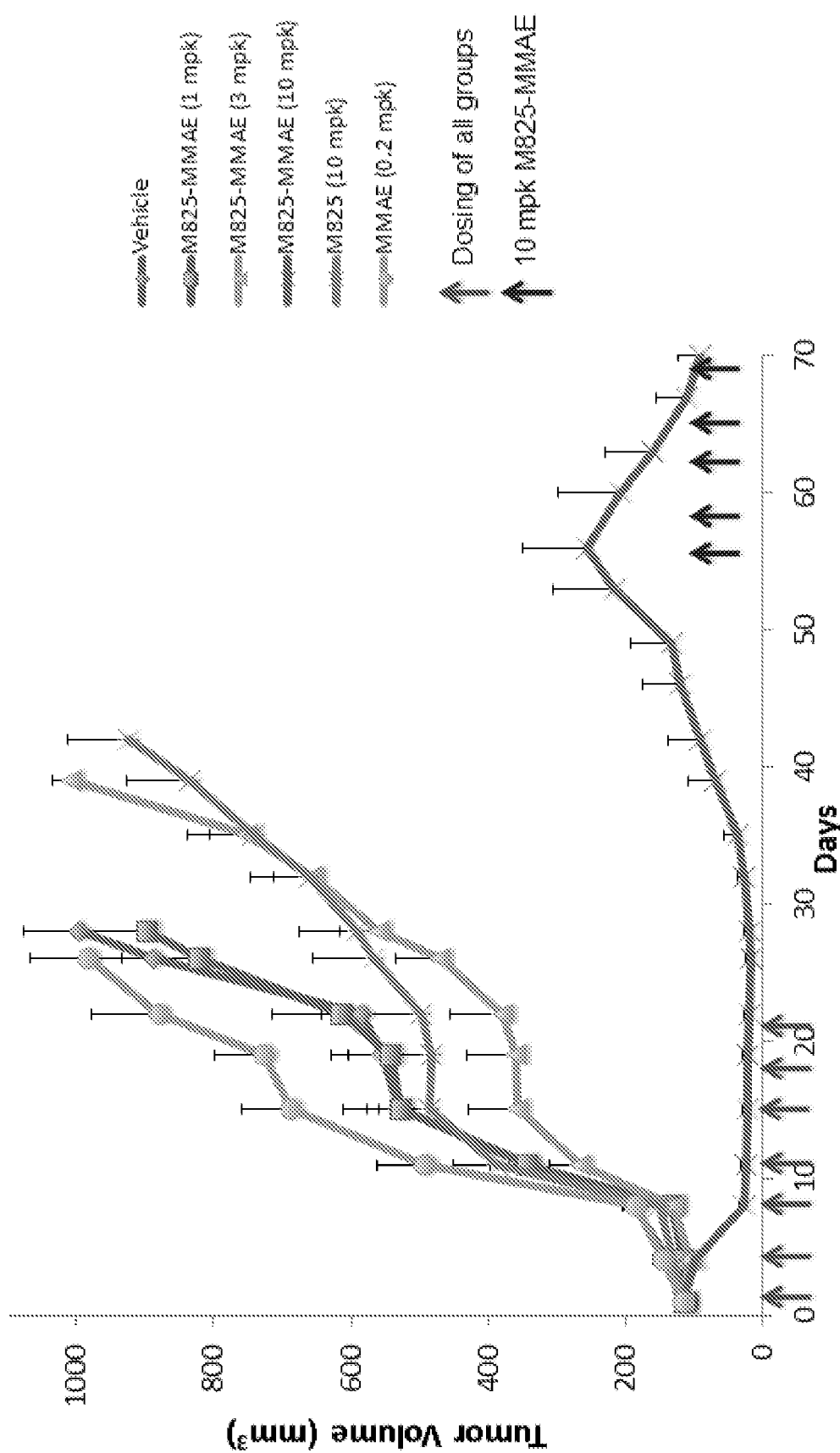
FIG. 4 shows a line graph of tumor volume over time in an OVCAR3 ovarian cancer model. TEM8 antibody M825 and antibody-drug conjugate (ADC) M825-MMAE were given 2 times per week for 3.5 weeks. The 10 mg/kg ADC group was redosed on Day 56, 2 times per week for the remainder of the study.

OVCAR3 Ovarian Cancer Model
Treatment initiated when tumor volume reached approximately 120 mm$^3$. M825 was given i.v. at 10 mg/kg and M825-MMAE was given i.v. at 1, 3, or 10 mg/kg, 2 times per week for 3.5 weeks. The ADC significantly inhibited tumor growth at 3 mg/kg and regressed tumor growth at 10 mg/kg in this model (FIG. 4). The 10 mg/kg ADC group was redosed on Day 56, 2 times per week. No effect was seen with free MMAE at 0.2 mg/kg, a dose equivalent to the maximum amount of MMAE given in the 10 mg/kg ADC group.

Figure 5:
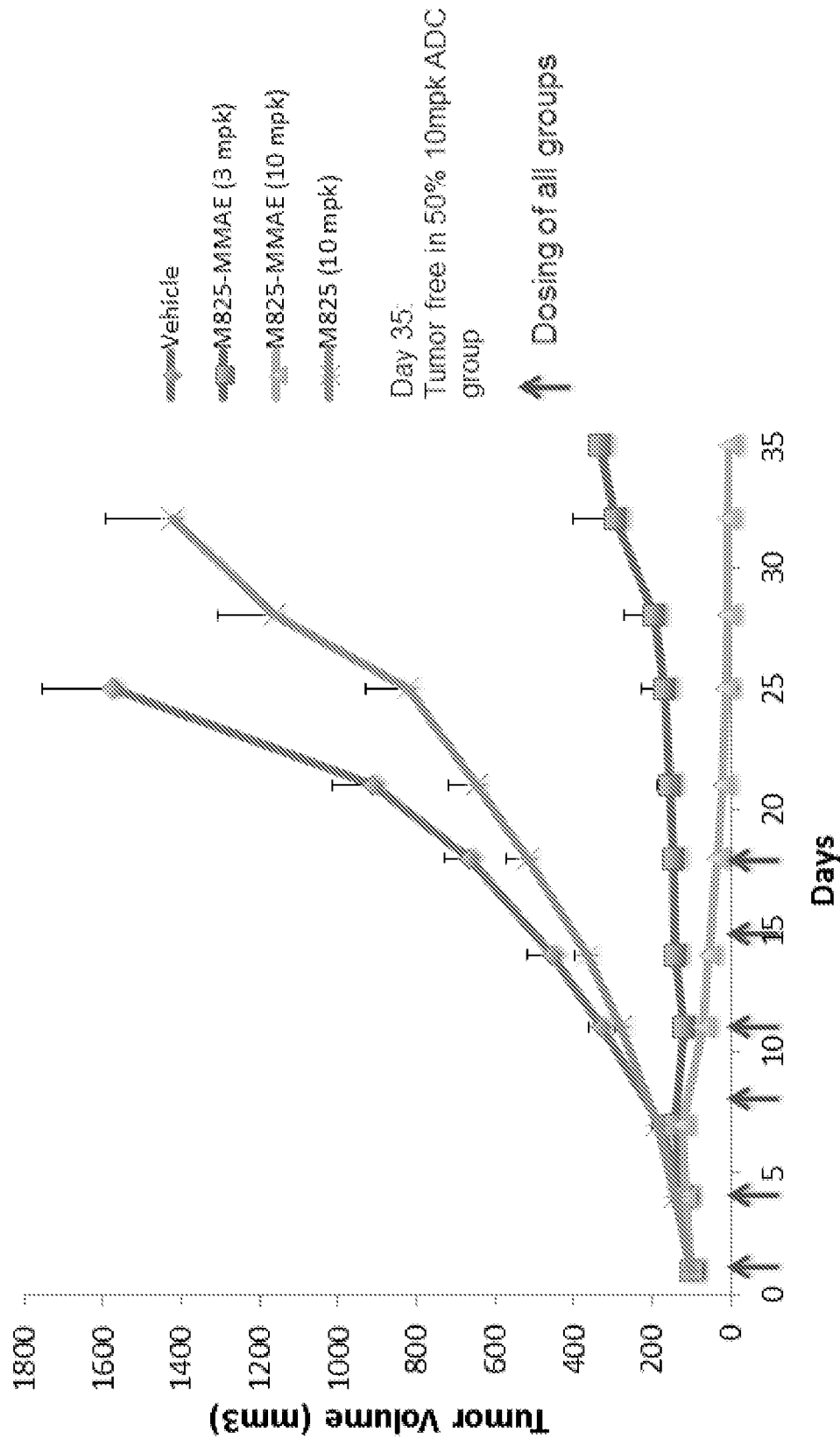
FIG. 5 shows a line graph of tumor volume over time in the MDA-MB231 breast cancer model. M825 and M825-MMAE were given 2 times per week for 3 weeks.

MDA-MB231 Triple Negative Breast Cancer Model
Treatment was initiated when tumor volume reached approximately 100 mm$^3$. M825 antibody was given i.v. at a dose of 10 mg/kg, and the antibody-drug conjugate (ADC) M825-MMAE was given i.v. at 3 or 10 mg/kg, 2 times per week for 3 weeks. The anti-TEM8 ADC treatment led to durable tumor stasis (3 mg/kg) or complete regression (10 mg/kg) in this model, even though it showed only very weak cytotoxicity toward MDA-MB231 cancer cells in vitro (data not shown). 50% of animals in the 10 mg/kg ADC group were tumor free on Day 35 (FIG. 5).

Example 5

Efficacy of M830 in the H460 Non-Small Cell Lung Carcinoma Xenograft Model

Cultured H460 cells were harvested during exponential growth and resuspended in phosphate buffered saline at a concentration of $1\times10^8$ cells/mL. $1.0\times10^7$ tumor cells were injected subcutaneously into the flank of athymic nude mice. Treatment groups are listed in Table 4. Animals were euthanized when tumors reached the pre-determined volume endpoint of 2000 mm$^3$ or on the final day (Day 88), whichever came first. All regimens were well tolerated, with no treatment related deaths, no noteworthy clinical signs, and acceptable mean body weight losses. Each treatment produced a significant survival difference versus controls (P<0.01). The median TTE for controls was 22.8 days, establishing a maximum possible TGD of 65.2 days (286%) for the 88-day study.

Both combination therapies were statistically superior to the corresponding monotherapies (P<0.05) but M830 in combination with paclitaxel was the most active treatment regimen tested in the study. Group 7 produced the maximum TGD and 90% regression responses, two PRs and seven CRs, three of which remained TFS at study end. The M830/bevacizumab combination produced TGD of 33.2 days (146%) and 40% regression responses which consisted of 1 PR and 3 CRs, all three of which remained TFS at study end.

TABLE 4

Regimen 1

| Group | n | Agent | Vehicle | mg/kg | Route | Schedule |
|---|---|---|---|---|---|---|
| 1[#] | 10 | Vehicle | PBS | — | IP | 3x/wk x 5 |
| 2 | 10 | M830 | PBS | 5 | IP | 3x/wk x 5 |

TABLE 4-continued

| | | | | Regimen 1 | | |
|---|---|---|---|---|---|---|
| Group | n | Agent | Vehicle | mg/kg | Route | Schedule |
| 3 | 10 | M830 | PBS | 15 | IP | 3x/wk x 5 |
| 4 | 10 | Bevacizumab | Saline | 5 | IP | biwk x 5/6/biwk x 4 |
| 5 | 10 | M830 | PBS | 15 | IP | 3x/wk x 5/5/ 3x/week x 4 |
| | | Bevacizumab | Saline | 5 | IP | biwk x 5/6/biwk x 4 |
| 6 | 10 | Paclitaxel | 5% EC | 30 | IV | qod x 5/29/qod x 5 |
| 7 | 10 | M830 | PBS | 15 | IP | 3x/wk x 5/5/ 3x/week x 4 |
| | | Paclitaxel | 5% EC | 30 | IV | qod x 5/29/qod x 5 |

Figure 6:
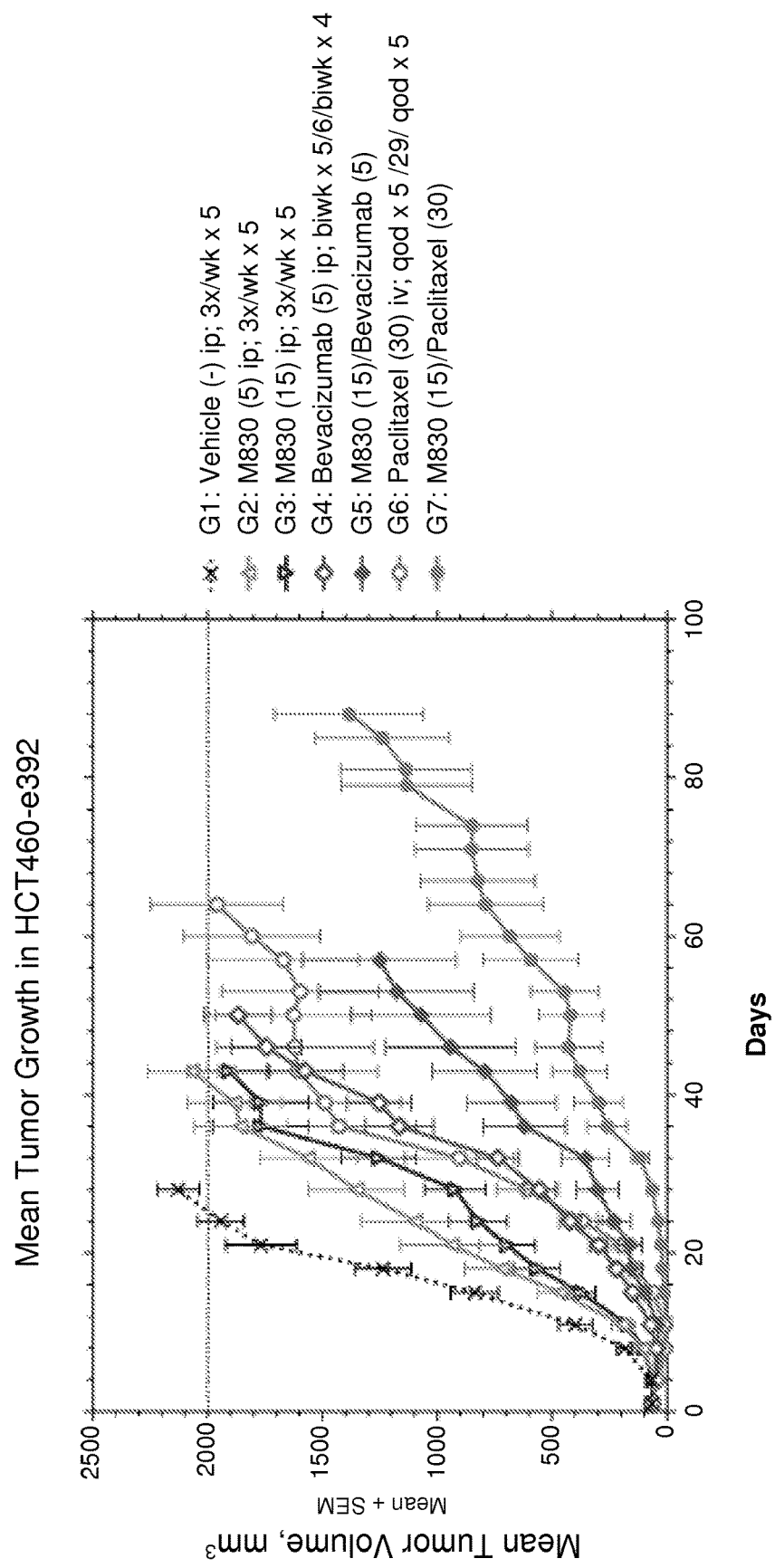
FIGS. 6A-D show results from a study of treatment with TEM8 M830 antibody, bevacizumab, paclitaxel, and combinations thereof in the H460 non-small cell lung carcinoma xenograft model.
Figure 6:
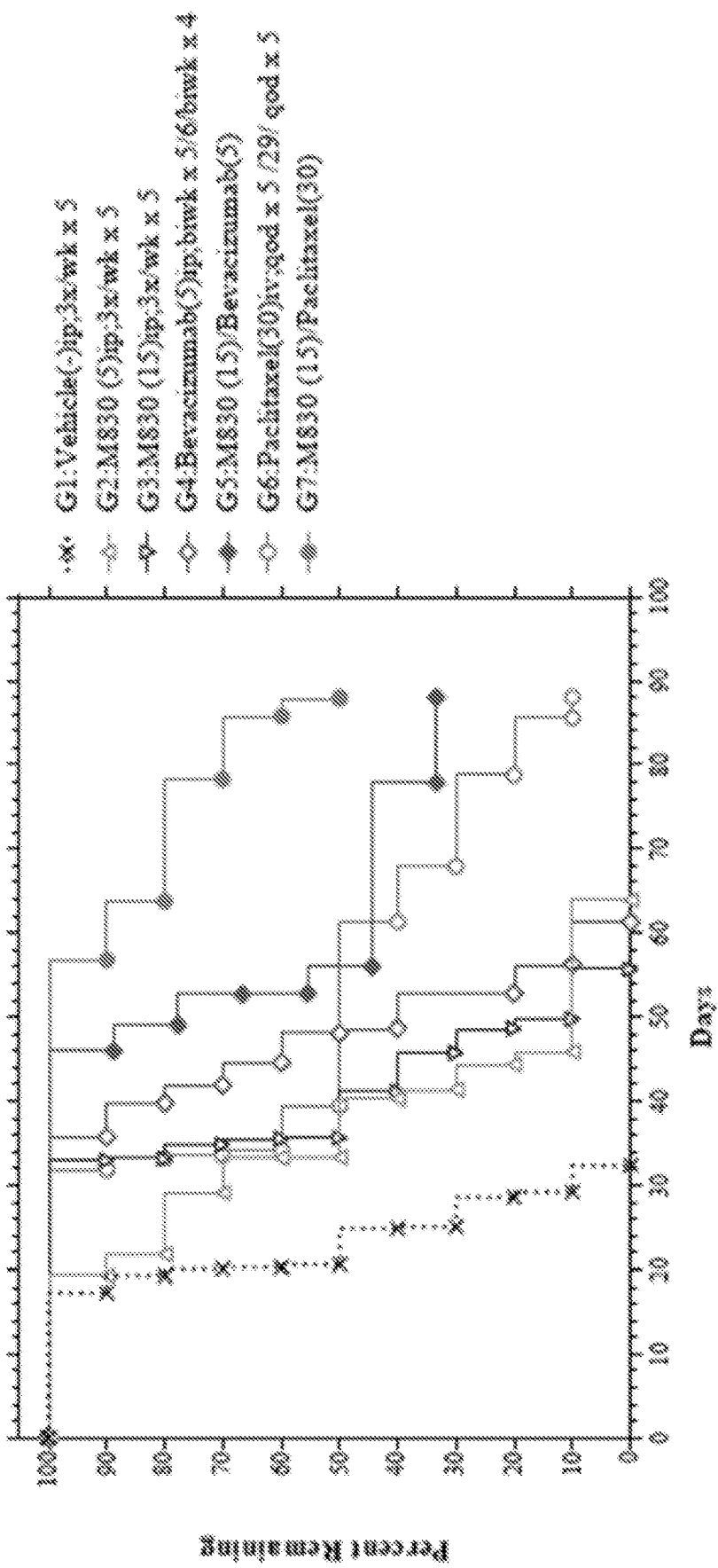
Figure 6:
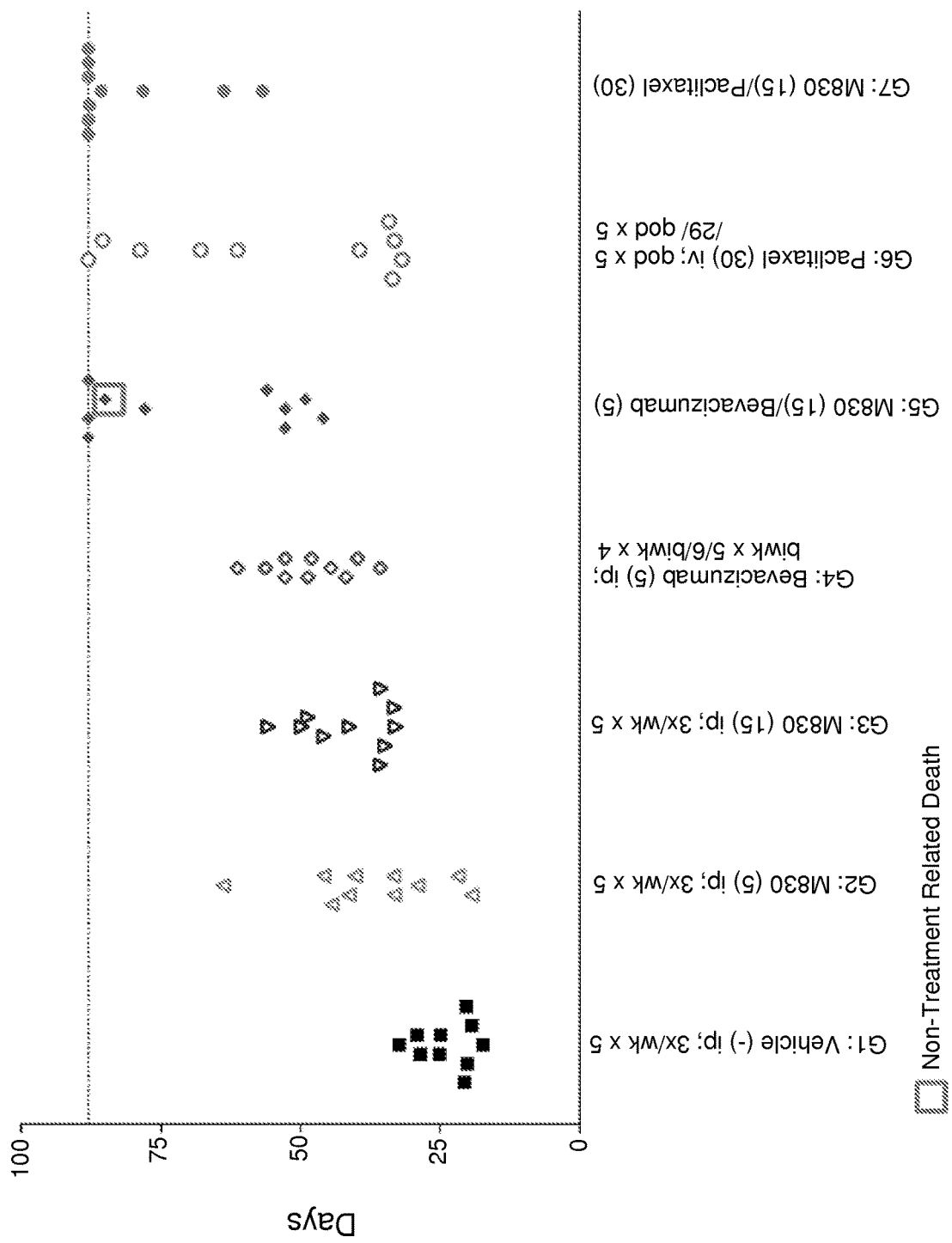
Figure 6:
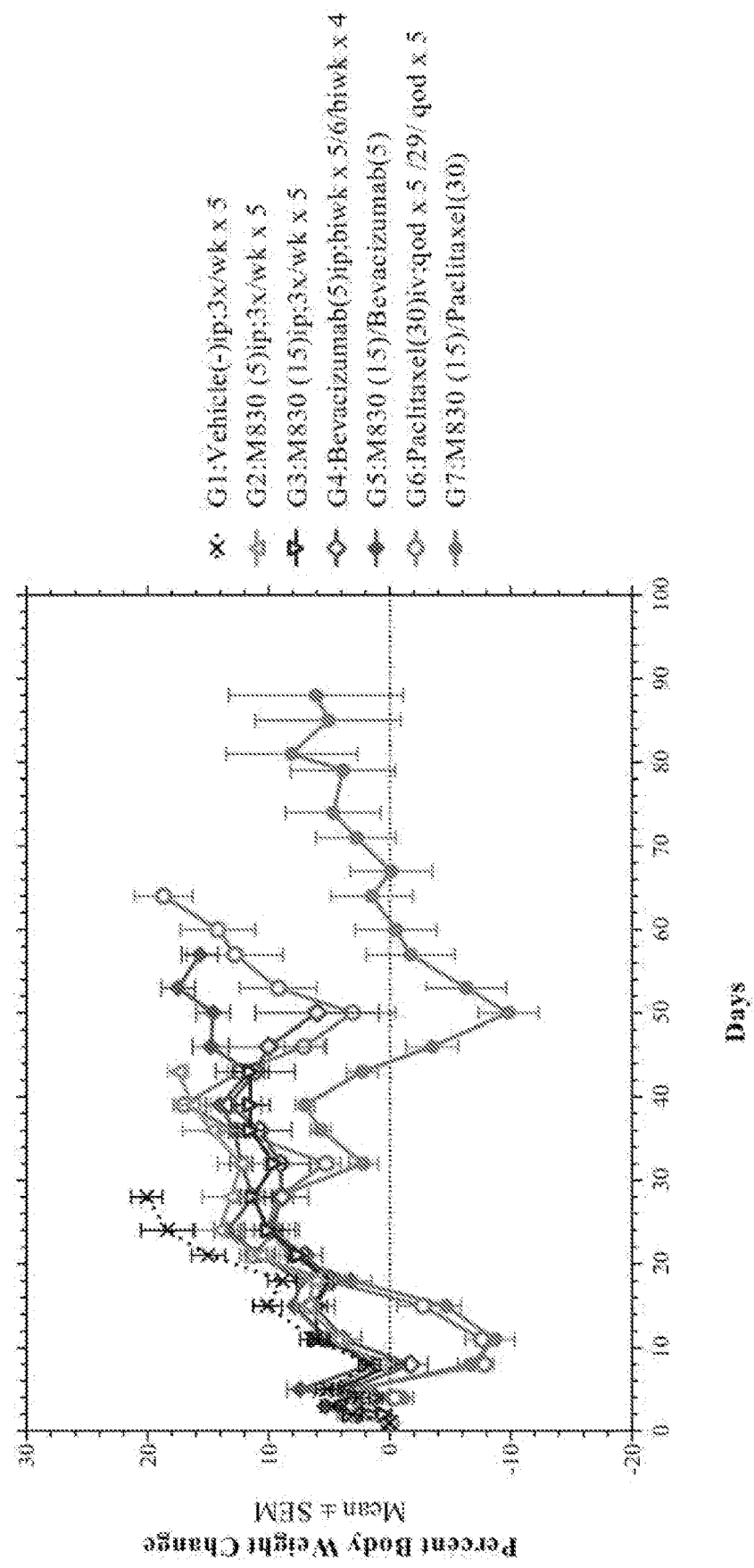

Control group,
EC-5% ethanol: 5% Cremophor EL in D5W,
IP-intraperitoneal,
IV-intravenous,
qod-every other day FIG. 6A shows a time course of mean tumor growth throughout the study. FIG. 6B shows a Kaplan-Meier survival plot and FIG. 6C show individual times to the endpoint for mice in each group. FIG. 6D shows percent body weight change for each group throughout the study. The results show that a combination of M830 and paclitaxel is effective against H460 cancer cells in the xenograft model, and that the combination is more effective than either agent alone.

Example 6

Figure 7:
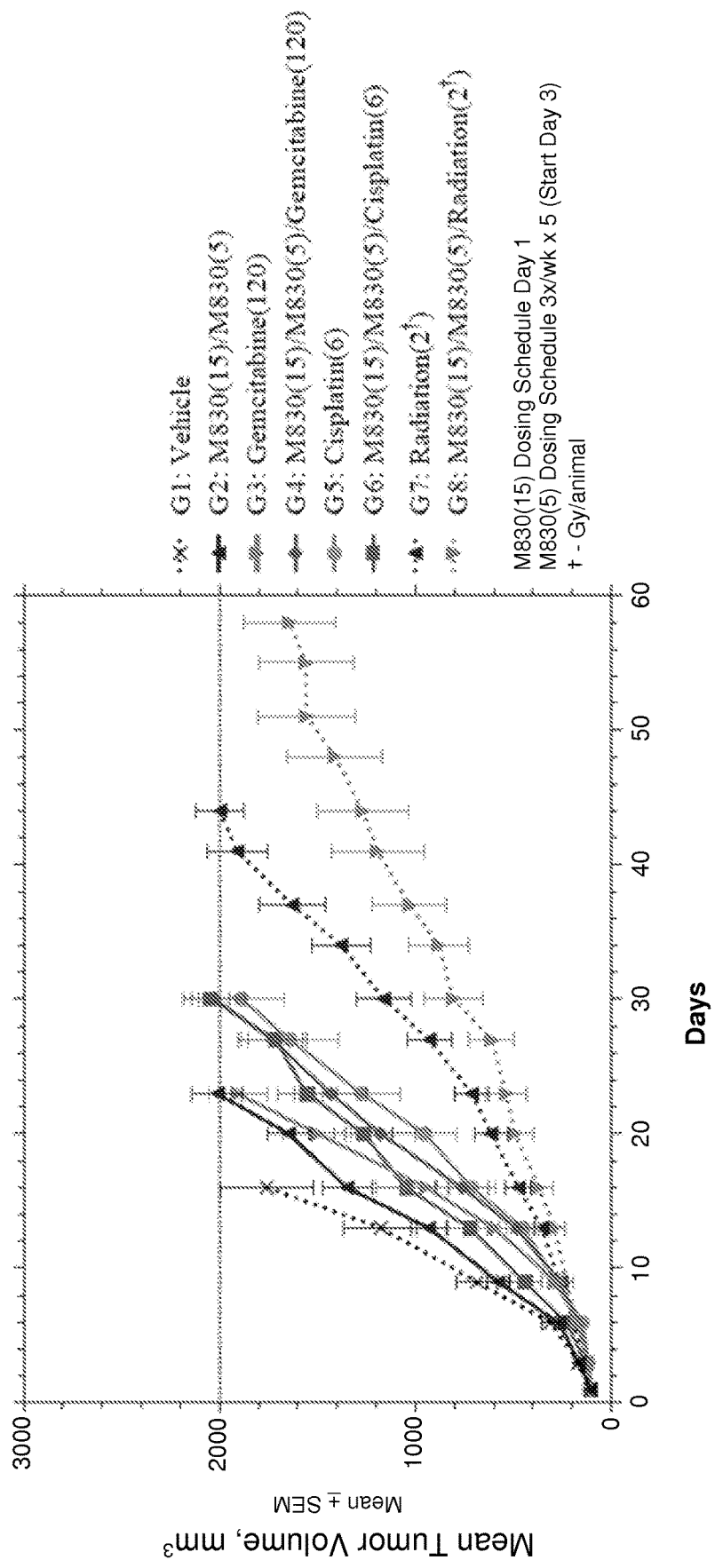
FIGS. 7A-E show results from a study of treatment with M830, gemcitabine, cisplatin, radiation, and combinations thereof in a H460 non-small cell lung carcinoma xenograft model.
Figure 7:
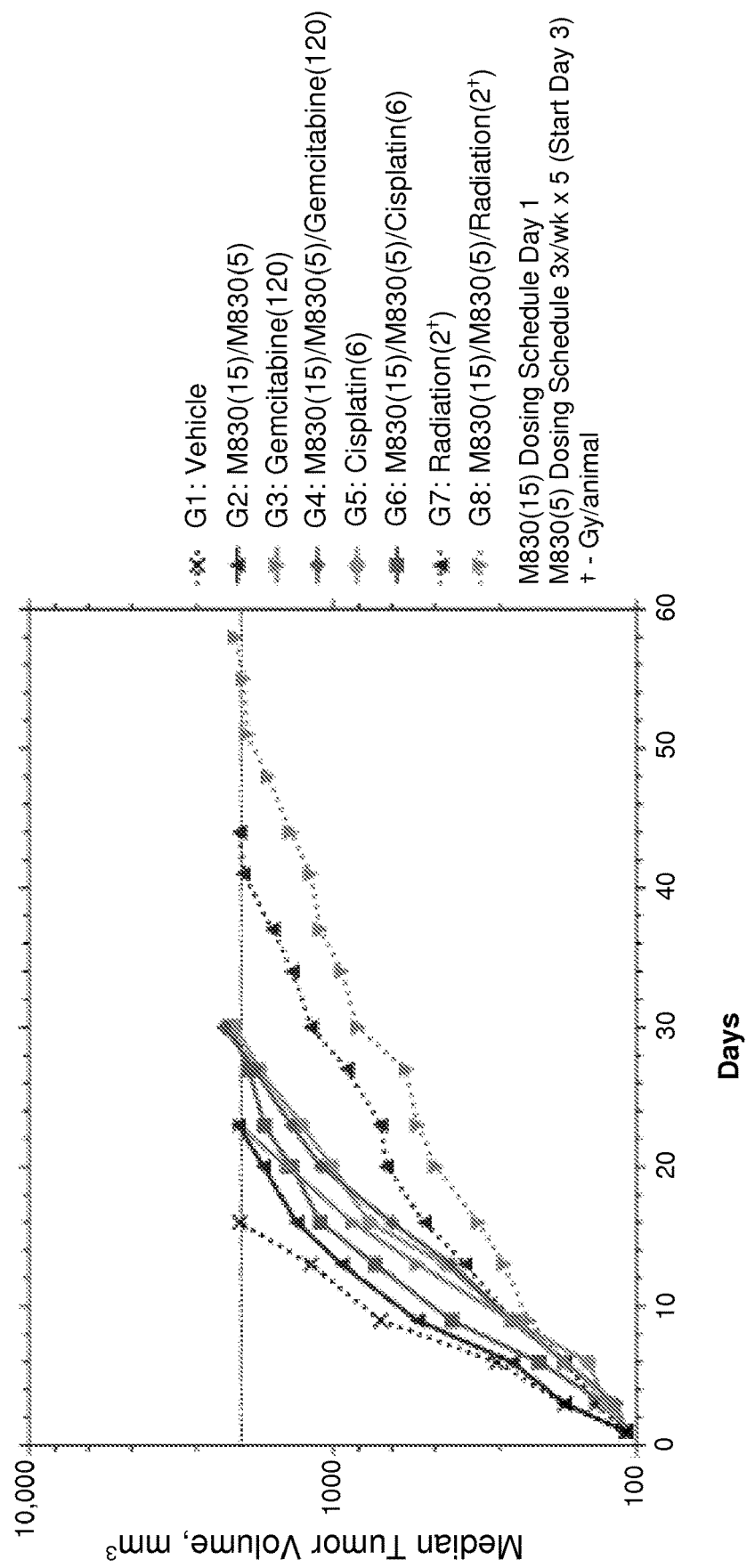
Figure 7:
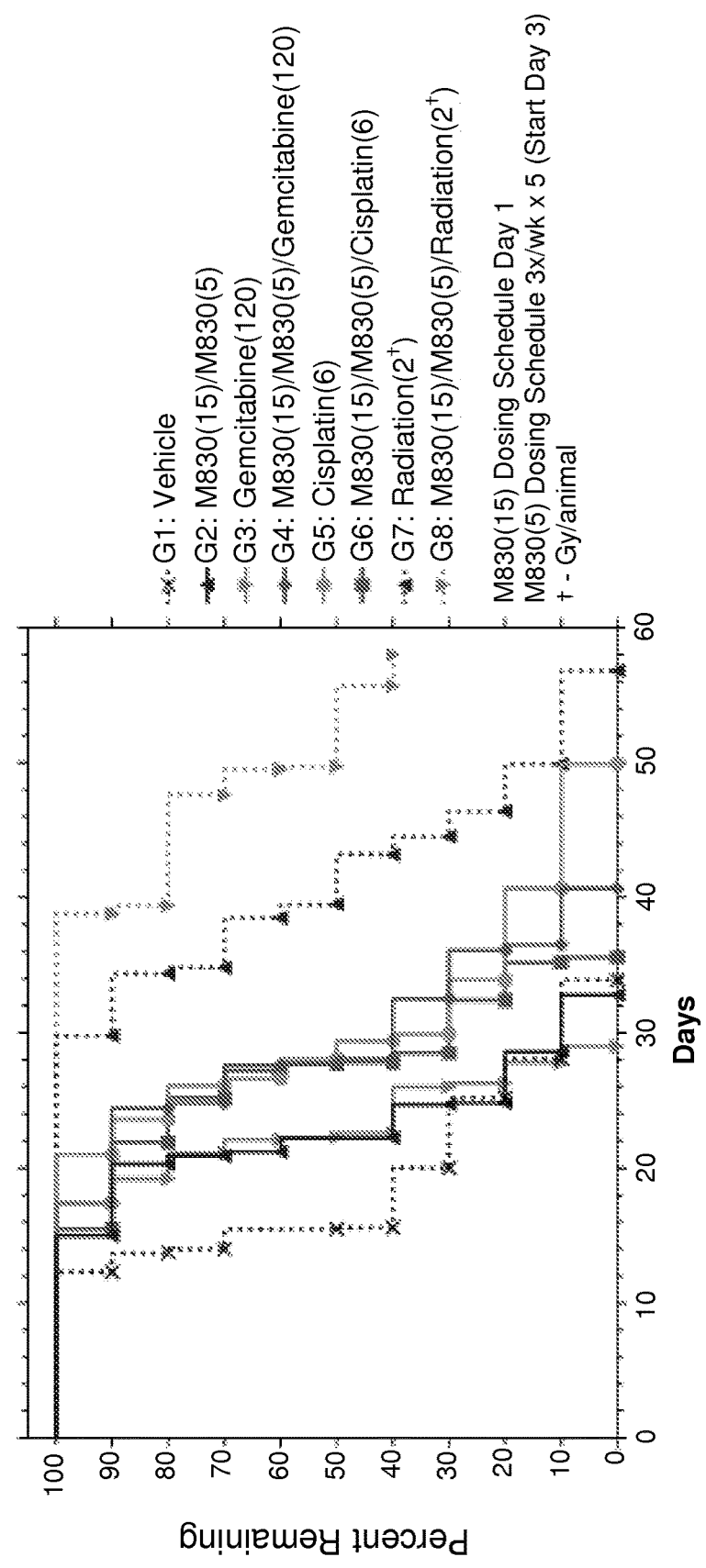
Figure 7:
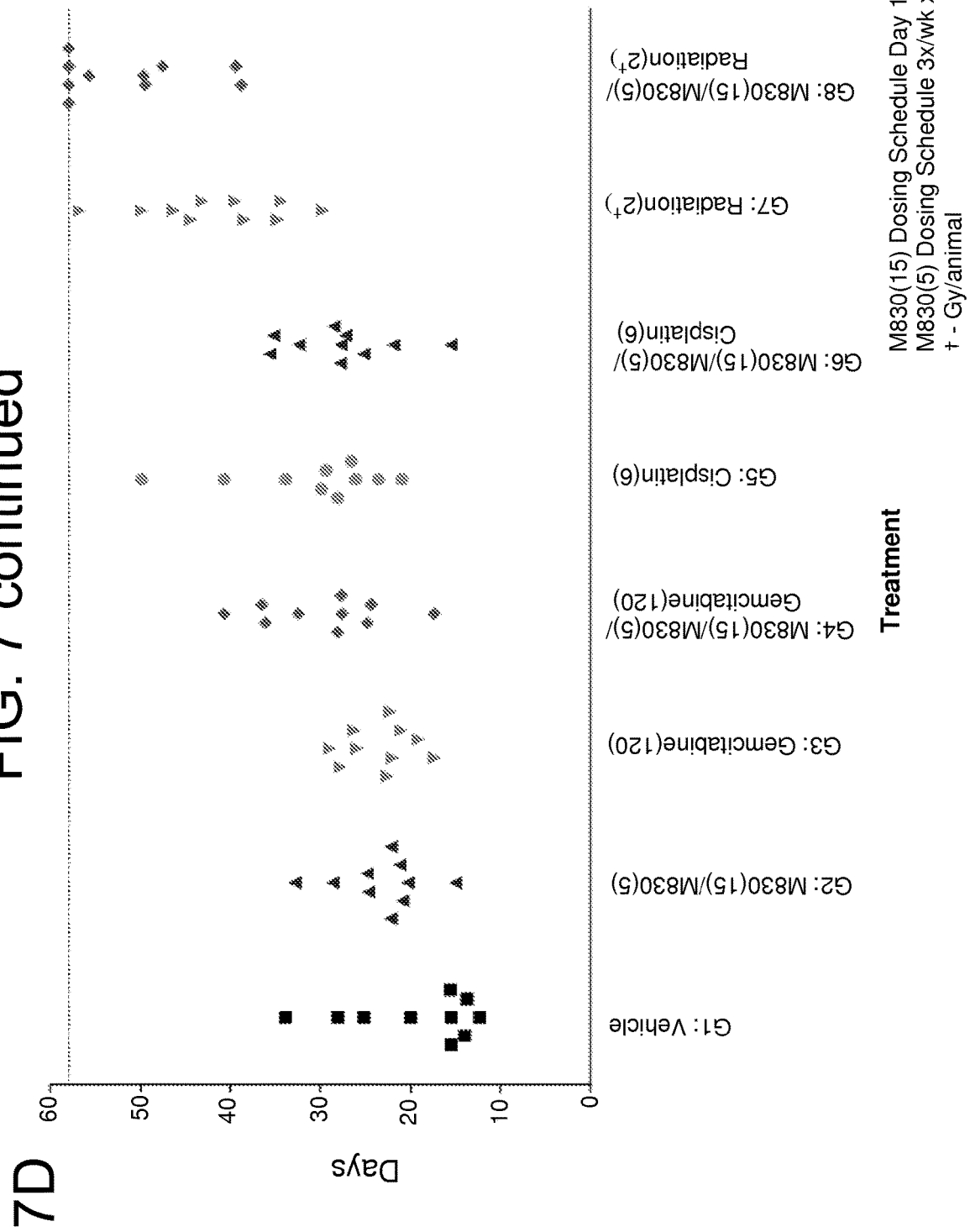
Figure 7:
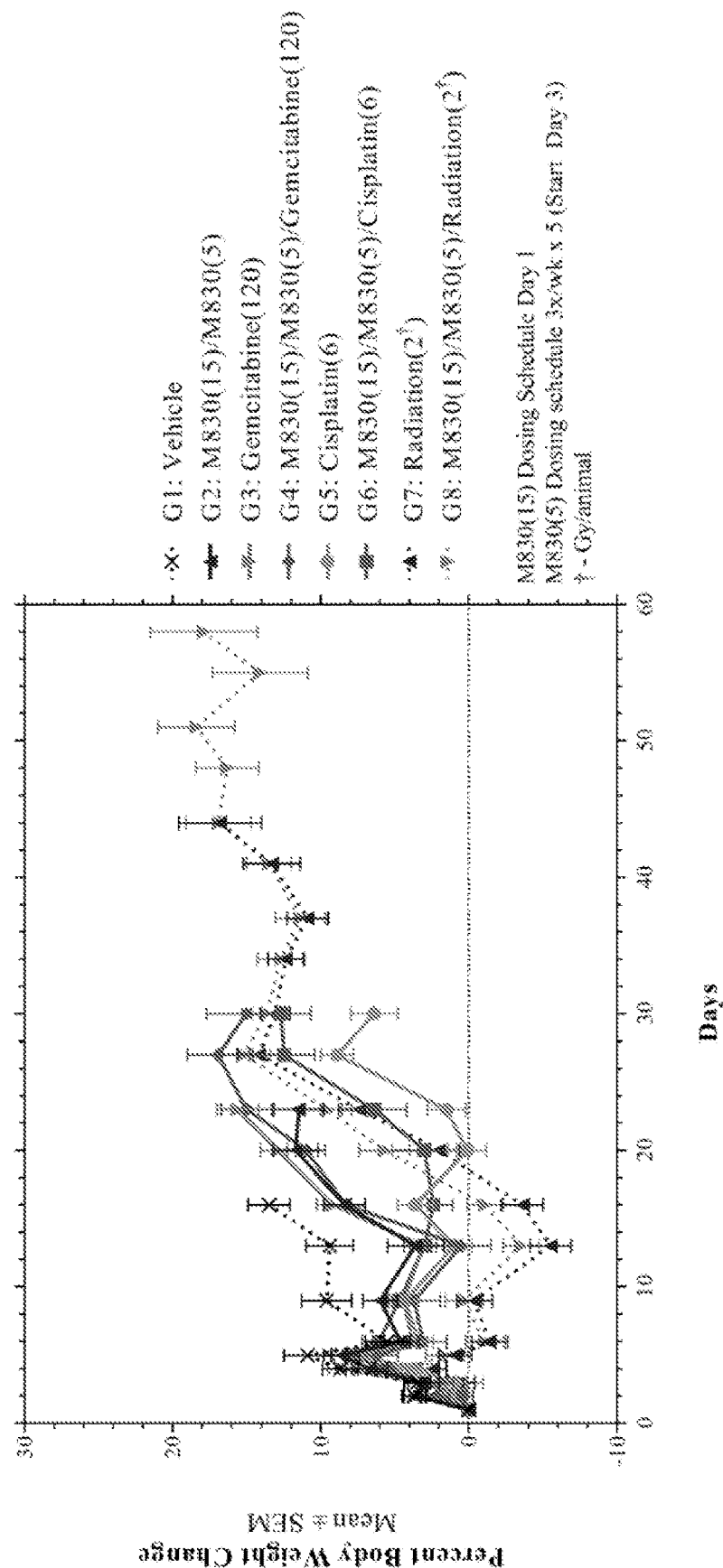

Efficacy of M830 Alone and in Combination with Gemcitabine, Cisplatin, or Radiation Therapy in H460 Human Non-Small Cell Lung Carcinoma Xenograft Model Treatment:

Treatment began on Day 1 in eight groups of nude mice (n=10) with established subcutaneous H460 tumors of 75-126 mm$^3$. The study was designed to evaluate M830 administered i.p. at 15 mg/kg once on Day 1 followed by 5 mg/kg three times weekly for five weeks starting on Day 3, alone and in combination with gemcitabine administered i.p. at 120 mg/kg once every third day for four doses, cisplatin administered i.p. at 6 mg/kg once every week for three weeks, or localized radiation at 2 gray (Gray) administered daily for five days followed by a two day break and then another cycle of five daily doses. The study included the corresponding gemcitabine, cisplatin and radiation monotherapy groups, as well as a vehicle-treated tumor growth control group. The study endpoint was a tumor volume of 2000 mm$^3$ or the final day, Day 58, whichever came first. All regimens were well tolerated, with no treatment related deaths, no noteworthy clinical signs, and acceptable mean body weight losses (FIG. 7E). The median TTE for controls was 15.6 days, establishing a maximum possible TGD of 42.4 days (272%) for the 58-day study.

The M830 and gemcitabine monotherapy treatments resulted in outcomes that were not statistically different from vehicle-treated controls ($P>0.05$). FIGS. 7A-B show mean and median tumor volume, respectively, over the time course of the study. Cisplatin and radiation monotherapies and all three combination therapies produced statistically significant survival benefit compared to vehicle-treated controls (see FIGS. 7C-D). In addition, both the M830/gemcitabine and the M830/radiation combinations were statistically superior to the corresponding monotherapies ($P<0.05$). M830 in combination with radiation was the most active treatment regimen tested in the study with 238% TGD and four Day 58 survivors.

Example 7

Efficacy of M830 Alone and in Combination with Bevacizumab or Irinotecan in the DLD-1 Colorectal Adenocarcinoma Xenograft Model On the day of tumor implant, each test mouse was injected subcutaneously into the flank with $2.5 \times 10^6$ to $5 \times 10^6$ cultured DLD-1 tumor cells. Tumor weights were calculated following surgical removal. M830 was administered i.p. at 5 or 15 mg/kg, three times per week, typically on a Monday, Wednesday, and Friday schedule. Irinotecan was given once per week at 60 mg/kg i.v. and bevacizumab was dosed at 5 mg/kg i.p., three times per week.

Figure 8:
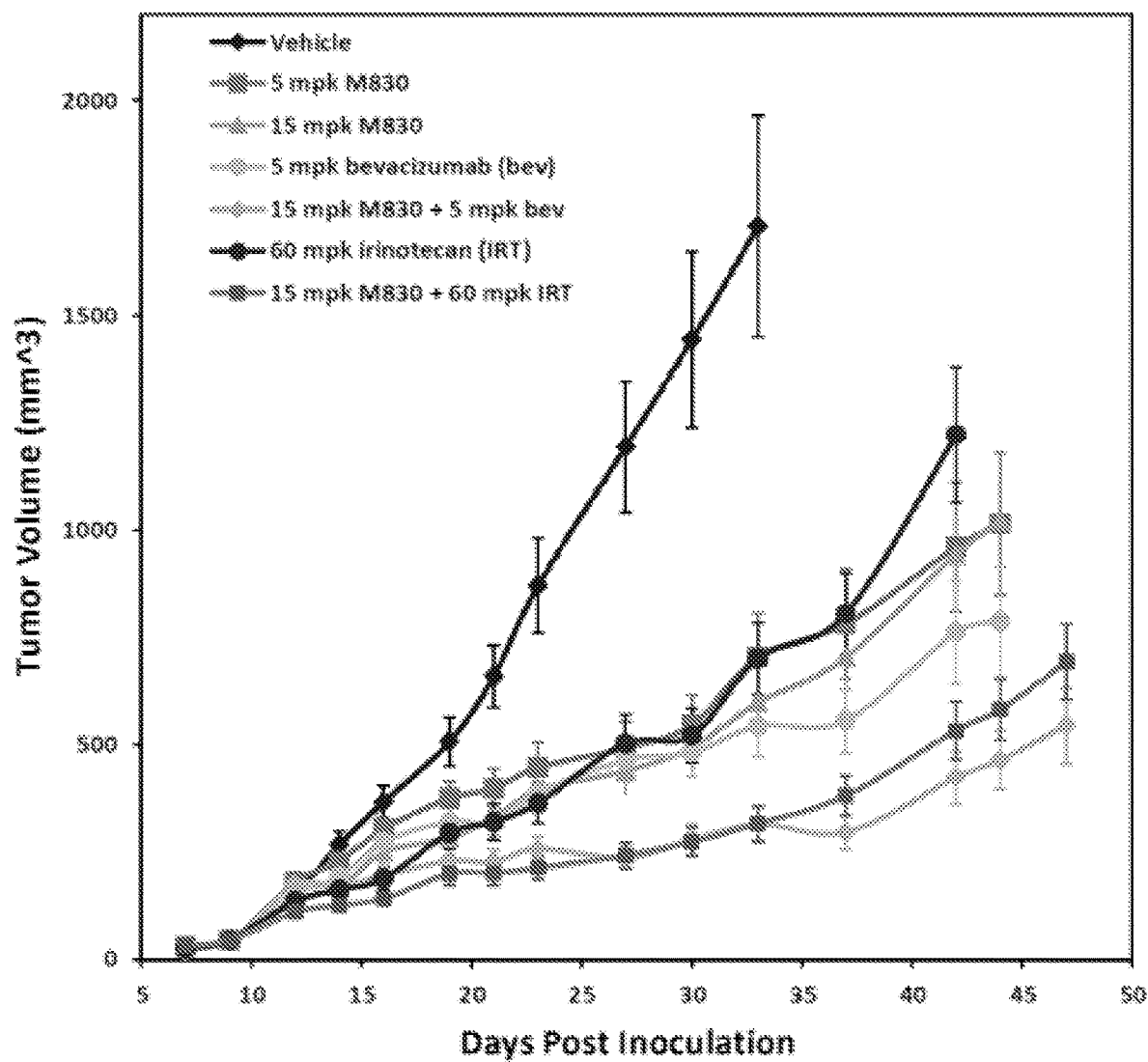
FIG. 8 shows a line graph of tumor volume over time from a study of M830, bevacizumab, irinotecan, and combinations thereof in a DLD-1 colorectal adenocarcinoma xenograft model.

FIG. 8 shows a time course of tumor growth throughout the study. The results show that the combinations of M830/bevacizumab and M830/irinotecan were effective against DLD-1 cancer cells in the xenograft model, and that the combinations were more effective than any agent alone.

In a second study, treatment was initiated with a large tumor volume of approximately 170 mm$^3$. M830 alone or in combinations with bevacizumab, irinotecan, or both, was given as a loading dose of 20 mg/kg followed by 5 mg/kg three times per week. The doses of bevacizumab and irinotecan were the same as in the first study. An additional group received a combination of bevacizumab and irinotecan without the M830 antibody.

Figure 9:
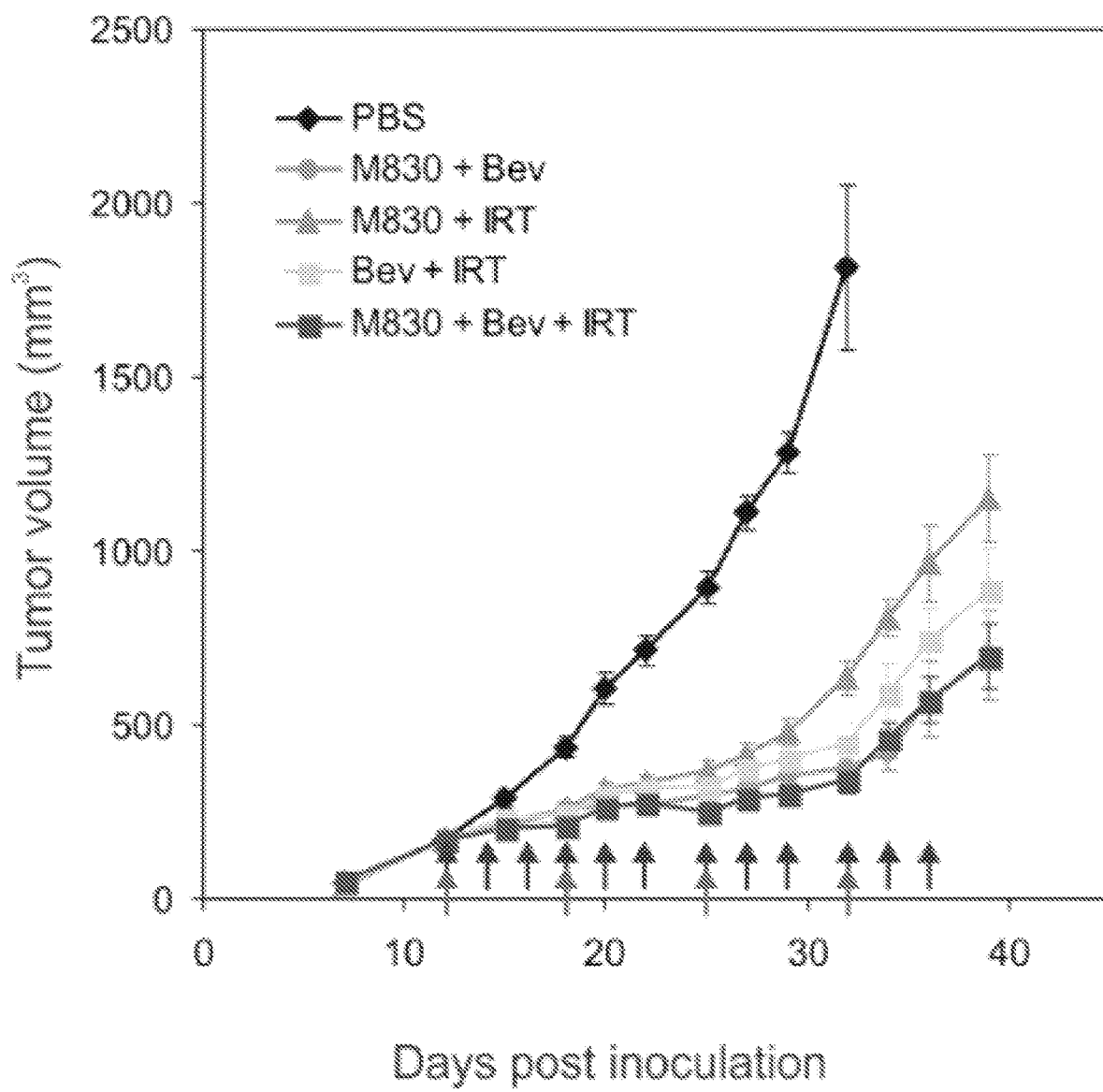
FIG. 9 shows a line graph of tumor volume over time from a study of treatment with combinations of M830, bevacizumab, irinotecan, and the combination of all three treatments in a DLD-1 colorectal adenocarcinoma xenograft model.

FIG. 9 shows a time course of tumor growth throughout the second study. The results show that all combinations of M830, bevacizumab, and irinotecan were effective against DLD-1 cancer cells in the xenograft model, although the triple combination did not outperform the M830/bevacizumab combination therapy.

The study is repeated with one group in each cohort receiving irinotecan at 50 mg/kg once per week i.v. One group in each of the two cohorts receives a combination of 5 mg/kg M830 three times a week with Bevacizumab IP at 5 mg/kg twice per week, fluoropyrimidine at 50 mg/kg once per week intravenously, and irinotecan at 50 mg/kg once per week intravenously. Another group in each of the two cohorts receives 15 mg/kg M830 three times a week with Bevacizumab IP at 5 mg/kg twice per week, fluoropyrimidine at 50 mg/kg once per week intravenously, and irinotecan at 50 mg/kg once per week intravenously.

It is expected that the combination of M830, bevacizumab, and fluoropyrimidine-irinotecan will be effective against cancer cells in the xenograft models and that the combination will be more effective, preferably synergistic compared to any agent alone. The study will be repeated using each of M822, M825, and M863 replacing M830, together with bevacizumab and fluoropyrimidine-irinotecan or other therapeutic agents. It is expected that the combination of M822, M825, or M863 with bevacizumab and fluoropyrimidine-irinotecan or other therapeutic agents will be effective against cancer cells in the xenograft models and that each such combination will be more effective, preferably synergistic, compared to any such agent alone.

Example 8

Comparison of M830 Antibody Efficacy in Xenograft Models

Percent tumor reduction and percent tumor reduction vs. combination partner for each xenograft model treated with M830 alone or in combination with other chemotherapeutics is shown in Table 5.

TABLE 5

M830 TEM8 Antibody Efficacies in Xenograft Models

| Antibody | Cancer Model | Combination Partner | % Tumor Reduction vs. Vehicle at Day 21* | % Tumor Reduction vs. combination partner at Day (#) |
|---|---|---|---|---|
| M830 | H460 Lung | Paclitaxel | >100% (−61% regression) | 94% (32) |
| M830 | H460 Lung | Bevacizumab | 94.5% | 58.5% (32) |
| M830 | H460 Lung | N/A | 62% | N/A |
| M830 | DLD1 Colon | Irinotecan | 86% | 53% (21) |
| M830 | DLD1 Colon | Bevacizumab | 86% | 48% (21) |
| M830 | DLD1 Colon | N/A | 68% | N/A |
| M830 | UACC Melanoma | N/A | 65% | N/A |
| M830 | HCT116 Colon | N/A | 39.5% | N/A |

*Treatment initiated with tumor volume of 60-80 mm³ for H460 and HCT116 studies or about 50 mm³ for DLD1 and UACC studies; M830 dosed IP, 3 times per week

Example 9

Efficacy of M830 in MC38 Colon Carcinoma Liver Metastasis Model

Figure 10:
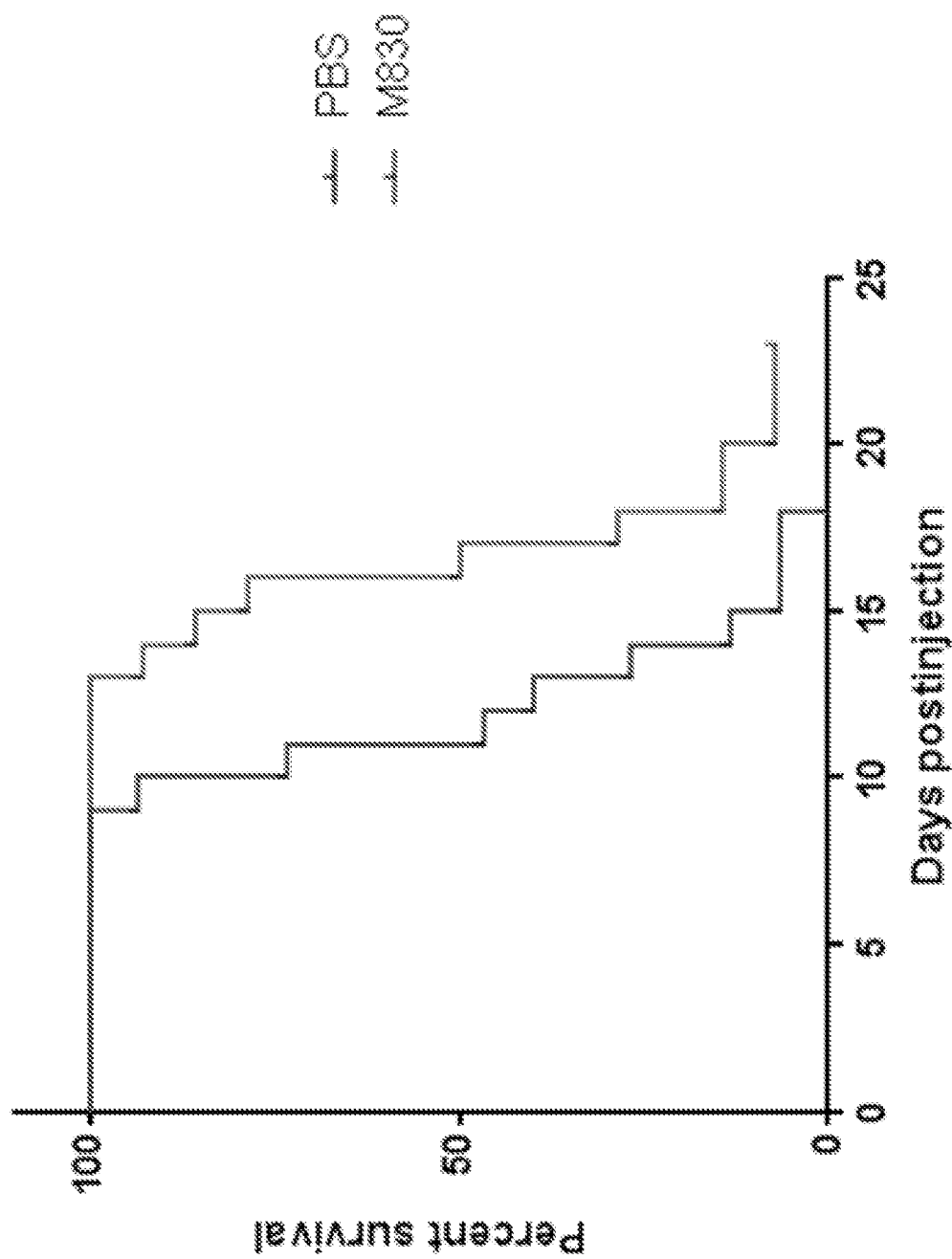
FIG. 10 shows a Kaplan-Meier survival plot demonstrating the effect of M830 antibody in mice in a MC38 colon carcinoma liver metastasis model.

C57BL/6 mice were challenged with MC38 colon carcinoma liver metastasis by intrasplenic injections of cultured cells. FIG. 10 shows that M830 significantly improved the survival of mice in this model (P=0.0001), with a median survival rate of 17 days versus 11 days for vehicle treated mice.

Example 10

Efficacy of TEM8 Antibodies in Combination with Molecularly Targeted Cancer Pathway Inhibitors Athymic nude mice are used. On the day of tumor implant, each test mouse is injected subcutaneously in the right flank with 2.5×10⁶ to 5×10⁶ DLD-1 cells (cohort 1), or 1×10⁷ cells H460 cells (cohort 2), and tumor growth is monitored as the average size approaches the target range of 100 to 150 mm³. The endpoint of the study is a tumor volume of 2000 mm³ or the last day of the study, whichever comes first.

Monotherapy Treatments

Two groups in each cohort receive M830 at 5 and 15 mg/kg three times a week. Two groups in each cohort receive the COX2 inhibitor celecoxib at 25 and 75 mg/kg daily. (Park et al., 2008). One group in each cohort receives the non-steroidal anti-inflammatory (NSAID) ibuprofen in chow at 1360 mg/kg. (Yao et al., 2005). One group in each cohort receives the prostaglandin E₂ (PGE₂) synthase inhibitor sulindac sulphide orally at 20 mg/kg per day. (Mahmoud et al., 1998).

Combination Treatments

One group in each of the two cohorts receives a combination of 5 mg/kg M830 three times a week with celecoxib orally at 25 mg/kg daily. Another group in each of the two cohorts receives a combination of 5 mg/kg M830 three times a week with celecoxib orally at 75 mg/kg daily. A further group in each of the two cohorts receives a combination of 15 mg/kg M830 three times a week with celecoxib orally at 25 mg/kg daily. An additional group in each of the two cohorts receives a combination of 15 mg/kg M830 three times a week with celecoxib orally at 75 mg/kg daily.

One group in each of the two cohorts receives a combination of 5 mg/kg M830 three times a week with ibuprofen in chow at 1360 mg/kg. Another group in each of the two cohorts receives 15 mg/kg M830 three times a week with ibuprofen in chow at 1360 mg/kg.

One group in each of the two cohorts receives a combination of 5 mg/kg M830 three times a week with sulindac sulphide orally at 20 mg/kg per day. Another group in each of the two cohorts receives 15 mg/kg M830 three times a week with sulindac sulphide orally at 20 mg/kg per day.

Results

It is expected that the combination of M830 and celecoxib, M830 and ibuprofen, and M830 and sulindac sulphide will be effective against cancer cells and/or tumor associated stroma and/or tumor vasculature in the xenograft models and that the combination will be more effective, preferably synergistic, compared to any agent alone. The study will be repeated using each of M822, M825, and M863 replacing M830, together with celecoxib or other COX-2 inhibitors, ibuprofen or other NSAIDs, and sulindac sulphide or other PGE₂ synthase inhibitors. It is expected that these combinations will also be effective against cancer cells and/or tumor associated stroma and/or tumor vasculature in the xenograft models and that each such combination will be more effective, preferably synergistic, compared to any such agent alone.

Example 11

Affinity and Pharmacokinetics of TEM8 Antibodies

Table 6 shows Biocore affinity measurements of anti-TEM8 fragment antigen-binding (Fabs).

TABLE 6

Binding affinities of TEM8 antibodies

| | M830 | | | M825 | | |
|---|---|---|---|---|---|---|
| | ka (1/Ms) | kd (1/s) | $K_D$ (M) | ka (1/Ms) | kd (1/s) | $K_D$ (M) |
| mTEM8-Fc | 7.749E+5 | 0.002901 | 3.744E−9 | 1.700E+6 | 8.942E−5 | 5.261E−11 |
| hTEM8-AP | 6.071E+5 | 9.533E−4 | 1.570E−9 | 3.050E+6 | 1.802E−4 | 5.909E−11 |

Table 7 shows an in silico assessment of TEM8 antibodies. M830 and M863 have more basic V domains, M825 and M822 have more acidic V domains. The inherent polarity between V and C domains may pose downstream purification challenges. Sequence analysis identified no potential glycosylation sites in any CDRs, eliminating one of the biggest risks for development.

TABLE 7 pI values of TEM8 antibodies

| Antibodies | pI calculated based on variable domains only | pI calculated based on IgG1 |
|---|---|---|
| M822 | 5.39 | 7.91 |
| M825 | 5.47 | 7.91 |
| M830 | 10.17 | 8.75 |
| M863 | 10.11 | 8.68 |

Tables 8 and 9 show pharmacokinetic properties of TEM8 antibodies according to the present invention in mouse for single dose (Table 8) and multiple dose (Table 9) treatments.

TABLE 8

Single dose summary

| Group | Treatment | CMAX (ng/mL) | TMAX (hr) | AUCI (hr*ng/mL) | AUCT (hr*ng/mL) | HALF (hr) | CLF (mL/hr/kg) | VZF (mL/kg) | KEL (1/hr) |
|---|---|---|---|---|---|---|---|---|---|
| 2 | M825 5 mg/kg | 46800 | 3 | 1310519 | 1310222 | 6.03 | 3.82 | 33.19 | 0.1149 |
| 3 | M825 15 mg/kg | 144000 | 3 | 9239202 | 8991767 | 23.77 | 1.62 | 55.66 | 0.0292 |
| 4 | M822 5 mg/kg | 42100 | 3 | 1611073 | 1610845 | 5.75 | 3.10 | 25.73 | 0.1206 |
| 5 | M822 15 mg/kg | 182000 | 24 | 13523442 | 13522827 | 10.50 | 1.11 | 16.80 | 0.0660 |
| 6 | M863 5 mg/kg | 51300 | 3 | 1330847 | 1330742 | 8.59 | 3.76 | 46.56 | 0.0807 |
| 7 | M863 15 mg/kg | 355000 | 3 |  | 10721535 |  |  |  |  |
| 8 | M830 5 mg/kg | 67500 | 3 | 2242485 | 2242286 | 8.54 | 2.23 | 27.48 | 0.0811 |
| 9 | M830 15 mg/kg | 203000 | 3 | 10692742 | 10692598 | 14.94 | 1.40 | 30.24 | 0.0464 |

TABLE 9

Multiple dose summary

| Group | Treatment | CMAX (ng/mL) | TMAX (hr) | AUCI (hr*ng/mL) | AUCT (hr*ng/mL) | HALF (hr) | CLF (mL/hr/kg) | VZF (mL/kg) | KEL (1/hr) |
|---|---|---|---|---|---|---|---|---|---|
| 2 | M825 5 mg/kg | 54300 | 3 | 1408345 | 1408201 | 9.10 | 3.55 | 46.61 | 0.0762 |
| 3 | M825 15 mg/kg | 314000 | 3 | 21649446 | 21648879 | 17.05 | 0.69 | 17.05 | 0.0406 |
| 4 | M822 5 mg/kg | 88000 | 24 |  | 4550095 |  |  |  |  |
| 5 | M822 15 mg/kg | 632000 | 3 | 68241171 | 66575247 | 54.57 | 0.22 | 17.31 | 0.0127 |
| 6 | M863 5 mg/kg | 58600 | 3 | 1425735 | 1425565 | 14.29 | 3.51 | 72.28 | 0.0485 |
| 7 | M863 15 mg/kg | 147000 | 3 | 7272672 | 7271700 | 12.64 | 2.06 | 37.60 | 0.0549 |
| 8 | M830 5 mg/kg | 86400 | 3 | 4316790 | 4315918 | 22.88 | 1.16 | 38.24 | 0.0303 |
| 9 | M830 15 mg/kg | 330000 | 3 | 23053875 | 23052853 | 18.70 | 0.65 | 17.55 | 0.0371 |

Example 12

M825-MMAE In Vitro and Non-GLP Toxicology Studies

3T3 fibroblasts

3T3 cells were cultured and contractility in the presence of TGFb-1 was measured in control or M825 exposed cells. M825 was shown to block the contractility of activated 3T3 fibroblasts in vitro (FIG. 11A-B). Contractile forces are thought to contribute to increased cancer cell invasion.

Toxicology

In a single rising dose phase study design, female (N=3) and male (N=3) rats were given the ADC at intervals of 3 or more days and were monitored for 2 weeks. Clinical observations, body weight, and necropsy results were looked at, as well as the clinical pathology and histopathology for any unscheduled sacrifices. The first dose was 20 mg/kg. This dose was considered toxic as 1 out of 6 rats were found dead, 2 with erected fur, and 3 with BW loss. There were dark foci in many organs, discoloration, platelet decrease, impaired liver and kidney functions, and skin and testis findings. Part of the findings may have been due to toxicity of MMAE. The next dose was 40 mg/kg, which was considered lethal as all rats were found dead or moribund by Day 5. 15 and 10 mg/kg were chosen for the multiple dose phase study.

In the multiple dose phase study design, 5 male and 5 female rats for each cohort were given 3 weekly doses at Days 1, 8, and 15, and sacrificed on Day 18. A vehicle control arm was added. In the 15 mg/kg group, 1 out of 10 animals was found dead (Day 15), 1 moribund (Day 17), 2 had decreased activity (Day 15), 2 had erected fur (Day 15), and 3 had dark foci in the lungs. In the 10 mg/kg group, 1 out of 10 was found dead (Day 16), 2 had decreased activity (Day 15), 2 had erected fur (Day 15), and 1 had dark loci in the lungs. Both groups also had discoloration, skin, thymus, pituitary gland, and lymph node findings, and reduced red blood cell, hemoglobin, and platelet counts.

Example 13

M830 Antibody-Dependent Cell-Mediated Cytotoxicity (ADCC)

Fc mutations which increase ADCC are known in the art. For example, substitutions in the IgG constant region such as S239D, A330L, and I332E are known to increase binding to the FCy receptor. (see, e.g., Lazar et al., Proc. Natl., Acad. Sci. U.S.A., 103:4005-4010, 2006). In the present example, the M830 Fc S239D:I332E double mutant was generated and confirmed by standard molecular biology techniques (830M: S239D/I332E). FIG. 12A is a schematic showing the antibody binding in ADCC and FIG. 12B demonstrates that the Fc mutant form of M830 showed significantly enhanced binding to FcγRIIIa (CD16a).

DOCUMENTS

CODACCI-PISANELLI, G., et al. High-dose 5-fluorouracil with uridine-diphosphoglucose rescue increases thymidylate synthase inhibition but not 5-fluorouracil incorporation into RNA in murine tumors. Oncology 62(4): 363-70.

GEARY, S. M., et al. (2013). The combination of a low-dose chemotherapeutic agent, 5-fluorouracil, and an adenoviral tumor vaccine has a synergistic benefit on survival in a tumor model system. PLOS One 8(6): e67904.

HE, S., et al. (2013). Discovery of highly potent microsomal prostaglandin e2 synthase 1 inhibitors using the active conformation structural model and virtual screen. J Med Chem 56(8): 3296-309.

ST CROIX, B., et al. (2000). Genes expressed in human tumor endothelium. Science 289(5482): 1197-1202.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A composition for treating a tumor in a human subject comprising:
   (a) an anti-metabolite agent or analog thereof selected from the group consisting of antifolates, purine inhibitors, pyrimidine inhibitors, and combinations thereof; and
   (b) a monoclonal antibody or antigen binding fragment thereof, wherein the monoclonal antibody comprises:
      (i) a heavy chain variable region (VH), which comprises an amino acid sequence of SEQ ID NO:5; and
      (ii) a light chain variable region (VL), which comprises an amino acid sequence of SEQ ID NO:6;
      wherein the monoclonal antibody or antigen binding fragment thereof comprises a constant (Fc) region and binds to human tumor endothelial marker 8 (TEM8);
   wherein the tumor comprises one or more of human TEM8 expressing tumor cells and human TEM8 expressing tumor stromal cells.

2. The composition according to claim 1, wherein the tumor cells express human TEM8.

3. The composition according to claim 1, wherein the tumor cells and tumor stromal cells express human TEM8.

4. The composition according to claim 1, wherein the tumor stromal cells express human TEM8.

5. The composition according to claim 1, wherein the tumor is a cancer selected from the group consisting of kidney cancer, colon cancer, lung cancer, liposarcomas, brain cancer, breast cancer, melanoma, liver cancer, head and neck cancer, and prostate cancer.

6. The composition according to claim 1, wherein the monoclonal antibody or antigen binding fragment thereof comprises:
   (1) a VH polypeptide encoded by:

```
                                            (SEQ ID NO: 15)
gaggtgcagctggtggagtctgggggaggcgtggtccagcctggg aggtccgtgagactctcctgtgcagcctctggattcaccttcagt acctatactatgcactgggtccgccaggctccaggcaaggggctg gagtgggtggcaattatctcaaatgatggaagcaataagtactac gcagaccccgtgaggggccgattcaccatctccagagacaattcc aagaacacgctgtatctgcaaatgaacagcctgagagctgaggac
```

-continued acggctgtgtattactgtgtacgtggcagcagctggtatcgcgga aattggttcgaccoctggggccagggaaccctggtcaccgtgagc tca and (2) a VL polypeptide encoded by:

(SEQ ID NO: 16)
gacatccagatgacccagtctccatcctccctgtctgcatctgta ggagacagagtcaccatcgcttgccgggcaagtcagaccattagt aggtatttaaattggtatcagcagaaaccagggaaagcccctaag ctcctgatctatgctgcatccagtttgcaaagtggggtctcatca aggttcagtggcagtggatctgggacagagttcactctcaccatc agcagtctgcagcctgaagattttgcaacttatttctgtcaacag acttacagtcccccgatcaccttcggccaagggacacgactggag attaaacga.

7. The composition according to claim 1, wherein the anti-metabolite agent or analog thereof is selected from the group consisting of 5-fluorouracil, tegafur, capecitabine, cladribine, methotrexate, pemetrexed, hydroxyurea, 2-mercaptopurine, 6-mercaptopurine, fludarabine, gemcitabine, clofarabine, cytarabine, decitabine, floxuridine, nelarabine, pralatrexate, 6-thioguanine, 5-azacytidine, doxifluridine, forodesine, pentostatin, sapacitabine, thiarabine, troxacitabine, raltitrexed, aminopterin, carmofur, azathioprine, 6-azauracil, pharmaceutically acceptable salts thereof, and combinations thereof.

8. A composition comprising:
    (a) an anti-metabolite agent or analog thereof selected from the group consisting of antifolates, purine inhibitors, pyrimidine inhibitors, and combinations thereof; and
    (b) a monoclonal antibody or antigen binding fragment thereof, wherein the monoclonal antibody comprises:
        (i) a heavy chain variable region, which comprises an amino acid sequence selected from SEQ ID NO:5; and
        (ii) a light chain variable region, which comprises an amino acid sequence selected from SEQ ID NO:6
        wherein the monoclonal antibody or antigen binding fragment thereof binds to human tumor endothelial marker 8 (TEM8).

9. A pharmaceutical composition comprising the composition of claim 1 and a pharmaceutically acceptable diluent or carrier.

10. A kit comprising the composition of claim 1 packaged together with instructions for its use.

11. A kit comprising the pharmaceutical composition of claim 9 packaged together with instructions for its use.

* * * * *